(12) United States Patent
Aranyi et al.

(10) Patent No.: US 7,812,031 B2
(45) Date of Patent: Oct. 12, 2010

(54) PYRIMIDINE DERIVATIVES AS OREXIN RECEPTOR ANTAGONISTS

(75) Inventors: Peter Aranyi, Budapest (HU); Maria Balogh, Dunakeszi (HU); Sandor Batori, Budapest (HU); Judit Bence, Budapest (HU); Michel Finet, Budapest (HU); Zoltan Kapui, Budapest (HU); Christophe Philippo, Rueil-Malmaison (FR); Tibor Szabo, Budapest (HU); Zoltan Szlavik, Budapest (HU); Zsuzsanna Tomoskozi, Budapest (HU); Katalin Urban-Szabo, Budapest (HU); Olivier Venier, Rueil Malmaison (FR)

(73) Assignee: Sanofi-Aventis, Paris (FR)

(*) Notice: Subject to any disclaimer, the term of this patent is extended or adjusted under 35 U.S.C. 154(b) by 447 days.

(21) Appl. No.: 11/463,825

(22) Filed: Aug. 10, 2006

(65) Prior Publication Data

US 2007/0043037 A1 Feb. 22, 2007

Related U.S. Application Data

(63) Continuation of application No. PCT/HU2005/000010, filed on Feb. 8, 2005.

(30) Foreign Application Priority Data

Feb. 10, 2004 (HU) .................................. 0400405

(51) Int. Cl.
C07D 239/42 (2006.01)
A61K 31/505 (2006.01)
A61P 43/00 (2006.01)

(52) U.S. Cl. ...................... 514/275; 544/332; 544/330; 544/331; 544/333; 544/335

(58) Field of Classification Search ................. 514/256, 514/275; 544/330, 331, 332, 333, 335
See application file for complete search history.

(56) References Cited

U.S. PATENT DOCUMENTS

| | | | |
|---|---|---|---|
| 2,514,380 A | | 7/1950 | Duschinsky et al. |
| 2,835,669 A | | 5/1958 | Otto |
| 3,467,662 A | | 9/1969 | Frey |
| 3,821,244 A | | 6/1974 | Matier |
| 4,698,340 A | * | 10/1987 | Takaya et al. ............ 514/227.8 |
| 6,274,588 B1 | | 8/2001 | Boes |
| 7,288,544 B2 | * | 10/2007 | Ohno et al. ............ 514/252.14 |

FOREIGN PATENT DOCUMENTS

| | | |
|---|---|---|
| DE | 244321 | 3/1912 |
| DE | 1955318 | 6/1970 |
| FR | 2241305 | 3/1975 |
| GB | 1 159 263 | 7/1969 |
| WO | WO 01 96302 | 12/2001 |
| WO | WO/03/051872 | * 12/2002 |
| WO | WO 03 051872 | 6/2003 |
| WO | WO 2004 041791 | 5/2004 |
| WO | WO 2004 041816 | 5/2004 |
| WO | WO 2006050476 | * 11/2004 |

OTHER PUBLICATIONS

Winrow, et al., Neuropharmacol., vol. 58, #1, Jan. 2010, 185-194.*
Vianna, Autonomic Neuroscience: Basic & Clinical (Abstracts) 149 (2009) 1-126.*
Baker B. R. Shapiro H. S, Analogs of Tetrahydrofolic Acid. IX. Synthesis of N-'1-(2-Amino-4-hydroxy-6-phenyl-5-pyrimid yi)-3-propyl ?p-aminobenzoyl-L-glumtamic Acid, a "Nonclassical" Inhibitor of Some Folic CoFactor Area Enzymes—Journal of Medicinal Chemistry, vol. 6, 1963, pp. 664-669.
Breaux E. J. et al , An improved general synthesis of 4-aryl-5-pyrimidinecarboxylates , Journal of Heterocyclic Chemistry, Heterocorporation, Provo, US, vol. 18, Jan. 1981 pp. 183-184.
Deshmukh M.D et al., Efficient Method for Deamination of Amino pyridines National Academy Science Letters, vol. 21, No. 7, 1998, pp. 247-249.
Dorigo P, Benetollo F. et al , Synthesis and Cardiotonic Activity of Novel Pyrimidine Derivatives: Crystallographic and Quantum Chemical Studies, Journal of Medicinal Chemistry, vol. 39, 1966, pp. 3671-3683.
Matosiuk D et al , Synthesis and CNS Activity of 1-alky-5-arylimidazolidine-2-thiones , Pharmazie, vol. 52, No. 11, 1997, pp. 71-72.
Palankl M. S.S . et al , Structure-Activity Relationship Studies of Ethyl 2-'(3-Methyl-2,5-dioxo(3-pyrrolinyl)) amino?-4-(trifluoromethyl)pyrimidine-4-carboxyl ate: An Inhibitor of AP-1 and nF-kb Medicated Gene Expression Bioorganic & Medicinal Chemistry Letters, vol. 12, 2002, pp. 2573-2577.
Rezende M.C. et al , The Preparation of Potentially Psychoactive beta-alkoxyphenethylamines, Synthetic Communications, vol. 25, No. 8, 1995, pp. 1239-1247.
Shih N-Y et al , Trans-4-Methyl-3-Imidazoyl Pyrrolidine as a potent, highly selective Histamine H3 Receptor Agonist in Vivo, Bioorganic & Medicinal Chemistry Letters, vol. 8, 1988, pp. 243-248.
Welnhardt K et al , Synthesis and Central Nervous System Properties of 2-'(Alkoxycarbonyl)amino?-4(5)-phenyl-2-im idazolines, Journal of Medicinal Chemistry, vol. 27, 1984, pp. 616-627. * cited by examiner

*Primary Examiner*—James O Wilson
*Assistant Examiner*—Cecilia M Jaisle
(74) *Attorney, Agent, or Firm*—Barbara E. Kurys

(57) ABSTRACT

The present invention relates to substituted pyrimidine compounds of formula I useful as orexin receptor antagonists. The invention also relates to pharmaceutical compositions containing said compounds.

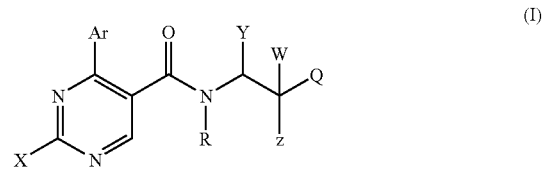

(I)

11 Claims, No Drawings

PYRIMIDINE DERIVATIVES AS OREXIN RECEPTOR ANTAGONISTS

The present invention relates to the orexin receptor antagonist compounds of the general formula (I), as well as their isomers, salts and solvates, to the pharmaceutical compositions containing them and to the therapeutic application thereof.

Further subjects of the invention are the methods of preparation of the compounds of the general formula (I) and the new intermediates of these processes.

Orexines, in other name hypocretin neuropeptides and their receptors were discovered in 1998 by molecular biological methods.

The orexinergic neuropeptides are formed in large amount in the neurons of the lateral hypothalamus, but via axonal transport processes, they also reach numerous remote areas of the nervous system. On the basis of experimental observations the orexinergic system seems to plays crutial role in the feeding, in the sleep-wake cycle and in the regulation of the autonomic nervous system processes.

The orexin A and orexin B proteins are formed by the enzymatic cleavage of their only common precursor, the pre-proorexin protein molecule. Orexin A consists of 33 aminoacid residues with two intramolecular disulphide bridges. Orexin B is a linear protein consisting of 28 aminoacid residues. During the evolution of mammals the aminoacid sequence of the orexin peptides has largely been conserved. In man, pig, dog, mouse and rat species the aminoacid sequences of the orexin A peptides are fully identical, whereas the aminoacid sequences of the orexin B proteins differ only in a few aminoacids. The orexin-producing neurons of the brain form a heterogenous cell population: one part of them exhibits leptin sensitivity, whereas the other part glucose sensitivity.

Further sub-groups of the orexinergic neurones are capable to express galanine, neuropeptide Y or dinorfine, in addition to the orexines.

The orexin A and orexin B bind to specific receptors on the surface of the target cells: i.e. the orexin-1 and orexin-2 receptors.

In men, the orexin-1 receptors consist of 425, whereas the orexin-2 receptors of 444 aminoacid residues, and their aminoacid sequences are in 64% identical. Between the variants of the two orexin receptor types occurring in the different mammal species (man, pig, dog, mouse, rat) a considerable sequence-homology (of 91-98%) can be found. The aminoacid sequence of the human orexin-1 receptor is in 94% identical with the aminoacid sequence of the rat, whereas the sequences of the human and rat orexin-2 receptors are in 95% identical.

The orexin A and B peptides bind with high affinity to both receptor types. Orexin affinities of the two receptor types were determined by intracellular $Ca^{2+}$ concentration measurements in recombinant systems (on CHO cells) and on hypothalamic neurons. Compared to the orexin B, the orexin A peptide was shown to be 10-50-fold more effective on the orexin-1 receptors, demonstrating that this receptor type is selective towards orexin A. On the orexin-2 receptors both neuropeptides exhibited similar, high activities, i.e. the orexin-2 receptors are not selective towards the orexin peptides. According to experimental results, the orexin-1 receptors-via the $G_{q/11}$ sub-class G-proteins—may activate the phospholipase β (PLCβ) enzyme, whereas the orexin-2 receptors are supposed to bind also to the $G_{q/11}$ and $G_{i/o}$ or $G_s$ sub-classess of the G-proteins, thus beside the PLCβ path, they may also influence the cAMP path. In the synaptic activity stimulating effect of the orexines a significant role may be played by their capability to evoke phosphorylation of the ion channels. The orexin-1 and 2 receptor types are most frequent in the central nervous system (brain, spinal marrow), but they can also be found in numerous peripherical tissue types (as for instance in the hypophysis, in the adrenal glands, in the gastro-intestinal tract, in the pancreas and in the kidney).

Orexines play important role in the regulation of the eating behavior, the sleeping-wake cycle, the neuroendocrinological processes and in the complex regulation of the energy consumption, Orexines in the central nervous system get in interaction with a number of specific neuron-nuclea, as for instance with the feeding centres of the hypothalamus, with the sleep-wake centres in the brain steam, with the symphatic and parasymphatic neuron nuclea and with the limbic system. After ventricular administration, orexines enhance in a dose-dependent manner the food-intake, the length of the time of wakefulness, the motoric activity, the speed of the metabolic processes, the heart rhythm and the blood pressure. Latest electrophysiological studies have demonstrated that in the regulation of the functions of the orexin-producing neurons important mediators of the metabolic processes take part, such as the leptin, the glucose, the grelin, the monoamines and the acetylcholine, which means that the orexin-producing neurones develop functional connections with the feeding-centres, with monoaminerg-acetylcholinerg centres in the brain stem and with the factors reflecting the supply with food.

Orexins and their receptors can also be found in the peripheric tissues. Orexins exert a direct effect on the hypophysis and on the hormone secretion of the adrenal glands and they influence considerably the digestion and absorption processes acting locally, along the gastro-intestinal tract.

The orexin-A can effectively increase both in vitro and in viva the insulin secretion of the pancrease and the leptin secretion of the lipides.

These observations prove that the orexinergic neuropeptides and their receptors play important role in the energy intake—expenditure balance and in the higher regulation of the adaptive behavioral processes.

Based on the above, we can expect that compounds exerting antagonistic effect on the orexin-1 and orexin-2 receptors are suitable—among others—to treat diseases like obesity, including obesity of the non-insulin-dependent diabetes patients, for the treatment of sleeping disorders, stroke, nausea and vomiting.

We aimed to prepare novel compounds suitable for drug development, exerting strong antagonistic effect on the orexin-1 and orexin-2 receptors, first of all on the orexin-1 receptors.

We have found that the compounds of the general formula (I)

wherein

X stands for $C_{1-4}$-allyl group; amino group—optionally substituted with one or two $C_{1-4}$ alkyl group, $C_{1-4}$-allyl-S-group;

saturated or partially saturated mono- or bicyclic moiety containing 1 or 2 or 3 heteroatoms (N, O or S) and connected to the pyrimidine ring through the nitrogen atom; or benzylamino-, phenylethylamino-, N—$C_{1-4}$ alkylbenzylamino-, N—$C_{1-4}$ alkylphenylethylamino-, N—$C_{1-4}$-hydroxyalkylbenzylamino-, N—$C_{1-4}$-hydroxyalkylphenylethylamino-, cyclohexylmethylamino-, N—($C_{1-4}$-cyclohexyl-methyl)amino-group—where the aromatic ring is optionally substituted with one or two of the same or different $C_{1-4}$ alkyl- or $C_{1-4}$ alkoxy group or hydroxy group or halogen atom; or X stands for a Het-$C_{1-4}$ alkyl-N($R^1$)-group, where the meaning of Het is a saturated or unsaturated heterocyclic ring containing one or two identical or different heteroatoms (N, O vagy S), optionally substituted with one or more identical or different $C_{1-4}$ alkyl-, $C_{1-4}$ alkoxy group or halogen atom and $R^1$ means $C_{1-4}$ alkyl-group or a $C_{1-4}$-hydroxyalkyl group.

Ar stands for phenyl group or a 5- or 6-membered heterocyclic ring containing 1-3 identical or different heteroatoms or a methylenedioxyphenyl group-optionally substituted with one or more identical or different $C_{1-4}$ alkyl group, halogen atom, hydroxyl group, $C_{1-4}$ alkoxy group, trihalogenomethyl group, —NH$C_{1-4}$ alkyl, —N($C_{1-4}$ alkyl)$_2$ or —NSC(=O)—$C_{1-4}$ alkyl group;

R represents hydrogen atom or $C_{1-4}$-alkyl group;
Y represents hydrogen atom or $C_{1-4}$-alkyl group;
W represents hydrogen atom or $C_{1-4}$-alkyl group;
Z represents hydroxyl group, halogen atom, $C_{1-4}$-alkoxy group, amino-group, $C_{1-4}$-alkyl-amino-group, —NH-CO$C_{1-4}$-alkyl group;
R+Y may mean—together with the included nitrogen and carbon atom—a

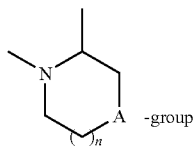

wherein A stands for CH$_2$ group, oxygen atom, NH, NC$_{1-4}$-alkyl group; n=0, 1, 2 R+Z together may mean a —(CH$_2$)$_m$-G-group, wherein m=1, 2, 3, G means oxygen atom, CH$_2$, NH, NC$_{1-4}$-alkyl group;

Z+W together may mean an oxo group;

The meaning of Q is a 5- or 6-membered heterocyclic ring containing 1-3 heteroatoms, optionally substituted with one or more identical or different $C_{1-4}$-alkyl-, $C_{1-4}$-alkoxy- or hydroxyl group, or halogen atom, or a

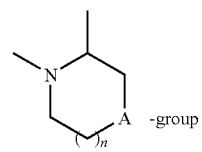

wherein the meaning of $R^2$ is hydrogen atom, halogen atom, hydroxyl-, cyano-, $C_{1-4}$-alkoxy- or $C_{1-4}$-alkyl-group;

$R^3$ stands for hydrogen atom, halogen atom, hydroxyl group, trihalogenomethyl group, amino-, cyano-, $C_{1-4}$-alkylamino-, di($C_{1-4}$)alkylamino-, benzylamino-, benzyl-($C_{1-4}$)alkylamino-group, nitro group, benzyl group, phenylethyl group or $C_{1-4}$-alkyl group, —OR$^5$ group—wherein $R^5$ represents a $C_{1-4}$-alkyl group or benzyl group—optionally substituted with one or more halogen atom, trihalogenomethyl group-; or —NH—C(=O)—$R^6$ group, wherein $R^6$ stands for phenyl group or 4-7-membered cycloalkyl group, methylenedioxyphenyl group, $C_{1-4}$ alkyl group, benzyl group or a heterocyclic ring containing 1 or 2 or 3 heteroatoms, optionally substituted with halogen atom, $C_{1-4}$ alkyl group, $C_{1-4}$-alkoxy group; or a —NH—C(=O)—NH—$R^7$ group wherein the meaning of $R^7$ is $C_{1-4}$ alkyl group, benzyl group or a phenyl group—optionally mono- or polysubstituted with halogen atom, $C_{1-4}$ alkoxy group, $C_{1-4}$ alkyl group or trihalogenomethyl group;

$R^4$ stands for hydrogen atom, halogen atom, hydroxyl group, cyano-group, $C_{1-4}$ alkoxy group or $C_{1-4}$ alkyl group; or $R^3$ and $R^4$ together mean a —O—CH$_2$—O-group; with the proviso that, if Q represents a 5- or 6-membered heterocyclic ring containing 1-3 heteroatom—optionally substituted with one or more identical or different $C_{1-4}$ alkyl-, $C_{1-4}$ alkoxy-, hydroxyl-group or halogen atom, W represents hydrogen atom, Z represents hydroxyl group, R+Y may form together with the included nitrogen and carbon atom a

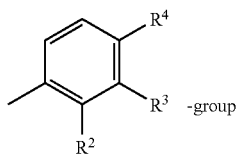

where
n=1,

A represents NH— or NC$_{1-4}$-alkyl or CH$_2$— group, and the meaning of Ar is as defined above, then the meaning X is different from $C_{1-4}$alkyl-group or from an amino group—optionally substituted with one or two $C_{1-4}$ allyl group.

and their salts, isomers and solvates exert significant orexin-1 and orexin-2 receptor antagonistic activity, first of all orexin-1 antagonistic activity and they are suitable for drug development.

One group of the above family is formed by those compounds of the general formula (I) where the meaning of X and Ar is defined in claim 1, W means hydrogen atom or $C_{1-4}$-alkyl-group;

Z stands for hydroxyl group, halogen atom, $C_{1-4}$-alkoxy group, amino group, $C_{1-4}$-allyl-amino group, —NH-CO$C_{1-4}$ alkyl group; or Z+W form together an oxo-group;

R+Y form together with the included nitrogen and carbon atom a

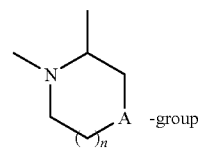

A stands for oxygen atom, —CH$_2$—, —NH—, —NC$_{1-4}$-alkyl-group and the value of n is 0, 1 or 2;

Q represents a 5- or 6-membered heterocyclic ring containing 1-3 heteroatom—optionally substituted with one or more identical or different $C_{1-4}$ alkyl-, $C_{1-4}$ alkoxy-, hydroxyl-group or halogen atom, with the proviso that, if if W represents hydrogen atom,
Z represents hydroxyl group,
n is 1,
A represents —NH—, or —N$C_{1-4}$ alkyl- or —$CH_2$— group,
then the meaning of X is different from $C_{1-4}$ alkyl group and different from an amino group—optionally substituted with one or more $C_{1-4}$ alkyl-group;

A further group of the compounds of the general formula (I) are those where
X and Ar have the meaning as defined in claim 1,
W represents hydrogen atom or $C_{1-4}$ alkyl group;
Z stands for hydroxyl group, halogen atom, $C_{1-4}$-alkoxy group, amino group, $C_{1-4}$-alkyl-amino group, —NHCO $C_{1-4}$-alkyl group; or
Z+W form together an oxo-group;
R+Y may form together with the included nitrogen and carbon atom a

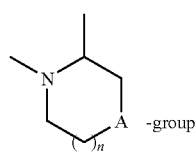

A stands for oxygen atom, —$CH_2$—, —NH—, —N$C_{1-4}$-alkyl-group and the value of n is 0, 1 or 2;
Q represents

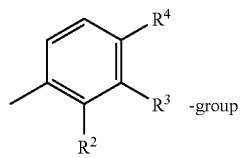

where $R^2$ stands for hydrogen atom, halogen atom, hydroxyl group, $C_{1-4}$ alkoxy group or $C_{1-4}$ alkyl group;
$R^3$ stands for hydrogen atom, halogen atom, hydroxyl group, trihalogenomethyl group, amino-, $C_{1-4}$-alkylamino-, di($C_{1-4}$)alkylamino-, benzylamino-, benzyl-($C_{1-4}$)alkylamino-group, nitro group, benzyl group, phenylethyl group or $C_{1-4}$-alkyl group, —$OR^5$ group—wherein $R^5$ represents a $C_{1-4}$-alkyl group or benzyl group—optionally substituted with one or more halogen atom, trihalogenomethyl group, or —NH—C(=O)—$R^6$ group, wherein $R^6$ stands for phenyl group—optionally substituted with one or more halogen atom, $C_{1-4}$ allyl group, $C_{1-4}$ alkoxy group; or a 4-7-membered cycloalkyl group, methylenedioxyphenyl group, $C_{1-4}$ alkyl group, benzyl group or a heterocyclic ring containing 1 or 2 or 3 heteroatoms, or
—NH—C(=O)—NH—$R^7$ group where $R^7$ stands for $C_{1-4}$-alkyl group, benzyl group, or phenyl group, optionally mono- or polysubstituted with halogen atom, $C_{1-4}$-alkoxy group, $C_{1-4}$-alkyl group or trihalogenomethyl group,
$R^4$ represents hydrogen atom, halogen atom, hydroxyl group, $C_{1-4}$-alkoxy group or $C_{1-4}$ alkyl group; or where
X and Ar have the meaning as defined in claim 1,
Y represents hydrogen atom or $C_{1-4}$ alkyl group;
W represents hydrogen atom or $C_{1-4}$ alkyl group;
Z stands for hydroxyl group, halogen atom, $C_{1-4}$-alkoxy group, amino group, $C_{1-4}$-alkyl-amino group, —NHCO $C_{1-4}$-alkyl group; or
R+Z form together a —$(CH_2)_m$-G-group, where the value of m is 1, 2 or 3 and C represents oxygen atom, —$CH_2$—, —NH— or —N$C_{1-4}$-allyl-group;
Q represents a 5- or 6-membered heterocyclic ring containing 1-3 heteroatom—optionally substituted with one or more identical or different $C_{1-4}$ alkyl-, $C_{1-4}$ alkoxy-, hydroxyl-group or halogen atom, or a

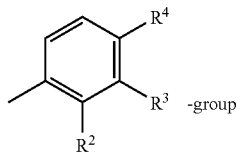

wherein $R^2$ represents hydrogen atom, halogen atom, hydroxyl group, $C_{1-4}$ alkoxy group or $C_{1-4}$ alkyl group;
$R^3$ stands for hydrogen atom, halogen atom, hydroxyl group, trihalogenomethyl group, amino-, $C_{1-4}$-alkylamino-, di($C_{1-4}$)alkylamino-, benzylamino-, benzyl-($C_{1-4}$)alkylamino-group, nitro group, benzyl group, phenylethyl group or $C_{1-4}$-alkyl group,
—$OR^5$ group—wherein $R^5$ represents a $C_{1-4}$-alkyl group or benzyl group—optionally substituted with one or more halogen atom, trihalogenomethyl group, or
—NH—C(=O)—$R^6$ group, wherein $R^6$ stands for phenyl group—optionally substituted with halogen atom, $C_{1-4}$ alkyl group, $C_{1-4}$ alkoxy group; or a 4-7-membered cycloalkyl group, methylenedioxyphenyl group, $C_{1-4}$ alkyl group, benzyl group or a heterocyclic ringy containing 1 or 2 or 3 heteroatoms,
or —NH—C(=O)—NH—$R^7$ group wherein $R^7$ means $C_{1-4}$ alkyl group, benzyl group or a phenyl group—optionally substituted with halogen atom, $C_{1-4}$ alkoxy group, $C_{1-4}$ alkyl group or trihalogenomethyl group,
$R^4$ stands for hydrogen atom, halogen atom, hydroxyl group, $C_{1-4}$ alkoxy group or $C_{1-4}$ alkyl group;

A further group of the compounds of the general formula (I) are those where
X and Ar have the meaning as defined in claim 1,
R represents hydrogen atom or $C_{1-4}$ alkyl group;
Y represents hydrogen atom or $C_{1-4}$ alkyl group;
W represents hydrogen atom or $C_{1-4}$ alkyl group;
Z stands for hydroxyl group, halogen atom, $C_{1-4}$-alkoxy group, amino group, $C_{1-4}$-alkyl-amino group, —NHCO $C_{1-4}$-alkyl group; or
Z+W form together an oxo-group;
Q represents

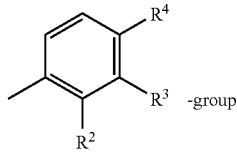

wherein $R^2$ represents hydrogen atom, halogen atom, hydroxyl group, $C_{1-4}$ alkoxy group or $C_{1-4}$ alkyl group;
$R^3$ stands for hydrogen atom, halogen atom, hydroxyl group, trihalogenomethyl group, amino-, $C_{1-4}$-alkylamino-, di($C_{1-4}$)alkylamino-, benzylamino-, benzyl-($C_{1-4}$)alkylamino-group, nitro group, benzyl group, phenylethyl group, $C_{1-4}$-alkyl group or
—$OR^5$ group—wherein $R^5$ represents a $C_{1-4}$-alkyl group or benzyl group—optionally substituted with one or more halogen atom, trihalogenomethyl group-; or
—NH—C(=O)—$R^6$ group, wherein $R^6$ stands for phenyl group—optionally substituted with halogen atom, $C_{1-4}$ allyl group, $C_{1-4}$ alkoxy group, 4-7-membered cycloalkyl group, methylenedioxyphenyl group, $C_{1-4}$ alkyl group, benzyl group or a heterocyclic ring containing 1 or 2 or 3 heteroatoms,
or —NH—C(=O)—NH—$R^7$ group wherein $R^7$ means $C_{1-4}$ alkyl group, benzyl group or a phenyl group—optionally substituted with one or more halogen atom, $C_{1-4}$ alkoxy croup, $C_{1-4}$ alkyl group or trihalogenomethyl group,
$R^4$ stands for hydrogen atom, halogen atom, hydroxyl group, $C_{1-4}$ alkoxy group or $C_{1-4}$ alkyl group;
A further group of the compounds of the general formula (I) are those where
X and Ar have the meaning as defined in claim 1,
R represents hydrogen atom or $C_{1-4}$ alkyl group;
Y represents hydrogen atom or $C_{1-4}$ alkyl group;
W represents hydrogen atom or $C_{1-4}$ alkyl group;
Z stands for hydroxyl group, halogen atom, $C_{1-4}$-alkoxy group, amino group, $C_{1-4}$-alkylamino group, —NHCO $C_{1-4}$-alkyl group; or
Z+W form together an oxo-group;
Q represents a 5- or 6-membered heterocyclic ring containing 1-3 heteroatom—optionally substituted with one or more identical or different $C_{1-4}$ allyl-, $C_{1-4}$ alkoxy-, hydroxyl-group or halogen atom.
A further group of the compounds of the general formula (I) are those where
X represents benzylamino group, —N—$C_{1-4}$-alkyl-benzyl-amino group—where the aromatic ring of the benzyl group may optionally be substituted with one or more identical or different $C_{1-4}$-alkyl group, $C_{1-4}$-alkoxy group, halogen atom or hydroxyl group;
Ar means phenyl group—optionally substituted with one or more identical or different $C_{1-4}$-alkyl group, $C_{1-4}$-alkoxy group, halogen atom trihalogenomethyl group or hydroxyl group;
R+Y may form together with the included nitrogen atom and carbon atom a

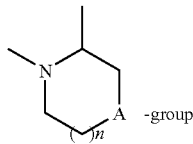

wherein
A means oxygen atom, —$CH_2$—, —NH— or —N—$C_{1-4}$-alkyl-group and the value of n is 0, 1 or 2;
W represents hydrogen atom;
Z represents hydroxyl group;
Q represents a phenyl group or a 5- or 6-membered heterocyclic ring containing 1-3 identical or different heteroatom—optionally substituted with one or more identical or different halogen atom, Cab alkyl-, $C_{1-4}$ alkoxy-, hydroxyl-group.

The denomination "5- or 6-membered heterocyclic ring containing 1-3 identical or different heteroatoms" may mean for example a 2-, 3- or 4-pyridyl or 2-thienyl or 3-thienyl group.

The denomination "saturated or partially saturated mono- or bicycle containing 1-3 heteroatoms" may mean for example pyrrolidinyl, morpholinyl, piperidinyl or tetrahydroisoquinolinyl moiety.

The denomination "Het" means a heterocyclic moiety containing 1 or 2 identical or different heteroatoms (N, O or S), as for example a furanyl-, pyridyl-, thienyl- or morpholinyl group.

The "4-7-membered cycloalkyl group" may mean for example a cyclobutyl, cyclopentyl or cyclohexyl group.

By $C_{1-4}$ alkyl group we mean groups with straight or branched carbon chains, for instance a n-propyl, ethyl, n-butyl or tert.-butyl groups.

By $C_{1-4}$ alkoxy group we mean groups with straight or branched carbon chains, for instance a methoxy, ethoxy, isopropoxy or secondary butyloxy group.

By a bicyclic ring optionally containing heteroatoms we mean for example a quinoline, isoquinoline, quinoxaline, benzotriazine or benzthiazole ring. By halogen atom we mean fluoro, chloro, bromo or iodo atom.

By trihalogenomethyl group we mean for example trifluoromethyl-, trichloromethyl- or tribromomethyl-group.

Far from being complete, hereby we list some of the very active compounds of the general formula (I) according to our invention:

2-Dimethylamino-4-phenylpyrimidine-5-carboxylic acid [2-hydroxy-2-(3-hydroxyphenyl) ethyl]methyl amide;

2-Dimethylamino-4-(2-chlorophenyl)pyrimidine-5-carboxylic acid [2-hydroxy-2-(3-hydroxyphenyl)ethyl]methyl amide;

4-Phenyl-2-[(thiophen-2-yl-methyl)amino]pyrimidine-5-carboxylic acid [2-hydroxy-2-(3-hydroxyphenyl)ethyl] methyl amide;

2-(Benzylmethylamino)-4-phenylpyrimidine-5-carboxylic acid [2-hydroxy-2-(3-hydroxy-phenyl)ethyl]methyl amide;

2-Benzylamino-4-phenylpyrimidine-5-carboxylic acid [2-hydroxy-2-(3-hydroxyphenyl) ethyl]methyl amide;

2-[Benzyl-(2-hydroxyethyl)amino]-4-phenylpyrimidine-5-carboxylic acid [2-hydroxy-2-(3-hydroxyphenyl)ethyl] methyl amide;

2-(Benzylmethylamino)-4-(2-chlorophenyl)pyrimidine-5-carboxylic acid [2-hydroxy-2-(3-hydroxyphenyl)ethyl] methyl amide;

2-(Benzylmethylamino)-4-(2-methylphenyl)pyrimidine-5-carboxylic acid [2-hydroxy-2-(3-hydroxyphenyl)ethyl] methyl amide;

2-(Benzylmethylamino)-4-(2-methoxyphenyl)pyrimidine-5-carboxylic acid [2-hydroxy-2-(3-hydroxyphenyl)ethyl] methyl amide;

2-(2-Chlorobenzylamino)-4-phenylpyrimidine-5-carboxylic acid [2-hydroxy-2-(3-hydroxy phenyl)ethyl]methyl amide;

4-Phenyl-2-[methyl-(pyridin-2-ylmethyl)amino]pyridine-5-carboxylic acid [2-hydroxy-2-(3-hydroxyphenyl)ethyl] methyl amide;

2-(Benzylmethylamino)-4-(2-iodophenyl)pyrimidine-5-carboxylic acid [2-hydroxy-2-(3-hydroxyphenyl)ethyl]methyl amide;

2,2-Dimethylpropionic acid 3-{2-[(2-dimethylamino-4-phenylpyrimidine-5-carbonyl) methylamino]-1-hydroxyethyl}phenyl ester;

2,2-Dimethylpropionic acid 3-{2-[(2-dimethylamino-4-thiophen-3-yl-pyrimidine-5-carbonyl)methylamino]-1-hydroxyethyl}phenyl ester;

2,2-Dimethylpropionic acid 3-{2-[(2-dimethylamino-4-thiophen-2-yl-pyrimidine-5-carbonyl)methylamino]-1-hydroxyethyl}phenyl ester;

2,2-Dimethylpropionic acid 3-{2-[(2-dimethylamino-4-(2-chlorophenyl)pyrimidine-5-carbonyl)methylamino]-1-hydroxyethyl}phenyl ester;

2,2-Dimethylpropionic acid 3-{2-[(2-dimethylamino-4-(3-chlorophenyl)pyrimidine-5-carbonyl)methylamino]-hydroxyethyl}phenyl ester;

2,2-Dimethylpropionic acid 3-{2-[(2-dimethylamino-4-(3-fluorophenyl)pyrimidine-5-carbonyl)methylamino]-1-hydroxyethyl}phenyl ester;

2,2-Dimethylpropionic acid 3-{2-[(2-dimethylamino-4-(4-methoxyphenyl)pyrimidine-5-carbonyl)methylamino]-1-hydroxyethyl}phenyl ester;

2,2-Dimethylpropionic acid 3-{2-[(2-dimethylamino-4-(3,4-methylenedioxyphenyl) pyrimidine-5-carbonyl)methylamino]-1-hydroxyethyl}phenyl ester;

2-Dimethylamino-4-phenylpirimidine-5-carboxylic acid [2-(3-benzyloxyphenyl)-2-hydroxyethyl]methyl amide 2-Dimethylamino-4-(2-fluorophenyl)pyrimidine-5-carboxylic acid [2-(3-benzyloxy phenyl)-2-hydroxyethyl] methyl amide;

2-Dimethylamino-4-(2-chlorophenyl)pyrimidine-5-carboxylic acid [2-(3-benzyloxy phenyl)-2-hydroxyethyl] methyl amide;

4-Phenyl-2-[(pyridin-2-yl-methyl)amino]pyrimidine-5-carboxylic acid (2-hydroxy-1-methyl-2-phenylethyl)methyl amide;

2-(Benzylmethylamino)-4-phenylpyrimidine-5-carboxylic acid (2-hydroxy-1-methyl-2-phenylethyl)methyl amide;

2-(Benzylmethylamino)-4-(2-chlorophenyl)pyrimidin-5-carboxylic acid (2-hydroxy-1-methyl-2-phenylethyl)methyl amide;

2-Benzylamino-4-phenylpyrimidine-5-carboxylic acid (2-hydroxy-1-methyl-2-phenylethyl)methyl amide;

4-Phenyl-2-[(thiophen-2-ylmethyl)amino]pyrimidine-5-carboxylic acid (2-hydroxy-1-methyl-2-phenylethyl)methyl amide;

4-Phenyl-2-[(pyridin-2-ylmethyl)amino]pyrimidine-5-carboxylic acid (2-hydroxy-1-methyl-2-phenylethyl)methyl amide;

2-Dimethylamino-4-phenylpyrimidine-5-carboxylic acid (2-hydroxy-2-{3-[(pyridin-2-carbonyl)amino]phenyl}ethyl)methyl amide;

2-Dimethylamino-4-phenylpyrimidine-5-carboxylic acid [2-(3-benzoylaminophenyl)-2-hydroxyethyl]methyl amide;

2-Dimethylamino-4-phenylpyrimidine-5-carboxylic acid {2-hydroxy-2-[3-(2-methoxy benzoylamino)phenyl]ethyl}methyl amide;

2-Dimethylamino-4-phenylpyrimidine-5-carboxylic acid {2-hydroxy-2-[3-(3-methoxy benzoylamino)phenyl]ethyl}methyl amide;

2-Dimethylamino-4-phenylpyrimidine-5-carboxylic acid (2-hydroxy-2-{3-[(thiophen-2-carbonyl)amino]phenyl}ethyl)methyl amide;

2-Dimethylamino-4-phenylpyrimidine-5-carboxylic acid (2-hydroxy-2-{3-[(thiophen-3-carbonyl)amino]phenyl}ethyl)methyl amide;

2-Dimethylamino-4-phenylpyrimidine-5-carboxylic acid (2-{3-[(furan-3-carbonyl)amino]phenyl}-2-hydroxyethyl)methyl amide;

2-Dimethylamino-4-phenylpyrimidine-5-carboxylic acid (2-hydroxy-2-[3-[pyridin-3-carbonyl)amino]phenyl]ethyl)methyl amide;

2-Dimethylamino-4-phenylpyrimidine-5-carboxylic acid (2-hydroxy-2-{3-[(pyridin-4-carbonyl)amino] phenyl}ethyl)methyl amide;

2-Dimethylamino-4-phenylpyrimidine-5-carboxylic acid {2-[3-(2,2-dimethylpropynyl amino)phenyl]-2-hydroxyethyl}methyl amide;

2-Dimethylamino-4-phenylpyrimidine-5-carboxylic acid {2-[3-(cyclopentanecarbonyl amino)phenyl]-2-hydroxyethyl}methyl amide;

2-Dimethylamino-4-phenylpyrimidine-5-carboxylic acid {2-hydroxy-2-[3-(3-chloro benzoylamino)phenyl] ethyl}methyl amide;

2-Dimethylamino-4-phenylpyrimidine-5-carboxylic acid {2-[3-(3-tert-butylureido) phenyl]-2-hydroxyethyl}methyl amide;

2-(Benzylmethylamino)-4-phenylpyrimidine-5-carboxylic acid [2-hydroxy-2-(4-hydroxy-phenyl)ethyl]methyl amide;

2-(Benzylmethylamino)-4-phenylpyrimidine-5-carboxylic acid [2-hydroxy-2-(3-fluoro phenyl)ethyl]methyl amide;

2-(Benzylmethylamino)-4-phenylpyrimidine-5-carboxylic acid [2-hydroxy-2-(4-fluoro phenyl)ethyl]methyl amide;

2-(Benzylmethylamino)$_4$-phenylpyrimidine-5-carboxylic acid [2-hydroxy$_2$-(3-methoxy-phenyl)ethyl]methyl amide;

2-(Benzylmethylamino)-4-phenylpyrimidine-5-carboxylic acid [2-hydroxy-2-(4-methoxy-phenyl)ethyl]methyl amide;

2-(Benzylmethylamino)-4-phenylpyrimidine-5-carboxylic acid (2-phenyl-2-hydroxyethyl)-methyl amide;

2-(Benzylmethylamino)-4-phenylpyrimidine-5-carboxylic acid [2-(3-aminophenyl)-2-hydroxyethyl]methyl amide;

2-Benzylamino-4-phenylpyrimidine-5-carboxylic acid [2-(3,4-dihydroxyphenyl)-2-hydroxyethyl]methyl amide;

2-Dimethylamino-4-phenylpyrimidine-5-carboxylic acid [2-(3-benzyloxyphenyl)-2-fluoroethyl]methyl amide;

(±) Anti-[2-(benzylmethylamino)-4-phenylpyrimidin-5-yl]-[2-(hydroxyphenylmethyl)-piperidin-1-yl]methanone;

(±) Anti-[2-(benzylmethylamino)-4-phenylpyrimidin-5-yl]-{2-[hydroxy-(3-methoxyphenyl)methyl]piperidin-1-yl}methanone;

(±) Anti-[2-(benzylmethylamino)-4-phenylpyrimidin-5-yl]-{2-[hydroxy-(3-hydroxyphenyl)methyl]piperidin-1-yl}methanone;

(±) Anti-[2-(benzylmethylamino)-4-phenylpyrimidin-5-yl]-{2-[(3-fluorophenyl) hydroxymethyl]piperidin-1-yl}methanone;

(±) Anti-[2-(benzylmethylamino)-4-phenylpyrimidin-5-yl]-[2-(hydroxypyridin-3-yl-methyl)piperidin-1-yl]methanone;

(±) Anti-[2-(Benzylmethylamino)-4-(2-chlorophenyl)pyrimidin-5-yl]-[2-(hydroxyphenyl-methyl)piperidin-1-yl]methanone (±) Anti-[2-(benzylmethylamino)-4-phenylpyrimidin-5-yl]-[2-(hydroxypyridin-2-ylmethyl)piperidin-1-yl]methanone 2-(Benzylmethylamino)-4-(2-bromophenyl)pyrimidine-5-carboxylic acid [2-(3,4-dihydroxyphenyl)-2-hydroxyethyl]methyl amide 2-(Benzylmethylamino)-4-(2-bromophenyl)pyrimidine-5-carboxylic acid [2-hydroxy-2-(3-hydroxyphenyl)ethyl] methyl amide 2-(Benzylmethylamino)-4-(2-fluorophenyl)pyrimidine-5-carboxylic acid [2-(4-chloro-phenyl)-2-hydroxyethyl]methyl amide 2-(Benzylmethylamino)-4-phenylpyrimidine-5-carboxylic acid [2-(4-chlorophenyl)-2-hydroxyethyl]methyl amide 2-(Benzylmethylamino)-4-phenylpyrimidine-5-carboxylic acid (2-benzo[1,3]dioxol-5-yl-2-hydroxyethyl)methyl amide 2-(Benzylmethylamino)-4-(2-chlorophenyl)pyrimidine-5-carboxylic acid [2-(3,4-dihydroxyphenyl-2-hydroxyethyl] methyl amide 2-(Benzylmethylamino)-4-phenylpyrimidine-5-carboxylic acid [2-(4-cyanophenyl)-2-hydroxyethyl)methyl amide 4-(2-Chlorophenyl)-2-dimethylaminopyrimidine-5-carboxylic acid (2-hydroxy-2-(3-[(pyridine-4-carbonyl)amino]phenyl]ethyl)methyl amide 2-(Ethyl-pyridin-3-ylmethyl-amino)-4-(2-fluorophenyl)pyrimidine-5-carboxylic acid [2-hydroxy-2-(3-hydroxyphenyl)ethyl]methyl amide (±) Anti-[2-(benzylmethylamino)-4-phenylpyrimidin-5-yl]-{2-[(4-fluorophenyl)-hydroxymethyl]piperidin-1-yl}methanone (±) Anti-[2-(benzylmethylamino)-4-phenylpyrimidin-5-yl]-[2-hydroxy-p-tolyl-methyl)piperidin-1-yl]methanone (±) Anti-[2-(hydroxyphenylmethyl)piperidin-1-yl]-[2-(3-methoxybenzylamino)-4-phenylpyrimidin-5-yl]methanone (±) Anti-[2-(benzylmethylamino)-4-phenylpyrimidin-5-yl]-{2-[(3-chlorophenyl)-hydroxymethyl]piperidin-1-yl}methanone (±) Anti-{2-[(4-chlorobenzyl)methylamino]-4-phenylpyrimidin-5-yl}-[2-(hydroxy-phenylmethyl)piperidin-1-yl]methanone (±) Anti-[2-(benzylmethylamino)-4-phenylpyrimidin-5-yl]-[2-(hydroxy-m-tolyl-methyl)piperidin-1-yl]methanone (±) Anti-{2-[(4-fluorobenzyl)methylamino]-4-phenylpyrimidin-5-yl}-[2-(hydroxy-phenylmethyl)piperidin-1-yl]methanone (±) Anti-[2-(benzylmethylamino)-4-phenylpyrimidin-5-yl]-[2-(hydroxy-o-tolyl-methyl)piperidin-1-yl]methanone (±) Anti-[2-(benzylmethylamino)-4-phenylpyrimidin-5-yl]-{2-[(2-fluorophenyl)-hydroxymethyl]piperidin-1-yl}methanone (±) Anti-[2-(benzylmethylamino)-4-phenylpyrimidin-5-yl]-{2-[hydroxy-(4-methoxy-phenyl)methyl]piperidin-1-yl}methanone (±) Anti-[2-(4-fluorobenzylamine)-4-phenylpyrimidin-5-yl]-[2-(hydroxy-phenylmethyl)piperidin-1-yl]methanone (±) Anti-[2-(benzylmethylamino)-4-phenylpyrimidin-5-yl]-{2-[(3-chloro-4-fluorophenyl)hydroxymethyl]piperidin-1-yl}methanone (±) Anti-[2-(benzylmethylamino)-4-phenylpyrimidin-5-yl]-{2-[(3,4-difluorophenyl)-hydroxymethyl]piperidin-1-yl}methanone (±) Anti-[2-(3-chlorobenzylamino)-4-phenylpyrimidin-5-yl]-[2-(hydroxy-phenylmethyl)piperidin-1-yl]methanone (±) Anti-[2-(benzylmethylamino)-4-(2-chlorophenyl)-pyrimidin-5-yl]-[2-(hydroxy-phenylmethyl)piperidin-1-yl] methanone (±) Anti-[2-(benzylmethylamino)-4-phenylpyrimidin-5-yl]-[2-(hydroxypyridin-4-yl-methyl)piperidin-1-yl]methanone (±) Anti-[2-(benzylmethylamino)-4-(2-fluorophenyl)pyrimidin-5-yl]-[2-(hydroxy-phenylmethyl)piperidin-1-yl] methanone (±) Anti-{2-[(3-chlorobenzyl)methylamino]-4-phenylpyrimidin-5-yl}-[2-(hydroxy-phenylmethyl)piperidin-1-yl] methanone (±) Anti-[2-(benzylmethylamino)-4-phenylpyrimidin-5-yl]-{2-[(2-chlorophenyl)-hydroxymethyl]piperidin-1-yl}methanone (±) Anti-[2-(benzylmethylamino)-4-phenylpyridin-5-yl][2-(hydroxy-thiophen-3-yl-methyl)piperidin-1-yl]methanone (±) Anti-[2-(3-chloro-4-fluorobenzylamino)-4-phenylpyrimidin-5-yl]-[2-(hydroxy-phenylmethyl)piperidin-1-yl] methanone (±) Anti-{2-[(3-chloro-4-fluorobenzyl)methylamino]-4-phenylpyrimidin-5-yl}-[2-(hydroxyphenylmethyl)-piperidin-1-yl]methanone (±) Anti-[2-(benzylmethylamino)-4-(4-chlorophenyl)pyrimidin-5-yl]-[2-(hydroxy-phenylmethyl)piperidin-1-yl] methanone (±) Anti-[2-(3-chloro-4-fluorobenzylamino)-4-phenylpyrimidin-5-yl]-[2-(hydroxy-thiophen-3-yl-methyl)piperidin-1-yl]methanone.

$IC_{50}$ values of the compounds of the general formula (I) are usually smaller than 1000 nM, the favourable compounds exhibit $IC_{50}$ values smaller than 100 nM. For demonstration herebelow we give $IC_{50}$ values of some of our compounds of the general formula (I):

2-(Benzylmethylamino)-4-(2-methylphenyl)pyrimidine-5-carboxylic acid [2-hydroxy-2-(3-hydroxyphenyl)ethyl] methylamide Orex-1 $IC_{5-22}$ nM, Orex-2 $IC_{50}$ 5800 nM 2,2-Dimethylpropionic acid 3-{2-[(2-dimethylamino-4-(2-chlorophenyl)pyrimidine-5-carbonyl)methylamino]1-hydroxyethyl}phenyl ester Orex-1 $IC_{50}$ 30 nM, Orex-2 $IC_{50}$ 2900 nM 2-Dimethylamino-4-phenylpyrimidine-5-carboxylic acid [2-(3-benzyloxyphenyl)-2-hydroxyethyl]methylamide Orex-1 $IC_{50}$ 30 nM, Orex-2 $IC_{50}$ 3600 nM 4-Phenyl-2-[(pyridin-2-ylmethyl)amino]pyrimidin-5-carboxylic acid (2-hydroxy-1-methyl-2-phenylethyl)methylamide Orex-1 $IC_{50}$ 12 nM, Orex-2 $IC_{50}$ 5400 nM 2-Dimethylamino-4-phenylpyrimidin-5-carboxylic acid {2-hydroxy-2-[3-(2-methoxy-benzoylamino)phenyl]ethyl}methylamide Orex-1 $IC_{50}$ 15 nM, Orex-2 $IC_{50}$ 320 nM (±) Anti-[2-(benzylmethylamino)-4-phenylpyrimidin-5-yl]-[2-(hydroxyphenylmethyl) piperidin-1-yl]methanone Orex-1 $IC_{50}$ 11 nM, Orex-2 $IC_{50}$ 6700 nM

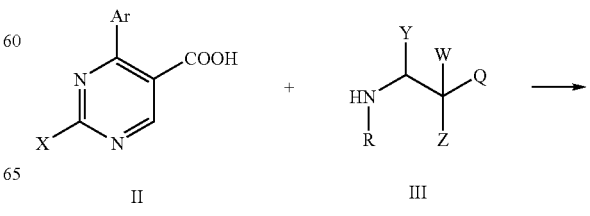

Figure 1.

-continued

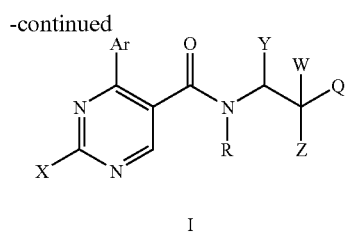

I

FIG. 1. shows the method of preparation of the compounds of the general formula (I). According to one of the processes die acid of the general formula (II)—wherein the meaning of Ar and X is as defined above—is transformed with an acid halogenide forming reagents, preferably with thionyl chloride, into the acid chloride, which is then reacted with the amine of the general formula (III)—wherein in the formula the meaning of R, Y, Z, W, Q is as defined above—in an inert solvent, (e.g. in dichloromethane or chloroform) in the presence of a base (e.g. triethylamine) or in pyridine, at room temperature or at reflux temperature.

According to the other process the acid of the general formula (II)—wherein the meaning of Ar and X is as defined above—is reacted with the amine of the general formula (III)

wherein in the formula the meaning of R, Y, Z, W, Q is as defined above—in the presence of an activating agent. The activating agent may be benzotriazol-1-yloxy-tris (pyrrolidino)phosphonium hexafluorophosphate (PyBOP) or benzotriazol-1-yloxy-tris-(dimethylamino) phosphonium hexafluorophosphate (BOP) or 4-(4,6-dimethoxy-1,3,5-triazin-2-yl)-4-methylmorpholinium chloride (DMTMM) or 1-etyl-3-(3'-dimethylaminopropyl)carbodiimide hydrochloride (EDC) with 1-hydroxybenzotriazole or 2,3,4,5,6-pentafluorophenol. The reaction is carried out in an inert sovent (e.g. in N,N-dimethylformamide, dichloromethane, tetrahydrofuran, dioxane, acetonitrile or in the mixture of thereof) at room temperature or under reflux conditions. The compounds of the general formula (I) can also be prepared by using tetrafluorophenol bound to a solid phase polymeric support (for instance polystyrol-divinylbenzene-resin (J. M. Salvino et al. J. Comb. Chem. 2000, 2, 691) to activate the carboxylic acid.

Functional groups of the compounds of the general formula (I) can be transformed into other functional groups (for example the substituents Q, $R^2$, $R^3$, $R^4$, Z, W can be transformed into other Q, $R^2$, $R^3$, $R^4$, Z, W substituents). The carboxylic acids of the general formula (II)—wherein the meaning of Ar and X is as defined above—are in part known from the literature or they can be prepared by methods known from the literature (FIG. 2).

The β-keto-esters of the general formula (IV) are available from the market or they can be synthesized by known methods (Gilman H. et al., J. Am. Chem. Soc. 1948, 70, 2755, Sicker D. et al., Coll. Czech. Chem. Commun. 1988, 53, 839-850, Wierenga W. et al., J. Org. Chem. 1979, 44, 310-311). Reaction of the compounds of the general formula (IV) with N,N-dimethylformamide dimethyl acetal can be performed in the presence of solvent (for example in toluene at 60° C.; Herrero M. T. et al., Tetrahedron 2002, 58, 8581), or without solvent at 100-120° C., or in microwave reactor (10-30 W).

The enaminoesters of the general formula (V) with N—C—N dinucleofils, for example with guanidine (VI), amidines (VI), S-methylisothiocarbamide (VII), O-methylisocarbamide (VIII) can be transformed into 2-substituted-pyrimidinecarboxylic acid esters (IX, X, XI) Breaux E. J. et al., J. Heterocyclic Chem. 1981, 18, 183, WO 00/73279). Ring closure can be effected in the presence of base (sodium ethylate or sodium hydrogen carbonate) in ethanol, N,N-dimethylformamide or N-methylpyrrolidinone, at room temperature or at elevated temperature (80-100° C.). The 2-methylsulphonyl group of the compound of the general formula (X) can be oxidized with an oxidating agent (e.g. with 3-chloro-perbenzoic acid) into 2-methylsulphonyl group. The compounds of the general formula (XII) by reacting with a primary or secondary amine, in the presence of a solvent (e.g. in dioxane) can be transformed into the esters of the general formula (IX)—where in the formula X represents a dialkylamino group, alkylamino group, arylamino group, arylalkylamino group, alkyl-arylalkylamino group, hetarylalkylamino group (for example hetarylmethylamino group), alkyl-hetarylalkylamino group (for example methyl-hetarylmethylamino group), amino group, 3,4-dihydro-1H-isoquinolin-2-yl group; the aryl group is a phenyl group optionally containing one or more substituents (e.g. halogen atom, $C_{1-4}$-alkyl croup, $C_{1-4}$-alkoxy group); the hetaryl group is a 5- or 6-membered heteroaromatic ring containing 1-3 heteroatoms (nitrogen, oxygen or sulphur atom) (for example 2-pyridyl, 3-pyridyl, 4-pyridyl, 2-thienyl, 3-thienyl group). The esters of the general formula (IX)—where in the formula X represents a dialkylamino group, alkylamino group, arylamino group, arylalkylamino group, alkyl-arylalkylamino group, hetarylalkylamino group (for example hetarylmethylamino group), alkyl-hetarylalkylamino group (for example methyl-hetarylmethylamino group), amino group, 3,4-dihydro-1H-isoquinolin-2-yl group; the aryl group is a phenyl group optionally containing one or more substituents (e.g. halogen atom, $C_{1-4}$-allyl group, $C_{1-4}$-alkoxy group); the hetaryl group is a 5- or 6-membered heteroaromatic ring containing 1-3 heteroatoms (nitrogen, oxygen or sulphur atom) (for example 2-pyridyl, 3-pyridyl, 4-pyridyl, 2-thienyl, 3-thienyl group) can also be prepared by reacting the ester of the formula (XI) with a primary or secondary amine at elevated temperature (up to 170° C.) in the presence of a solvent or without solvent.

The esters of the general formula (IX)—where in the formula the meanings of Ar and X are as defined above—can be hydrolyzed under acidic or basic conditions into the acids of the general formula (II)—where in the formula the meaning of Ar and X is as defined above. As for acid e.g. hydrochloric acid, as for base e.g. sodium hydroxide, potassium hydroxide, sodium carbonate, potassium carbonate can be used in aqueous ethanol or aqueous methanol.

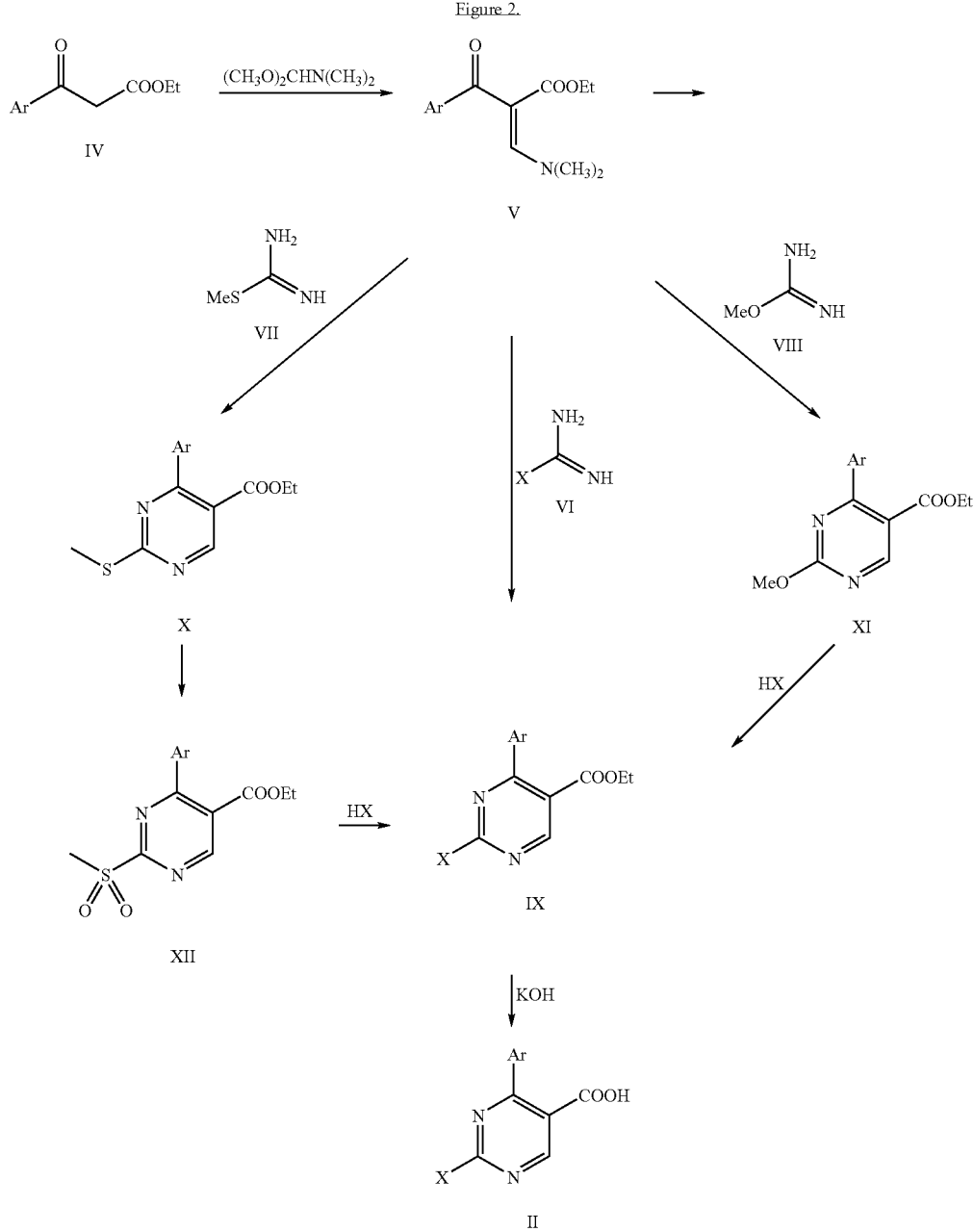

Figure 2.

The acids of the general formula (II) can also be prepared by a novel method, as shown in FIG. 3. The compounds of the general formula (XIII) can be synthesized by known methods, by the base-catalysed condensation of amidines with diethyl ethoxymethylenemalonate. The resulting compounds give with phosphoryl chloride the chloro-compounds of the general formula (XIV) (Dostert P. et al., Eur. J. Med. Chem. Chim. Ther. 1982, 17, 437-444). In the novel process the chloro-compounds of the general formula (XIV) are transformed with aryl-boronic acids in dimethoxyethane, in the presence of tetrakis(triphenylphosphino)palladium catalyst into the compounds of the general formula (IX)—where in the formula Ar and X have the meanings as defined above.

The esters of the general formula (DC) are hydrolyzed under acidic or basic conditions, preferably in the presence of base.

Figure 3.

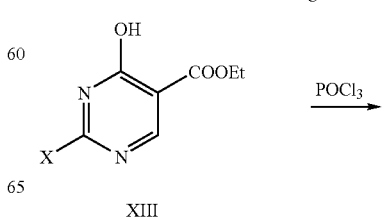

XIII

-continued

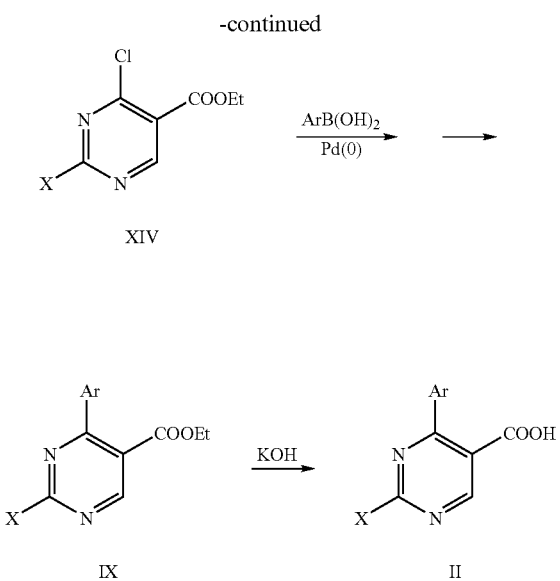

The amines of the general formula (III)—where in the formula the meanings of R, Y, Z, W and Q are defined above—can be purchased on the market or can be synthesized by methods known in the literature. The compounds of the general formula (III) wherein R and Y, together with the nitrogen atom and the carbon atom to which they are attached, form a ring, i.e.: compounds (IIIa), can be prepared according to FIG. 4. The compounds of the general formula (XV), wherein the formula A represents a CH, NH, N-Boc, N—($C_{1-4}$)-alkyl group, n=1, 2, 3 and PG means a protecting group (e.g. a t-butyloxycarbonyl-, trifluoroacetyl-, benzyloxycarbonyl-group, or an other protecting group, see Protective Groups in Organic Synthesis, 2nd Edition, John Wiley & Sons, Inc., New York)—can be purchased on the market or can be synthesized by methods known in the literature. (Beak P. et al., J. Org. Chem. 1993, 58, 1109-1117, Brosius A. D. et al., J. Am. Chem. Soc. 1999, 121, 700-709, WO 98/33793, WO 01/00213). The compounds of the general formula (XVI) are those—wherein in the formula M represents a metal atom (e.g. lithium or magnesium atom), B represents a CH group, or a nitrogen atom, $R^5$ means hydrogen atom, hydroxyl group, halogen atom, $C_{1-4}$-alkyl group, $C_{1-4}$-alkoxy group. The substituent $R^5$ may take o-, m-, or p-position. The reaction of compounds (XV) with compounds (XVI) is performed in an inert solvent, for example in tetrahydrofuran or in ether, at low temperature (between 0° C. and −78° C.).

Figure 4.

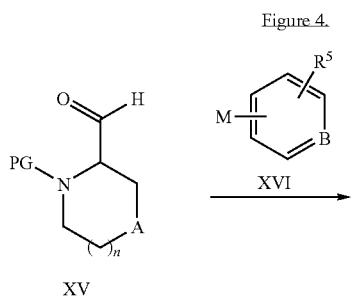

The protecting group (e.g. the t-butyloxycarbonyl-, trifluoroacetyl-, benzyloxycarbonyl group) of the compounds of the general formula (XVII) can be removed under acidic conditions (for example with trifluoroacetic acid in dichloromethane, with hydrochloric acid in dioxane or in dichloromethane), under basic conditions (for example with sodium hydroxide in aqueous methanol) or by catalytic hydrogenolysis (e.g. with palladium-on-charcoal catalyst in alcohol or in ethyl acetate).

The pharmaceutically acceptable salts of the compounds of the general formula (I) can be prepared by reacting the bases with the appropriate acids. By solvates of the compounds of the general formula (I) we also mean the hydrates.

The compounds of the general formula (I), as well as their pharmaceutically acceptable derivatives can be used for the treatment of diseases where human orexin receptors play a role, and for the treatment of which orexin receptor antagonists are needed.

The orexin receptor antagonistic compounds of the general formula (I), and their pharmaceutically acceptable derivatives may be appropriate for the treatment of obesity and type-II diabetes (non-insulin dependent diabetes), furthermore for the treatment of sleeping disorders, narcolepsy, insomnia, jet-lag syndrome, for the treatment of sleeping disorders connected to neurological disorders, depression, anxiety, behavioral disorders, sexual disorders, neuropathic pain, pains connected to infections (like HIV), phantome pains, postoperative pains. The compounds of the general formula (I), and their pharmaceutically acceptable derivatives may be used for the treatment of stroke, heart- and lung diseases.

The compounds of the general formula (I), as well as their pharmaceutically acceptable derivatives can be used for the treatment and prevention of diseases where human orexin receptor antagonists are needed for the treatment. In the course of the therapy the compounds according to the invention are used in the form of pharmaceutical composition. The pharmaceutical compositions contain the compounds of the general formula (I) or their derivatives together with pharmaceutically acceptable carriers and excipients.

The compounds of the general formula (I), and their pharmaceutically acceptable derivatives can be administered by any of the traditional routes, e.g. by oral, parenteral, sublingual, nasal, rectal, or transdermal routes.

The compounds of the general formula (I) and their pharmaceutically acceptable derivatives may be administered orally, in the forms of solid or liquid formulations, as for instance syrups, suspensions, emulsions, tablets or capsules.

Liquid formulations contain the active component beside an appropriate liquid vehicle (e.g. water, ethanol, glycerine, polyethyleneglycole, oil) in the form of a solution or suspension. They may also contain colouring and odour agents.

Tablets may contain the usual additives, e.g. magnesium stearate, starch, lactose, sucrose and cellulose.

Hard and soft gelatine capsules can be prepared by the standard operations.

Parenteral formulations contain the active ingredient in the form of a solution or suspension, prepared with a sterile aqueous carrier or with an appropriate oil, as for instance polyethylene glycol, polyvinylpyrrolidone, sesame oil or lecitine.

For nasal application aerosols, drops, gels or powders can be applied. Aerosols contain the active ingredient in the form of an aqueous or non-aqueous solution or suspension, in a closed container, in single or multiple doses.

For rectal application suppositories may be used which contain the usual excipients (e.g. cacao-butter or coconut-butter).

For transdermal application ointments, gels or dermal patches may be used.

The doses of the compounds of the general formula (I) and their pharmaceutically acceptable derivatives used for the treatment or prevention of the above diseases depend on the nature of the disease and in general, a single dose is between 0.05 mg and 1000 mg and the daily dose is between 0.01 mg/kg and 100 mg/kg.

In the above dose regimens the compounds of the general formula (I) are not expected to cause toxic side effects.

CHEMICAL EXAMPLES

Example 1

2-Dimethylamino-4-phenylpyrimidine-5-carboxylic acid [2-hydroxy-2-(3-hydroxy-phenyl)ethyl]methyl amide (L-isomer)

Method A

2-Dimethylamino-4-phenylpyrimidine-5-carboxylic acid (1.22 g, 5 mmol) is dissolved in tetrahydrofuran (60 ml). After 5 minutes of stirring to the solution are added: L-phenylephrine hydrochloride (1.22 g, 6 mmol) in tetrahydrofuran (50 ml), after another 5 minutes of stirring the N-methylmorpholine (1.21 g, 12 mmol) and after 2 minutes of stirring the 4-(4,6-dimethoxy-1,3,5-triazin-2-yl)-4-methylmorpholinium chloride (1.66 g, 6 mmol). The reaction mixture is stirred for 2 hours at room temperature, then heated at reflux temperature for 2 hours. The solvent is removed in vacuum. To the residue water (50 ml) is added, and the mixture is extracted with chloroform (75 ml), the extract is washed with 10% sodium carbonate solution (35 ml), with water (35 ml), dried over sodium sulphate and evaporated. The residue is chromatographed on silicagel using chloroform-methanol 100/1-100/5 mixture eluent. 0.36 g of the title compound is obtained, m.p.: 79-81° C.

According to the process described in Example 1. are prepared the compounds of Tables 1. and 2.

TABLE 1

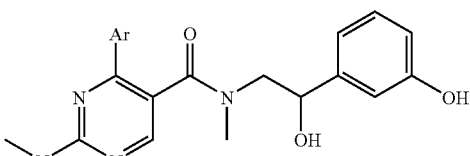

I

X = Me$_2$N, R = Me, Y = H, Z = OH, W = H,
Q = m-phenylene, R$^2$ = H, R$^3$ = OH, R$^4$ = H

| Example | Ar | Mp (° C.) |
|---|---|---|
| Example 1. | (phenyl) | 79-81<br>White crystals |
| Example 2. | (4-pyridyl) | 1 mol H$_2$O<br>92-98<br>Pale yellow crystals |
| Example 3. | (4-pyridyl) | 215-216<br>(EtOH)<br>White crystals |
| Example 4. | (3-pyridyl) | 180-181<br>White crystals |
| Example 5. | (2-pyridyl) | 0.5 mol H$_2$O<br>95-97<br>Yellow crystals |
| Example 6. | (phenyl) | 0.5 mol H$_2$O<br>80-81<br>White crystals |
| Example 7. | (2,5-dichloro-4-fluorophenyl) | 1 mol H$_2$O<br>115-117<br>White crystals |

TABLE 1-continued

I

X = Me₂N, R = Me, Y = H, Z = OH, W = H,
Q = m-phenylene, $R^2$ = H, $R^3$ = OH, $R^4$ = H

| Example | Ar | Mp (° C.) |
|---|---|---|
| Example 8. | 3,4-dichlorophenyl | 0.5 mol H₂O<br>99-103<br>White crystals |
| Example 9. | 3,4-dimethoxyphenyl | 1 mol H₂O<br>85-90<br>Greyish-white crystals |
| Example 10. | 4-chlorophenyl | 1 mol H₂O<br>1 mol DMF<br>HCl salt 96<br>Pale-yellow crystals |
| Example 11. | 2-chlorophenyl | 0.5 mol H₂O<br>149<br>White crystals |
| Example 12. | 2-fluorophenyl | 1 mol H₂O<br>71<br>White crystals |
| Example 13. | 2-methoxyphenyl | 1.5 mol H₂O<br>122<br>White crystals |
| Example 14. | 2-iodophenyl | 0.5 mol H₂O<br>97-98<br>White crystals |

TABLE 2

I

Ar = Phenyl, X = Me₂N, Y = H, Z = OH, W = H,
Q = m-phenylene, $R^2$ = H, $R^3$ = OH, $R^4$ = H

| | R | Mp (° C.) |
|---|---|---|
| Example 15. | H | 0.5 mol H₂O<br>132-133<br>White crystals |
| Example 16. | Et | 1.5 mol H₂O<br>84-88<br>White crystals |

Example 17

4-Phenyl-2-[(thiophen-2-ylmethyl)amino]pyrimidine-5-carboxylic acid [2-hydroxy-2-(3-hydroxyphenyl)ethyl]methylamide (I)

a) Ethyl 4-phenyl-2-methylsulplanylpyrimidine-5-carboxylate

The mixture of ethyl benzoylacetate (9.61 g, 50 mmol) and N,N-dimethylformamide dimethyl acetal (6.55 g, 55 mmol) was heated in microwave reactor for 10 minutes (30 W, →130° C.). To the resulting orange coloured oil ethanol (100 ml), S-methylisothiuronium sulphate (6.96 g, 25 mmol) and sodium ethylate (3.40 g, 50 mmol) were added and the reaction mixture was boiled for 2.5 hours. Ethanol was removed in vacuum, to the residue water (200 ml) was added. The mixture was extracted with ethyl acetate (3×100 ml), the organic phase was dried over sodium sulphate and evaporated. 11.41 g (83%) yellow oil was obtained. [M+H]⁺ 275.

b) Ethyl 4-phenyl-2-methanesulphonylpyrimidine-5-carboxylate

Ethyl 4-phenyl-2-methylsulphanylpyrimidine-5-carboxylate (6.4 g, 23.3 mmol) was dissolved in dichloromethane (250 ml) and under stirring at 0-5° C., in a period of 15 minutes, 70% 3-chloroperbenzoic acid (14.36 g, 58.2 mmol) was added to the mixture. The reaction mixture was stirred at room temperature for 4 hours; extracted with saturated sodium hydrogencarbonate solution (2×250 ml), then with water (2×250 ml), dried over sodium sulphate and evaporated. The residue was crystallized with diisopropyl ether (15 ml). 4.57 g (64%) of the title ester was obtained as white crystals, mp.: 85-86° C.; [M+H]$^+$ 307 c) Ethyl 4-phenyl-2-[(thiophen-2-ylmethyl)amino]pyrimidine-5-carboxylate

The mixture of ethyl 4-phenyl-2-methanesulphonylpyrimidine-5-carboxylate (2.30 g, 7.5 mmol), 2-thienylmethylamine (2.12 g, 18.75 mmol) and dioxane (30 ml) were stirred at room temperature for 16 hours, the solvent was removed in vacuum. To the residue ethanol (10 ml) was added, the resulting crystals were filtered off in vacuum, washed with ethanol (5 ml) to obtain 1.99 g (78%) of the title ester in the form of white crystals, m.p.: 123-124° C.; [M+H]$^+$ 340 d) 4-Phenyl-2-[(thiophen-2-ylmethyl)amino]pyrimidine-5-carboxylic acid

Ethyl 4-phenyl-2-[(thiophen-2-ylmethyl)amino]pyrimidine-5-carboxylate (1.70 g, 5 mmol) was dissolved in ethanol (10 ml). To the solution potassium hydroxide (0.56 g, 10 mmol) dissolved in 10 ml of water was added and the mixture was refluxed for 3 hours. The solvent was distilled off in vacuum, the residue was dissolved in water (35 ml), acidified to pH=3 with 10% hydrochloric acid. The precipitated white crystals were filtered off, washed with water (2×20 ml) and dried. 1.52 g (92%) of the title acid was obtained, m.p.: 212-213° C.; [M+H]$^+$ 312.

e) 4-Phenyl-2-[(thiophen-2-ylmethyl)amino]pyrimidine-5-carboxylic acid [2-hydroxy-2-(3-hydroxyphenyl)ethyl]methylamide (I)

Method B
4-Phenyl-2-[(thiophen-2-ylmethyl)amino]pyrimidine-5-carboxylic acid (0.49 g, 1.5 mmol) was dissolved in dioxane (35 ml) and to the solution benzotriazol-1-yloxy-tris pyrrolidino)phosphonium hexafluorophosphate (PyBOP) (0.78 g, 1.5 mmol), D,L-phenylephrine hydrochloride (0.305 g, 1.5 mmol) and ethyldiisopropylamine (0.53 g, 4.1 mmol) were added. The solution was stirred at room temperature for 16 hours, evaporated in vacuum, to the residue water (50 ml) was added, the mixture was extracted with dichloromethane (50 ml), the organic phase was washed with 10% sodium hydrogencarbonate solution (15 ml), then with water (3×25 ml), dried over sodium sulphate, evaporated, chromatographed on silicagel using ethyl acetate eluent. 0.51 g (74%) of the title amide was obtained in the form of white crystals, containing 1 mol of water as solvate. M.p.: 85-87° C.; [M+H]$^+$ 461.

Example 28

2-(Benzylmethylamino)-4-(2-chlorophenyl)pyrimidine-5-carboxylic acid [2-hydroxy-2-(3-hydroxyphenyl)ethyl]methylamide (L-isomer)(I)

a) 2-(Benzylmethylamino)-4-(2-chlorophenyl)pyrimidine-5-carboxylic acid (II)

Ar=2-Cl—C$_6$H$_4$, X=Me(C$_6$H$_5$CH$_2$)N

Tetrakis(triphenylphosphino)palladium catalyst (0.25 g, 0.22 mmol) is dissolved under nitrogen atmosphere in dimethoxyethane (20 ml) and to this solution the solution of ethyl-2-(benzylmethylamino)-4-chloropyrimidine-5-carboxylate (2.75 g, 9.0 mmol) in dimethoxyethane (20 ml) is added. To the resulting mixture 2-chlorophenylboronic acid (1.55 g, 9.9 mmol), sodium carbonate (2.43 g, 23 mmol), dimethoxyethane (20 ml) and water (40 ml) are added. The mixture is stirred at 100° C. for 16 hours, cooled to room temperature and after the addition of dichloroethane (100 ml) it is washed with water (100 ml), dried over sodium sulphate and evaporated. The palladium impurities precipitating on the addition of ether, are filtered off, the filtrate is evaporated. 3.13 g of the ester is obtained which is hydrolyzed to the acid without further purification. To the solution of the ester in 95% alcohol (25 ml) the solution of potassium hydroxide (1.12 g, 20.0 mmol) in 95% alcohol (25 ml) is added. The mixture is heated at 80° C. for 3 hours, evaporated in vacuum. To the residue water (50 ml) and then 10% hydrochloric acid is added until pH=5, the mixture is extracted with dichloromethane (50 ml), the organic phase is dried over sodium sulphate and evaporated. 2.77 g (87%) white coloured title acid is obtained, m.p.: 92° C.; purity by HPLC-MS: 95%.

b) 2-(Benzylmethylamino)-4-(2-chlorophenyl)pyrimidine-5-carboxylic acid [2-hydroxy-2-(3-hydroxyphenyl)ethyl]methylamide (L-isomer) (I)

Method B
The material is prepared according to the method described in Example 17. starting from 2-(Benzylmethylamino)-4-(2-chlorophenyl)pyrimidine-5-carboxylic acid and L-phenylephrine hydrochloride. M.p.: 139° C.

TABLE 3
R = Me, Y = H, Z = OH, W = H, Q = m-Phenylene,
R² = H, R³ = OH, R⁴ = H
| | Method | Ar | X | Mp (° C.) |
|---|---|---|---|---|
| Example 17. | B | 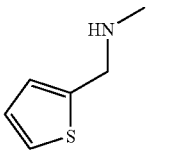 | 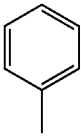 | 1 mol H₂O<br>85-87<br>White crystals |
| Example 18. | A | 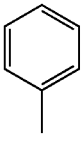 | Me | 1 mol H₂O<br>69-70<br>White crystals |
| Example 19. | B | 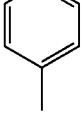 | MeS | 1 mol DMF<br>Oil |
| Example 20. | B | 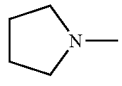 | 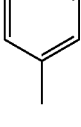 | 115<br>White crystals |
| Example 21. | A | 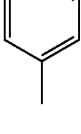 | —NH₂ | 138-140<br>White crystals |
| Example 22. | B | 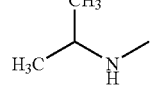 | 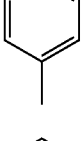 | 1 mol H₂O<br>89-92<br>White crystals |
| Example 23. | B | 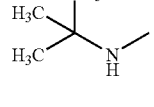 | 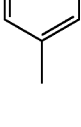 | 0.5 mol H₂O<br>98-102<br>White crystals |
| Example 24. | B | 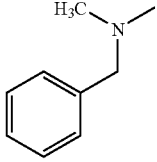 | | 0.5 mol H₂O<br>78-84<br>White crystals |

TABLE 3-continued
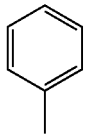
R = Me, Y = H, Z = OH, W = H, Q = m-Phenylene,
R² = H, R³ = OH, R⁴ = H
| | Method | Ar | X | Mp (° C.) |
|---|---|---|---|---|
| Example 25. | B | 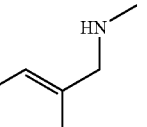 | 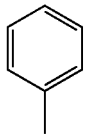 | 1 mol H₂O<br>97-100<br>White foam |
| Example 26. | B | 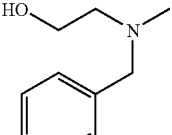 | 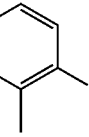 | 1 mol H₂O<br>88-91<br>White crystals |
| Example 27. | B | 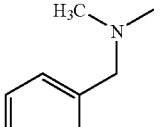 | 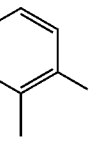 | 1 mol H₂O<br>123<br>White crystals |
| Example 28. | B | 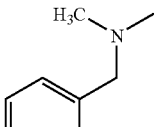 | 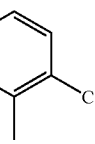 | 139<br>White crystals |
| Example 29. | B | 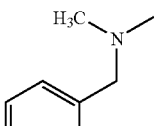 | 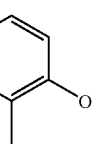 | 104<br>Pale-yellow crystals |
| Example 30. | B | 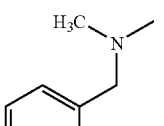 |  | 137<br>White crystals |
| Example 31. | B | 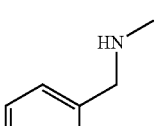 | | 0.5 mol H₂O<br>96-98<br>White crystals |

TABLE 3-continued
R = Me, Y = H, Z = OH, W = H, Q = m-Phenylene,
R² = H, R³ = OH, R⁴ = H
|  | Method | Ar | X | Mp (° C.) |
|---|---|---|---|---|
| Example 32. | B | 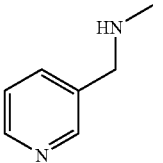 |  | 1 mol H₂O<br>89-92<br>White crystals |
| Example 33. | B | 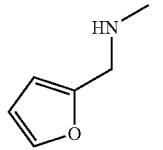 |  | 1 mol H₂O<br>73-76<br>pale-yellow crystals |
| Example 34. | B | 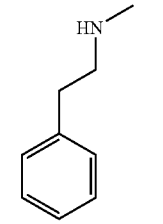 | 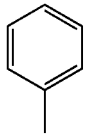 | 1 mol H₂O<br>84-86<br>White crystals |
| Example 35. | B | 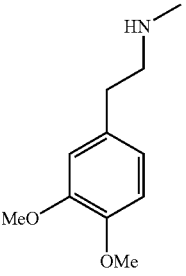 | 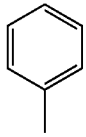 | 2 mol H₂O<br>90-98<br>White foam |
| Example 36. | B | 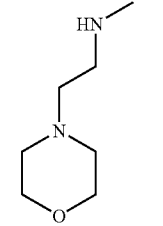 | 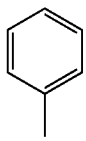 | 0.5 mol H₂O<br>98-102<br>White foam |
| Example 37. | B | (phenyl with Me) | 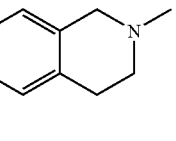 | 1 mol H₂O<br>98-101<br>White crystals |

TABLE 3-continued

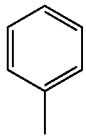

R = Me, Y = H, Z = OH, W = H, Q = m-Phenylene,
$R^2 = H, R^3 = OH, R^4 = H$

| | Method | Ar | X | Mp (° C.) |
|---|---|---|---|---|
| Example 38. | B | 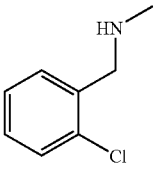 | 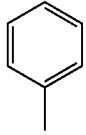 | 98-102<br>White crystals |
| Example 39. | B | 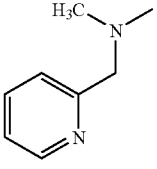 | 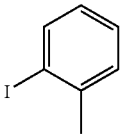 | 1 mol H$_2$O<br>83-94<br>White crystals |
| Example 40. | B | 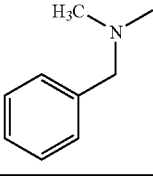 | 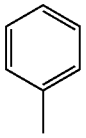 | 0.5 mol H$_2$O<br>91-92<br>Pale-yellow crystals |

Example 41

2,2-Dimethylpropionic acid 3-{2-[(2-dimethylamino-4-phenylpyrimidine-5-carbonyl) methylamino]-1-hydroxyethyl}phenyl ester (L-isomer)

The mixture of 2-dimethylamino-4-phenylpyrimidine-5-carboxylic acid [2-hydroxy-2-(3-hydroxyphenyl)ethyl]methylamide (L-isomer) (0.52 g, 1.32 mmol), pyvaloyl chloride (0.16 g, 1.32 mmol), triethylamine (0.145 g, 1.43 mmol) and dichloromethane (20 ml) is boiled under stirring for 4 hours. The reaction mixture is cooled to room temperature, dichloromethane (15 ml) is added to it, washed with water (3×25 ml), dried over sodium sulphate, evaporated and the residue is chromatographed on silica, using ethyl acetate as eluent. 0.36 g (57%) of white title compound is obtained, m.p.: 145-146° C.; [M+H]$^+$ 477.

The compounds of Table 4. are prepared according to the method described in Example 41.

TABLE 4

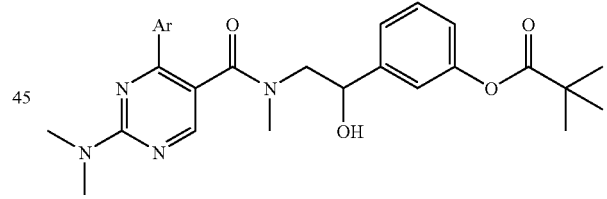

X = Me$_2$N, R = Me, Y = H, Z = OH, W = H,
Q = m-phenylene, $R^2$ = H, $R^3$ = (CH$_3$)$_3$CCOO, $R^4$ = H

| | Ar | Mp (° C.) |
|---|---|---|
| Example 41. | 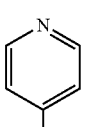 | 76-77<br>White crystals<br>145-146 |
| Example 42. | 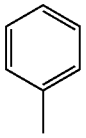 | 79-83<br>Pale-yellow crystals |

TABLE 4-continued

X = Me$_2$N, R = Me, Y = H, Z = OH, W = H,
Q = m-phenylene, R$^2$ = H, R$^3$ = (CH$_3$)$_3$CCOO, R$^4$ = H

| | Ar | Mp (° C.) |
|---|---|---|
| Example 43. | 3-pyridyl | 2 mol H$_2$O<br>116-118<br>Yellow crystals |
| Example 44. | 2-pyridyl | 1 mol H$_2$O<br>52-57<br>Yellow crystals |
| Example 45. | phenyl | 1.5 mol H$_2$O<br>123-124<br>White crystals |
| Example 46. | 3-thienyl | 72<br>Pale-yellow crystals |
| Example 47. | 2-thienyl | HCl-salt<br>127<br>Yellow crystals |
| Example 48. | 2-chlorophenyl | 70<br>White crystals |
| Example 49. | 3-chlorophenyl | 79<br>White crystals |
| Example 50. | 4-chlorophenyl | HCl-salt<br>120<br>Yellow crystals |
| Example 51. | 3-fluorophenyl | 76<br>White crystals |
| Example 52. | 4-fluorophenyl | 168<br>White crystals |
| Example 53. | 3,4-dimethoxyphenyl | 0.5 mol H$_2$O<br>0.5 mol CHCl$_3$<br>64-70<br>Grayish-white crystals |
| Example 54. | 4-methoxyphenyl | 84<br>White crystals |
| Example 55. | 3-methoxyphenyl | 76-77<br>White crystals |
| Example 56. | 3,4-methylenedioxyphenyl | 101<br>Pale-yellow crystals |

TABLE 4-continued

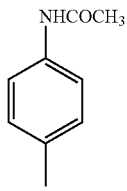

X = Me₂N, R = Me, Y = H, Z = OH, W = H,
Q = m-phenylene, R² = H, R³ = (CH₃)₃CCOO, R⁴ = H

| | Ar | Mp (° C.) |
|---|---|---|
| Example 57. | 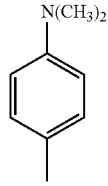 NHCOCH₃ | 1 mol H₂O<br>147<br>Pale-yellow crystals |
| Example 58. |  N(CH₃)₂ | 115<br>Pale-yellow crystals |

Example 59

2-Dimethylamino-4-(3,4-dichlorophenyl)pyrimidine-5-carboxylic acid [2-(3-benzyloxyphenyl)-2-hydroxyethyl]methylamide (I)

The mixture of 2-dimethylamino-4-(3,4-dichlorophenyl)pyrimidine-5-carboxylic acid [2-hydroxy-2-(3-hydroxyphenyl)ethyl]methylamide (0.92 g, 2 mmol), benzylbromide (1.71 g, 10 mmol), cesium carbonate (1.30 g, 4 mmol) and acetonitrile (25 ml) are boiled under stirring for 5 hours. The reaction mixture is evaporated in vacuum, dichloromethane (50 ml) is added to it, washed with water (3×50 ml), dried over sodium sulphate and evaporated. The residue is chromatographed on silicagel, using dichloromethane—methanol 100/1 mixture as eluent. 0.50 g (45.4%) of pale-yellow crystalline material is obtained, m.p.: 68-70° C.; [M+H]⁺ 551.

The compounds of Tables 5 and 6. are prepared according to the method described in Example 59.

TABLE 5

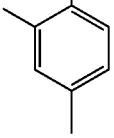

R = Me, Y = H, Z = OH, W = H, Q = m-phenylene,
R² = H, R³ = OCH₂Ph, R⁴ = H

| | Ar | X | Mp (° C.) |
|---|---|---|---|
| Example 59. | 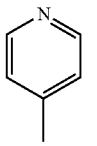 | Me₂N | 68-70<br>Pale-yellow crystals |
| Example 60. | 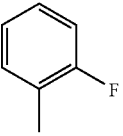 | Me₂N | 77<br>White crystals |
| Example 61. | 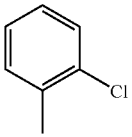 | Me₂N | 2 HCl-salt<br>1 mol H₂O<br>125<br>Yellow crystals |
| Example 62. | 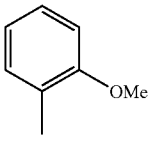 | Me₂N | HCl-salt<br>1.5 mol H₂O<br>142<br>Pale-yellow crystals |
| Example 63. | 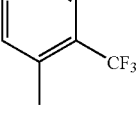 | Me₂N | HCl-salt<br>90<br>Pale-yellow crystals |
| Example 64. | 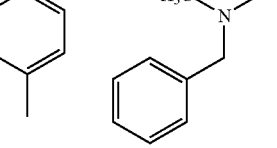 OMe | Me₂N | 0.5 mol H₂O<br>79<br>Pale-yellow crystals |
| Example 65. | CF₃ | Me₂N | 0.5 mol H₂O<br>77<br>White crystals |
| Example 66. | | H₃C–N–CH₂Ph | 0.2 mol H₂O<br>86<br>White crystals |

TABLE 5-continued

[Structure: pyrimidine with Ar, X substituents, carboxamide linked to N-methyl, CH(OH)CH2, m-phenylene with OCH2Ph]

R = Me, Y = H, Z = OH, W = H, Q = m-phenylene,
R² = H, R³ = OCH₂Ph, R⁴ = H

| | Ar | X | Mp (° C.) |
|---|---|---|---|
| Example 67. | phenyl (4-methylphenyl) | Me | [M + H]⁺ 454<br>White crystals |
| Example 68. | 2-chloro-methylphenyl | H₃C-N(benzyl)- | 77<br>White crystals |

TABLE 6

[Structure with Ar = 4-Pyridyl, pyrimidine-NMe₂, carboxamide-N-Me-CH(OH)-CH2-m-phenylene-R³]

Ar = 4-Pyridyl, X = Me₂N, Y = H, Z = OH,
W = H, Q = m-phenylene, R² = H, R⁴ = H

| | R³ | Mp (° C.) |
|---|---|---|
| Example 69. | H | 165<br>Yellow crystals |
| Example 70. | CH₃O | 1 mol H₂O<br>136<br>Yellow crystals |
| Example 71. | C₂H₅O | 2 HCl-salt<br>85-91<br>Yellow crystals |
| Example 72. | (CH₃)₂CHO | 2 HCl-salt<br>115<br>Yellow crystals |
| Example 73. | CH₃CONH | 2 HCl-salt<br>158<br>Yellow crystals |

Example 74

4-Phenyl-2-[(pyridin-2-ylmethyl)amino]pyrimidine-5-carboxylic acid (2-hydroxy-1-methyl-2-phenyl-ethyl)methylamide (I)

Method B

Starting from 4-phenyl-2-[(pyridin-2-ylmethyl)amino]pyrimidine-5-carboxylic acid (0.48 g, 1.5 mmol) and (1R,2S)-2-methylamino-1-phenyl-1-propanol [(−)-ephedrine] (0.25 g, 1.5 mmol) according to the method described in Example 17. the title amide 0.42 g (58%) is obtained as white crystalline material; m.p.: 82° C.; [M+H]⁺ 468.

The compounds of Table 7. are prepared according to the process described in Example 74.

TABLE 7

[Structure: Ar-pyrimidine(X)-carboxamide-N(Me)-CH(Me)-CH(OH)-phenyl]

R = Me, Y = Me, Z = OH, W = H, Q = Phenyl,
R² = H, R³ = H, R⁴ = H

| | Ar | X | Mp (° C.) |
|---|---|---|---|
| Example 74. | phenyl | H₃C-N-CH₂-(pyridin-2-yl) | 1 mol H₂O<br>82<br>White cystals |
| Example 75. | 3-pyridyl | Me₂N | 0.5 mol H₂O<br>82-83<br>Pale-yellow crystals |
| Example 76. | phenyl | Me₂N | 181 (EtOH)<br>White crystals |
| Example 77. | phenyl | H₃C-N-benzyl | 0.25 mol H₂O<br>90-91<br>White crystals |
| Example 78. | 2-chlorophenyl | H₃C-N-benzyl | 157<br>White crystals |

TABLE 7-continued

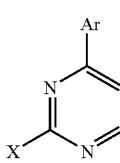

R = Me, Y = Me, Z = OH, W = H, Q = Phenyl,
$R^2$ = H, $R^3$ = H, $R^4$ = H

| | Ar | X | Mp (° C.) |
|---|---|---|---|
| Example 79. | 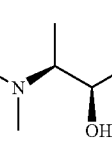 | 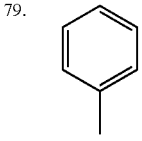 | 0.5 mol $H_2O$<br>84-86<br>White crystals |
| Example 80. | 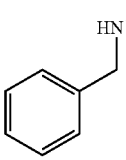 | 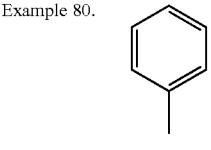 | 1 mol $H_2O$<br>79-81<br>White crystals |
| Example 81. | 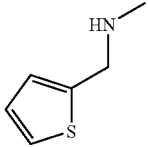 | 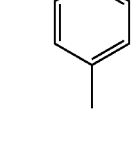 | 0.5 mol $H_2O$<br>86-88<br>White crystals |
| Example 82. | 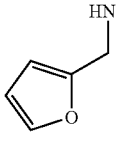 | 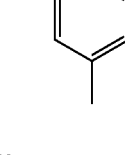 | 0.5 mol $H_2O$<br>81-83<br>White cystals |
| Example 83. | 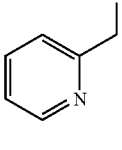 | 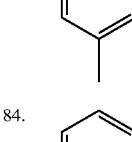 | 0.5 mol $H_2O$<br>98-105<br>White crystals |
| Example 84. | 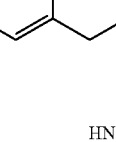 | 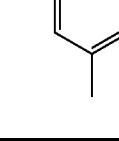 | 0.5 mol $H_2O$<br>79-80<br>Pale-yellow crystals |

Example 85

2-Dimethylamino-4-phenylpyrimidine-5-carboxylic acid (2-hydroxy-2-{3-[(pyridine-2-carbonyl)amino]phenyl}ethyl)methylamide (I)

Ar=Phenyl, X=$Me_2N$, R=Me, Y=H, Z=OH, Z=OH, W=H, $R^3$=2-Pyridyl-CONH, $R^4$=H

Method C (Table 8.)

300 mg PS-TFP resin (0.39 mmol, 1.30 mmol/g) is swelled in N,N-dimethylformamide (3 ml) at room temperature for 5 minutes, then 2-picolinic acid (99 mg, 0.80 mmol), 4-(dimethylamino)pyridine (15 mg, 0.12 mmol) and diisopropyl carbodiimide (125 µl, 0.80 mmol) are added to it. The mixture is stored at room temperature for 20 hours. The resin is filtered off, washed with N,N-dimethylformamide, with tetrahydrofuran and finally with dichloromethane (3×10-10 ml).

The reagent resin is then swelled in 2 ml of N,N-dimethylformamide for 5 minutes under stirring, then 2-dimethylamino-4-phenylpyrimidine-5-carboxylic acid [2-(3-aminophenyl)-2-hydroxyethyl]methylamide (39 mg, 0.10 mmol) is added to it. The mixture is stored at room temperature for 20 hours. The resin is filtered off, washed with N,N-dimethylformamide (2×1 ml). To the resulting solution ethyl acetate (15 ml) is added and the mixture is extracted with 5% citric acid (3×7 ml), then with water (7 ml). The organic phase is dried over sodium sulphate and evaporated. The resulting solid material is digerated with a small amount of water and the resulting white crystalline material is filtered off. 26 mg (52%) of the title compound is obtained, m.p.: 111° C. Purity by HPLC-MS: 97%.

The compounds of Table 8. are prepared according to the process described in Example 85.

TABLE 8

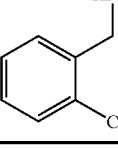

X = $Me_2N$, R = Me, Y = H, Z = OH, W = H,
Q = m-phenylene, $R^2$ = H, $R^3$ = $NHCOR^6$, $R^4$ = H

| | $R^6$ | Mp (° C.) |
|---|---|---|
| Example 85. | 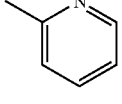 | 111<br>White crystals |
| Example 86. | 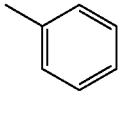 | 1 mol $H_2O$<br>115<br>White crystals |
| Example 87. | 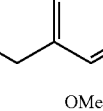 | 1 mol $H_2O$<br>112<br>White crystals |
| Example 88. | 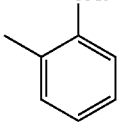 | 112<br>White crystals |
| Example 89. | 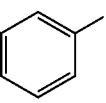 | 104<br>White crystals |

TABLE 8-continued

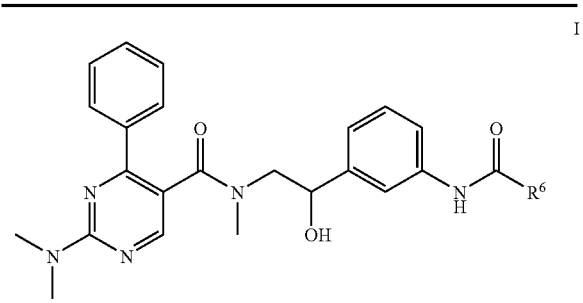

X = Me$_2$N, R = Me, Y = H, Z = OH, W = H,
Q = m-phenylene, R$^2$ = H, R$^3$ = NHCOR$^6$, R$^4$ = H

| | R$^6$ | Mp (° C.) |
|---|---|---|
| Example 90. | 2-thienyl | 115 White crystals |
| Example 91. | 3-thienyl | 126 White crystals |
| Example 92. | 3-furyl | 133 White crystals |
| Example 93. | 3-pyridyl | 135 White crystals |
| Example 94. | 4-pyridyl | 136 White crystals |
| Example 95. | —C(CH$_3$)$_3$ | 0.5 mol H$_2$O 118 White crystals |
| Example 96. | cyclopentyl | 2.5 mol H$_2$O 116-117 White crystals |
| Example 97. | cyclohexyl | 1.5 mol H$_2$O 122-123 White crystals |
| Example 98. | 3,4-dichlorophenyl | 0.5 mol H$_2$O 118 White crystals |
| Example 99. | 3-chlorophenyl | 128 White crystals |
| Example 100. | 2-chlorophenyl | 113 White crystals |

TABLE 8-continued

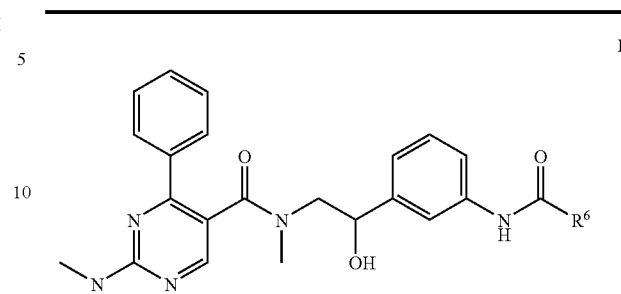

X = Me$_2$N, R = Me, Y = H, Z = OH, W = H,
Q = m-phenylene, R$^2$ = H, R$^3$ = NHCOR$^6$, R$^4$ = H

| | R$^6$ | Mp (° C.) |
|---|---|---|
| Example 101. | 2,5-dichlorophenyl | 120 White crystals |
| Example 102. | 2,4-dichlorophenyl | 122 White crystals |
| Example 103. | 4-methoxyphenyl | 114 White crystals |
| Example 105. | 3,4-dimethoxyphenyl | 130 White crystals |
| Example 104. | 3,5-dimethoxyphenyl | 124 White crystals |
| Example 106. | benzodioxol | 128 White crystals |

Example 107

2-Dimethylamino-4-phenylpyrimidine-5-carboxylic acid {2-[3-(3-tert-butylureido) phenyl]-2-hydroxyethyl}methylamide (I)

Ar=Phenyl, X=Me$_2$N, R=Me, Y=H, Z=OH, W=H, R$^2$=H, R$^3$=t-BuNHCONH, R$^4$=H (Table 9.)

To the solution made of 2-dimethylamino-4-phenylpyrimidine-5-carboxylic acid [2-(3-aminophenyl)-2-hydroxyethyl]methylamide (200 mg, 0.51 mmol) and N,N-dimethylformamide (2 ml), at room temperature tert-butyl isocyanate (60 µl, 0.52 mmol) is added. The reaction mixture is stirred at 60° C. for 20 hours, then ethyl acetate (15 ml) is added and the mixture is extracted with 5% citric acid solution (3×7 ml) and with water (7 ml). The organic phase is dried over sodium sulphate and evaporated. The residue is chromatographed on silicagel using ethyl acetate as eluent. 0.15 g (60%) of the title carbamide is obtained in the form of white crystals; m.p.: 139° C.; purity by HPLC-MS: 99%.

The compounds of Table 9. are prepared according to the process described in Example 107.

TABLE 9

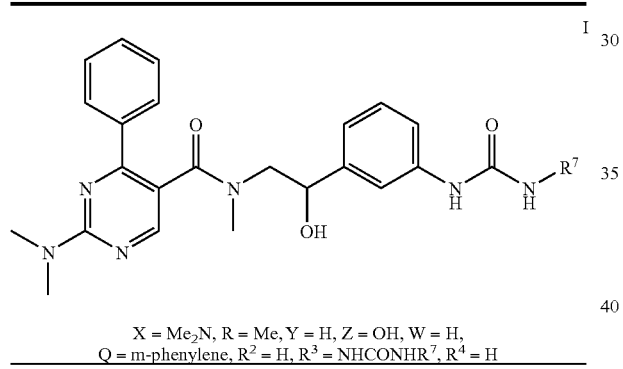

X = Me$_2$N, R = Me, Y = H, Z = OH, W = H,
Q = m-phenylene, R$^2$ = H, R$^3$ = NHCONHR$^7$, R$^4$ = H

| | R$^7$ | Mp (° C.) |
|---|---|---|
| Example 107. | (CH$_3$)$_3$C— | 0.5 mol H$_2$O 139 White crystals |
| Example 108. | phenyl | 0.5 mol H$_2$O 173 White crystals |
| Example 109. | 3-CF$_3$-phenyl | 154 (decomp) White crystals |
| Example 110. | 3,4-diCl-phenyl | 176 White crystals |
| Example 111. | 3-Cl-phenyl | 178 (decomp) White crystals |

TABLE 9-continued

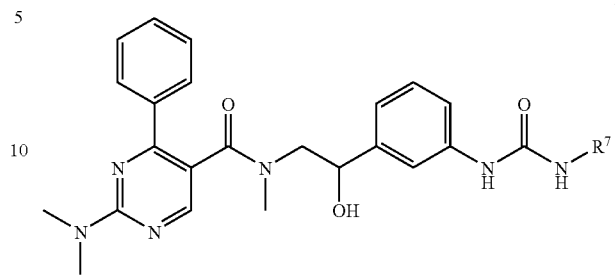

X = Me$_2$N, R = Me, Y = H, Z = OH, W = H,
Q = m-phenylene, R$^2$ = H, R$^3$ = NHCONHR$^7$, R$^4$ = H

| | R$^7$ | Mp (° C.) |
|---|---|---|
| Example 112. | 4-F-phenyl | 125 (decomp) White crystals |
| Example 113. | 4-Cl-phenyl | 175 (decomp) White crystals |
| Example 114. | 4-OMe-phenyl | 128 (decomp) White crystals |
| Example 115. | 4-Me-phenyl | 155 (decomp) White crystals |
| Example 116. | 4-OEt-phenyl | 166 (decomp.) White crystals |
| Example 117. | benzyl | 120 White crystals |

The compounds of Table 10. are prepared according to method B (PyBOP).

TABLE 10

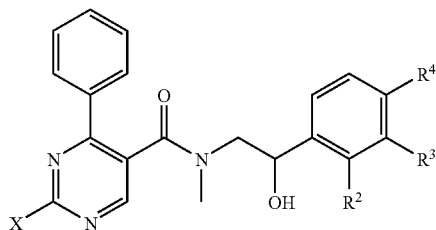

Ar = Phenyl, R = Me, Y = H, Z = OH, W = H, Q = m-phenylene

|  | X | R² | R³ | R⁴ | Mp (° C.) |
|---|---|---|---|---|---|
| Example 118. | H₃C-N(-)-CH₂Ph | H | H | OH | 1 mol H₂O<br>123<br>White crystals |
| Example 119. | H₃C-N(-)-CH₂Ph | OH | H | H | 0.25 mol H₂O<br>91<br>White crystals |
| Example 120. | H₃C-N(-)-CH₂Ph | OCH₃ | H | H | 0.2 mol H₂O<br>87<br>White crystals |
| Example 121. | H₃C-N(-)-CH₂Ph | H | F | H | 65<br>Pale-yellow crystals |
| Example 122. | H₃C-N(-)-CH₂Ph | H | H | F | 1 mol H₂O<br>82-83<br>White crystals |
| Example 123. | H₃C-N(-)-CH₂Ph | H | OCH₃ | H | 1 mol H₂O<br>98<br>Pale-yellow crystals |
| Example 124. | H₃C-N(-)-CH₂Ph | H | H | OCH₃ | 0.25 mol H₂O<br>72<br>White crystals |

TABLE 10-continued

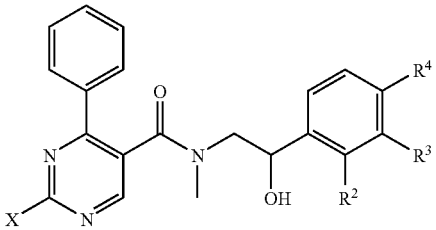

Ar = Phenyl, R = Me, Y = H, Z = OH, W = H, Q = m-phenylene

| | X | R² | R³ | R⁴ | Mp (° C.) |
|---|---|---|---|---|---|
| Example 125. | 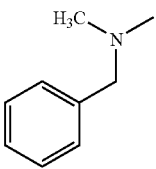 | H | H | H | 1 mol H₂O<br>84<br>White crystals |
| Example 126. | 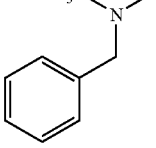 | H | OCH(CH₃)₂ | H | 0.2 mol H₂O<br>60<br>Pale-yellow crystals |
| Example 127. | Me₂N | H | NH₂ | H | 1 mol H₂O<br>69-74<br>White crystals |
| Example 128. | 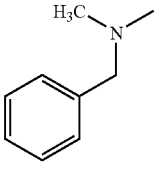 | H | NH₂ | H | 0.5 mol H₂O<br>88<br>White crystals |
| Example 129. | 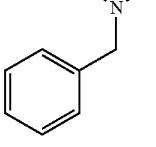 | H | NHCOC(CH₃)₃ | H | 1 mol H₂O<br>92<br>White crystals |
| Example 130. | Me₂N | H | CF₃ | H | 1 mol H₂O<br>HCl-salt<br>69-70<br>Beige-coloured<br>crystals |
| Example 131. | 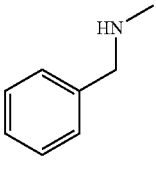 | H | OH | OH | 1 mol H₂O<br>104-106<br>White crystals |
| Example 132. | 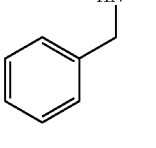 | H | NO₂ | H | 1 mol H₂O<br>76-77<br>White foam |

TABLE 10-continued

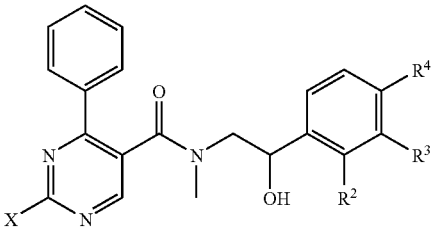

Ar = Phenyl, R = Me, Y = H, Z = OH, W = H, Q = m-phenylene

| | X | R² | R³ | R⁴ | Mp (° C.) |
|---|---|---|---|---|---|
| Example 133. | 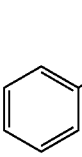 | H | NH₂ | H | 2 HCl-salt<br>2 mol H₂O<br>105-120<br>Pale-yellow crystals |
| Example 134. | Me₂N | H | NO₂ | H | 0.2 mol H₂O<br>89<br>Yellow crystals |
| Example 135. | Me₂N | H | 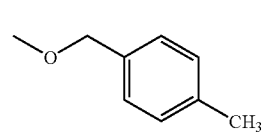 | H | 0.5 mol H₂O<br>57-59<br>White crystals |
| Example 136. | Me₂N | H | 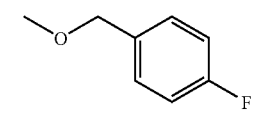 | H | 57-58<br>White crystals |
| Example 137. | Me₂N | H | 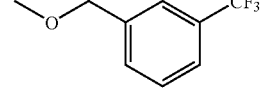 | H | 119-120<br>White crystals |
| Example 138. | Me₂N | H | H | OH | 2 mol H₂O<br>125<br>White crystals |

Example 139

2-Dimethylamino-4-phenylpyrimidine-5-carboxylic acid [2-(3-benzyloxyphenyl)-2-fluoroethyl]methylamide (I)

Ar=Phenyl, X=Me₂N, R=Me, Y=H, Z=F, W=H, R²=H, R=OCH₂C₆H₅, R⁴=H (Table 11.)

To the solution of 2-dimethylamino-4-phenylpyrimidine-5-carboxylic acid [2-(3-benzyloxyphenyl)-2-hydroxyethyl]methylamide (0.30 g, 0.62 mmol) in dichloromethane (2 ml) under nitrogen atmosphere at −78° C. the solution of (diethylamino) sulphur trifluoride (DAST) (132 μl, 1.0 mmol) in dichloromethane (2 ml) is added dropwise, in a period of 2 minutes. The mixture is allowed to warm up to room temperature, stirring is continued for additional 2 hours, then cooled to 0° C. and carefully reacted with a small amount of water, The reaction mixture is extracted with water, then with dichloromethane (20-20 ml), dried over sodium sulphate and evaporated. The residue is chromatographed on silicagel using ethyl acetate as eluent. 0.08 g (27%) of the light drab coloured title compound was obtained, m.p.; 75° C.

Example 140

2-Dimethylamino-4-phenylpyrimidine carboxylic acid [2-(3-hydroxyphenyl)-2-oxoethyl]methylamide Ar=Phenyl, X=Me₂N, R=Me, Y=H, W and Z together C=O, R²=H, R=OH, R⁴=H (Table 11.)

The mixture of 2-dimethylamino-4-phenylpyrimidinecarboxylic acid [2-(3-hydroxyphenyl)-2-hydroxyethyl]methylamide (0.21 g, 0.54 mmol) and pyridinium dichromate (1.0 g, 2.66 mmol) in dichloromethane (5 ml) is stirred at room temperature for 4 hours. To the suspension ether (20 ml) is added, the mixture is filtered through celite, evaporated, chromatographed on silicagel using chloroform, then chloroform: ethyl acetate 4:1, 2:1, 1:1 mixtures as eluents. 0.08 g (38% white crystalline amide was obtained; m.p.: 106° C.

Example 144

(2-Dimethylamino-4-phenylpyrimidin-5-yl)-[2-(3-hydroxyphenyl)morpholin-4-yl]-methanone Ar=Phenyl, X=Me$_2$N, R and Z together CH$_2$CH$_2$O, Y=H, W H, R$^2$=H, R$^3$=OH, R$^4$=H a) 1-(3-Benzyloxyphenyl)-2-(2-hydroxyethylamino) ethanol To the solution of 1-(3-Benzyloxyphenyl)-2-bromomethanone (4.58 g 15 mmol) in methanol (80 ml) under ice-water cooling, sodium borohydride (2.80 g, 74 mmol) is added in small portions in a period of 30 minutes. The mixture is stirred at 0° C. for 30 minutes, then at room temperature for 1 hour. The reaction mixture is evaporated, chloroform (50 ml) is added to it, and washed with 2% hydrochloric acid solution (50 ml) then water (50 ml), dried over sodium sulphate and evaporated to obtain 1-(3-benzyloxyphenyl)-2-bromoethanol (3.43 g) in the form of yellow oil, purity by HPLC-MS: 90%. To the crude product ethanolamine (20 ml) is added and the mixture is stirred at 90° C. for 3 hours. After cooling, ethyl acetate (80 ml) is added to the mixture and washed with water (3×100 ml). From the organic phase the product is extracted with diluted hydrochloric acid. Following alkalinisation with sodium carbonate, the aqueous phase is extracted with dichloromethane. The organic phase is dried over sodium sulphate and evaporated. 1.55 g of 1-(3-benzyloxyphenyl)-2-(2-hydroxyethylamino)ethanol is obtained in the form of yellow-coloured solid, m.p.: 114° C., after recrystallisation from ethyl acetate (15 ml).

b) 2-Dimethylamino-4-phenylpyrimidine-5-carboxylic acid [2-(3-benzyloxyphenyl)-2-hydroxyethyl]-(2-hydroxyethyl)amide To activated 2-dimethylamino-4-phenylpyrimidine-5-carboxylic acid (1.48 g, 1 mmol/g, 1.48 mmol) bound to PS-TFP resin, N,N-dimethylformamide (20 ml), then after 5 minutes of swelling 1-(3-benzyloxyphenyl)-2-(2-hydroxyethylamino)ethanol (0.40 g, 1.39 mmol) is added. The reaction mixture is stirred at room temperature for 18 hours, then filtered and washed consecutively with 50-50 ml of NAN-dimethylformamide, tetrahydrofuran and dichloromethane. After evaporation the resulting oil (0.36 g) is chromatographed on silicagel using chloroform, and chloroform-ethyl acetate 9:1, 4:1 mixtures as eluents. 0.21 g of the title amide is obtained as white solid material, m.p. 89° C.

c) (2-Dimethylamino-4-phenylpyrimidin-5-yl)-[2-(3-hydroxyphenyl)morpholin-4-yl]-methanone To 2-dimethylamino-4-phenylpyrimidin-5-carboxylic acid [2-(3-benzyloxyphenyl)-2-hydroxyethyl]-(2-hydroxyethyl)amide (0.20 g, 0.39 mmol) 48% hydrogen bromide solution (4 ml) is added. The mixture is heated at 100° C. for 1 hour, cooled to room temperature, poured onto water and neutralized (pH 7) with sodium carbonate solution. The precipitate is filtered oft washed with water and dried. The crude product is chromatographed on silicagel using chloroform and chloroform-ethyl acetate 9:1 mixture as eluent. 0.023 g light-yellow title compound is obtained, m.p.: 140° C.

Example 145

2-Dimethylamino-4-phenylpyrimidine-5-carboxylic acid [2-(3-benzyloxyphenyl)-2-chloroethyl]methylamide Ar=Phenyl, X=Me$_2$N, R=Me, Y=H, Z=Cl, W=H, R$^2$=H R$^3$=OCH$_2$C$_6$H$_5$, R$^4$=H (Table 11.)

To the solution of 2-dimethylamino-4-phenylpyrimidine-5-carboxylic acid [2-(3-benzyloxyphenyl)-2-hydroxyethyl]methylamide (1.0 g, 2.07 mmol) in toluene (20 ml), thionyl chloride (1.0 ml) is added. The reaction mixture is stirred at 40° C. for 1 hour and evaporated in vacuum. 1.0 g (96%) pale-yellow crystalline amide is obtained, m.p.: 65° C.

Example 146

2-Dimethylamino-4-phenylpyrimidine-5-carboxylic acid [2-amino-2-(3-benzyloxyphenyl)ethyl]methylamide Ar=Phenyl, X=Me$_2$N, R=Me, Y=H, Z=NH$_2$, W=H, R$^2$=H, R$^3$=OCH$_2$C$_6$H$_5$, R$^4$=H (Table 11.)

To the solution of 2-dimethylamino-4-phenylpyrimidine-5-carboxylic acid [2-(3-benzyloxyphenyl)-2-chloroethyl]methylamide (0.64 g, 1.28 mmol) in N,N-dimethylformamide (13 ml), phthalimide potassium (0.36 g, 1.92 mmol) is added, the reaction mixture is stirred at room temperature for 16 hours, then water (70 ml) is added to it. The precipitated material is filtered off, washed thoroughly with water and dried (0.97 g). To this material ethanol (8 ml) and hydrazine hydrate (121 pd. 2.5 mmol) are added and the mixture is heated at 80° C. for 2 hours. After cooling the resulting white precipitate is filtered off, the filtrate is evaporated; the residue is dissolved in ethyl acetate and washed with water (50 ml). From the organic phase the product is extracted with 5% citric acid solution (3×50 ml) in the form of its salt, the aqueous phase is then alkalinized (pH=9), extracted with dichloromethane, dried over sodium sulphate and evaporated. 0.40 g (65%) of white crystalline material is obtained, m.p.: 147° C.

Example 148

2-Dimethylamino-4-phenylpyrimidine-5-carboxylic acid [2-(3-benzyloxyphenyl)-2-hydroxypropyl]methylamide Ar=Phenyl, X=Me$_2$N, R=Me, Y=H, Z=OH, W=Me, R$^2$=H, R$^3$=OCH$_2$C$_6$H$_5$, R$^4$=H (Table 11.)

To the solution of 2-dimethylamino-4-phenylpyrimidine-5-carboxylic acid [2-(3-benzyloxyphenyl)-2-oxoethyl]methylamide (0.60 g, 1.25 mmol) in tetrahydrofuran (15 ml, under nitrogen atmosphere and ice-water cooling methylmagnesium bromide 3 mol/l solution in diethyl ether (3 ml, 9.0 mmol) is added. The reaction mixture is stirred at 0° C. for 1 hour, then at room temperature for 24 hours. The mixture is poured onto ice, 5% citric acid solution (50 ml) is added to it, the mixture is extracted with ethyl acetate (50 ml), the organic phase is dried over sodium sulphate, evaporated, the residue is chromatographed on silicagel using ethyl acetate as eluent.

0.10 g (16%) white crystalline title compound is obtained, m.p.: 68° C. Purity by HPLC-MS: 99%.

TABLE 11

(I)

| | R | Z | W | R³ | Mp(° C.) |
|---|---|---|---|---|---|
| Example 139. | Me | F | H | OCH₂Ph | 1 mol H₂O 75 White crystals HCl-salt |
| Example 140. | Me | C=O | | OH | 0.5 mol H₂O 106 white crystals |
| Example 141. | Me | C=0 | | OCH₂Ph | 0.2 mol H₂O 162 White crystals |
| Example 142. | Me | MeO | H | OH | 0.2 mol H₂O 180 White crystals |
| Example 143. | Me | MeO | H | OCH₂Ph | 64 Pale-yellow crystals |
| Example 144. | CH₂CH₂O | | H | OH | 140 Pale-yellow crystals |
| Example 145. | Me | Cl | H | OCH₂Ph | 65 Pale-yellow crystals |
| Example 146. | Me | NH₂ | H | OCH₂Ph | 0.2 mol H₂O 147 White crystals |
| Example 147. | Me | NHCOCH₃ | H | OCH₂Ph | 0.5 mol H₂O 103 White crystals |
| Example 148. | Me | OH | Me | OCH₂Ph | 0.2 mol H₂O 68 White crystals |

Ar = Phenyl, X = Me₂N, Y = H, Q = m-phenylene

Example 149

(±) Anti-[2-benzylmethylamino)-4-phenylpyrimidin-5-yl]-[2-(hydroxyphenylmethyl) piperidin-1-yl] methanone (I)

Ar=phenyl, X=Me(C₆H₅CH₂)N, R and Y together —(CH₂)₄—, R²=R³=R⁴=H (Table 12.)

a) Ethyl(2-benzoyl-3-dimethylamino)acrylate (V)

(Herrero, M. T. et al., Tetrahedron 2002, 58(42), 8581-8589

The mixture of ethyl benzoylacetate (25 g, 117 mmol) and N,N-dimethylformamide dimethyl acetal (18.2 ml, 128 mmol) is stirred at 110° C. in microwave reactor (50 W) for 40 minutes. After evaporation in vacuum 29 g (100%) of the title compound is obtained, which is used without further purification.

LC/MS: [MH⁺] 248.3 (C₁₄H₁₇NO₃ 247.292)

b) Ethyl 4-phenyl-2-methoxypyrimidine-5-carboxylate (XI)

Ar phenyl, X=MeO

The mixture of ethyl 2-benzoyl-3-(dimethylamino)acrylate (57.9 g, 234.12 mmol), O-methylisocarbamide sulphate (35 g, 284.68 mol), sodium hydrogencarbonate (23.9 g, 284.68 mmol) and N-methylpyrrolidinone (647 ml) is heated at 80° C. for 12 hours. To the reaction mixture ethyl acetate and water are added, the organic phase is washed with hydrochloric acid solution, dried over sodium sulphate, evaporated in vacuum, chromatographed on silicagel using dichloromethane heptane solvent mixture as eluent. 28 g (46%) of the title compound was obtained.

LC/MS [MH⁺] 259.1 (C₁₄H₁₄N₂O₃ 258.276)

c) Ethyl 2-benzylmethylamino)-4-phenylpyrimidine-5-carboxylate (IX)

Ar=phenyl, X=Me(C₆H₅CH₂)N

The mixture of ethyl-4-phenyl-2-methoxypyrimidine-5-carboxylate (28 g, 108.41 mmol) and benzylmethylamine (70 ml, 542 mmol) is stirred in microwave reactor (200 W) at 170° C. for 40 minutes. To the mixture dichloromethane is added, washed with hydrochloric acid solution, dried over sodium sulphate, evaporated in vacuum, chromatographed on silicagel using dichloromethane-heptane solvent mixture as eluent. 4.74 g (12%) of the title compound is obtained.

¹H-NMR δ: 1.05 (t, 3H), 3.15 (s, 3H), 4.1 (q, 2H), 4.95 (s, 2H), 7.1-7.55 (m, 10H), 8.8 (s, 1H).

d) 2-(Benzylmethylamino)-4-phenylpyrimidine-5-carboxylic acid (II)

Ar=phenyl, X=Me(C₆H₅CH₂)N

The mixture of ethyl 2-(benzylmethylamino)-4-phenylpyrimidine-5-carboxylate (4.74 g, 13.64 mmol), potassium hydroxide (2.7 g, 40.93 mmol), ethanol (90 ml) and water (100 ml) is stirred at 80° C. for 2 hours. The reaction mixture is poured onto 3N hydrochloric acid solution. The precipitated material is filtered off, dried at 40° C. for 12 hours. 4.24 g, (97%) of the title compound is obtained.

¹H-NMR δ: 3.18 (s, 3H), 4.84 (s, 2H), 6.9-7.5 (m, 10H), 8.8 (s, 1H).

e) (±) Anti-tert-butyl-2-(hydroxyphenylmethyl)piperidine-1-carboxylate (XVII)

A=CH₂, B=CH, R⁵=H, n=1, PG=Boc

To the solution of bromobenzene (1.11 ml, 7.03 mmol) in dry tetrahydrofuran (35 ml) at −78° C., under nitrogen atmosphere, the solution of butyl lithium in hexane (2.5 N, 4.22 ml, 10.55 mmol) is added. The solution is stirred at −78° C. for 10 minutes, then tert-butyl-2-formylpiperidine-1-carboxylate (1.5 g, 7.03 mmol) dissolved in tetrahydrofuran (5 ml) is added to it. The reaction mixture is allowed to warm up to room temperature, stirred for 1 hour, poured onto water-ethyl acetate mixture. The aqueous phase is extracted with ethyl acetate (2×50 ml), die organic phase is washed with water, dried over sodium sulphate, evaporated in vacuum and chromatographed on silicagel using ethyl acetate/heptane solvent mixture as eluent. 0.305 g (15%) of the title compound is obtained.

LC/MS [MH³⁰] 292.4 (C₁₇H₂₅NO₃ 291.388)

¹H-NMR δ: 1.15 (s, 9H), 1.3-1.8 (m, 4H), 1.95-2.15 (bd, 1H), 2.15-2.3 (bs, 1H), 2.78 (dt, 1H), 3.75-4 (bd, 1H), 4.15-4.3 (m, 1H), 4.9 (dd, 1H), 7.1-7.35 (m, 5H).

f) (±) Anti-phenylpiperidin-2-ylmethanol (IIIa)

A=$CH_2$, B=CH, $R^5$=H, n=1
(Journal of Organic Chemistry (1990), 55(9), 2578-80).

The mixture of (±) Anti tert-butyl-2-(hydroxyphenylmethyl)piperidin-1-carboxylate (0.485 g, 1.66 mmol) and trifluoroacetic acid (1.92 ml, 24.97 mmol) is stirred at room temperature for 1 hour. Water and 1N aqueous sodium hydroxide solution is added to it and the mixture is extracted twice with dichloromethane. The organic phase is washed with water, dried, evaporated in vacuum. 0.243 g, (76%) of the title compound is obtained.

¹H-NMR δ: 1-1, 8 (m, 6H), 2.4-2.7 (m, 2H), 2.8-3.1 (m, 1H), 4.53 (d, 1H), 7.1-7.4 (m, 5H).

g) (±) Anti-[2-(benzylmethylamino)-4-phenylpyrimidin-5-yl]-[2-(hydroxyphenyl methyl)piperidin-1-yl] methanone (I)

Ar=phenyl, X=Me($C_6H_5CH_2$)N, R and Y together —($CH_2$)$_4$—, $R^2$=$R^3$=$R^4$=H The mixture of 2-(benzylmethylamino)-4-phenylpyrimidine-5-carboxylic acid (0.149 g, 0.47 mmol), (±) anti-phenylpiperidin-2-ylmethanol (0.089 g, 0.47 mmol), 1-ethyl-3-(3'-dimethylaminopropyl)carbodiimide hydrochloride (0.178 g, 0.93 mmol), 1-hydroxybenzotriazole (0.126 g, 0.93 mmol), triethylamine (0.13 ml, 0.93 mmol), acetonitrile (12 ml) and dichloromethane (6 ml) is stirred at room temperature for 12 hours, then poured onto water-ethyl acetate mixture. The organic phase is washed with water, dried over sodium sulphate and evaporated in vacuum. The residue is chromatographed on silicagel using ethyl acetate-heptane solvent mixture as eluent. 0.305 g (15%) of the title amide is obtained.

LC/MS [MH⁺] 493 ($C_{31}H_{32}N_4O_2$ 492.62)

Example 150

Table 12

(±) Anti-[2-(benzylmethylamino)-4-phenylpyrimidin-5-yl]-{2-[hydroxy-(3-methoxyphenyl)methyl]piperidin-1-yl}methanone (I)

Ar=phenyl, X Me($C_6H_5CH_2$)N, R and Y together —($CH_2$)$_4$—, $R^2$=H, $R^3$=OH, $R^4$=H a) (±) Anti-tert-butyl 2-[hydroxy-(3-methoxyphenyl)methyl]piperidin-1-carboxylate (XVII)

A=$CH_2$, B=CH, $R^5$=3-MeO, n=1, PG=Boc

The title compound (0.243 g) was prepared starting from tert-butyl-2-formylpiperidin-1-carboxylate (1.5 g) and 3-methoxybromobenzene (1.34 ml) according to the method described in Example 149e).

LC/MS [MH⁺] 322.4 ($C_1H_{27}NO_4$ 321.414)

¹H-NMR δ: 1.12 (s, 9H), 1.3-1.75 (m, 3H), 1.95-2.15 (bd, 1H), 2.1-2.3 (bs, 1H), 2.78 (dt, 1H), 3.72 (s, 3H), 3.75-4 (bd, 1H), 4.15-4.3 (m, 1H), 4.85 (dd, 1H), 6.7-6.9 (m, 3H), 7.12 (d, 1H).

b) (±) Anti-(3-methoxyphenyl)piperidin-2-ylmethanol (IIIa)

A=$CH_2$, B=CH, $R^5$=3-MeO, n=1
(European Journal of Medicinal Chemistry (1980), 15(2), 111-17. WO 02/34718)

The title compound (0.160 g) was prepared starting from (±) anti-tert-butyl 2-[hydroxy-(3-methoxyphenyl)methyl]piperidine-1-carboxylate (0.243 g) according to the method described in Example 149f).

LC/MS [MH⁺] 222, ($C_{13}H_{19}NO_2$ 221.298)

¹H-NMR δ: 1.1-2.1 (m, 6H), 2.45-2.75 (m, 2H), 2.9-3.1 (m, 1H), 3.74 (s, 3H), 4.48 (d, 1H), 6.7-6.9 (m, 3H), 7.2 (d, 1H).

c) (±) Anti[2-(benzylmethylamino)-4-phenylpyrimidin-5-yl]-{2-[hydroxy-(3-methoxy-phenyl)methyl]piperidin-1-yl}methanone (I)

The title compound (0.170 g) was prepared starting from 2-(benzylmethylamino)-4-phenylpyrimidine-5-carboxylic acid (0.283 g) and (±) Anti-(3-methoxyphenyl)piperidin-2-ylmethanol (0.196 g) according to the method described in Example 149g).

LC/MS [MH⁺] 523; ($C_{32}H_{34}N_4O_3$ 522.646)

Example 151

Table 12

(±) Anti-[2-(benzylmethylamino)-4-phenylpyrimidin-5-yl]-{2-[hydroxy-(3-hydroxyphenyl)methyl]piperidin-1-yl}-methanone (I)

Ar=phenyl, X=Me($C_6H_5CH_2$)N, R and Y together —($CH_2$)$_4$—, $R^2$H, $R^3$=OH, $R^4$=H To the solution of (±) Anti [2-(benzylmethylamino)-4-phenylpyrimidin-5-yl]-{2-[hydroxy-(3-methoxy-phenyl)methyl]piperidin-1-yl}methanone (0.066 g, 0.13 mmol) in dichloromethane (3 ml) is added at −60° C. the dichloromethane solution of boron tribromide (1N, 0.95 ml, 0.95 mmol). The resulting solution is stirred at −15° C. for 2 hours, then poured onto the mixture of water and dichloromethane. The aqueous phase is extracted twice with dichloromethane. The organic phase is washed with water, dried over sodium sulphate and evaporated. The residue is chromatographed on silicagel using ethyl acetate-heptane solvent mixture as eluent. 0.047 g (73%) title compound is obtained.

LC/MS [MH⁺] 509; ($C_{31}H_{32}N_4O_3$ 508.619)

Example 152

Table 12

(±) Anti-[2-(Benzylmethylamino)-4-phenylpyrimidin-5-yl]-{2-[(3-fluorophenyl)-hydroxymethyl]piperidin-1-yl}methanone (I)

Ar=phenyl, X=Me($C_6H_5CH_2$)N, R and Y together —($CH_2$)$_4$—, $R^2$=H, $R^3$=F, $R^4$=H a) (±) Anti-tert-butyl 2-[(3-fluorophenyl)hydroxymethyl]piperidin-1-carboxylate (XVII)

The title compound (0.207 g) was prepared starting from tert-butyl-2-formylpiperidine-1-carboxylate (1.79 g) and 3-fluorobromobenzene (1.41 ml) according to the method described in Example 149e).

LC/MS [MH⁺] 310.1; ($C_{17}H_{24}FNO_3$ 309.379)

¹H-NMR δ: 1-1.25 (s, 9H), 1.3-1.75 (m, 3H), 1.95-2.15 (bd, 1H), 2.2-2.5 (s, 1H), 2.68 (dt, 1H), 3.75-3.95 (bd, 1H), 4-4.2 (m, 1H), 4.75 (dd, 1H), 6.7-7.15 (m, 4H).

b) (±) Anti-(3-fluorophenyl)piperidin-2-ylmethanol (IIIa)

(U.S. Pat. No. 4,260,623)

The title compound (0.122 g) was prepared starting from (±) anti-tert-butyl 2-[(3-fluorophenyl)hydroxymethyl]piperidin-1-carboxylate (0.27 g) according to the method described in Example 149f).

LC/MS [MH$^+$] 210) ($C_{12}H_{16}FNO_2$ 209.262)

c) (±) Anti-[2-Benzylmethylamino)-4-phenylpyrimidin-5-yl]-{2-[(3-fluorophenyl)-hydroxymethyl]piperidin-1-yl}methanone (I)

The title compound (0.053 g) was prepared starting from 2-(benzylmethylamino)-4-phenylpyrimidine-5-carboxylic acid (0.122 g) and (±) anti-(3-fluorophenyl)piperidin-2-ylmethanol (0.186 g) according to the method described in Example 149g).

LC/MS [MH$^+$] 511; ($C_{31}H_{31}FN_4O_2$ 510.61)

Example 153

Table 12

(±) Anti-[2-(Benzylmethylamino)-4-phenylpyrimidin-5-yl]-[2-(hydroxypyridin-3-yl-methyl)piperidin-1-yl]methanone a) (±) Anti-tert-butyl 2-(hydroxypyridin-3-ylmethyl)piperidin-1-carboxylate (XVII)

To the solution of 3-bromopyridine (0.54 ml, 5.58 mmol) in dry tetrahydrofuran (6 ml) is added at room temperature the tetrahydrofuran solution of i-propyl magnesium chloride (2N, 0.54 ml, 5.58 mmol). The reaction mixture is stirred at room temperature for 2 hours, then the solution of tert-butyl 2-formylpiperidine-1-carboxylate (1.19 g, 5.58 mmol) in tetrahydrofuran (6 ml) is added to it and stirring is continued for 12 hours. The reaction mixture is poured onto the mixture of water and dichloromethane. The aqueous phase is extracted twice with dichloromethane (2×50 ml). The organic phase is washed with water, dried over sodium sulphate and evaporated. The residue is chromatographed on silicagel using ethyl acetate-heptane solvent mixture as eluent. 0.478 g (40%) title compound is obtained.

¹H-NMR δ: 1.38 (s, 9H), 1-1.95 (m, 4H), 2.2-2.32 (bd, 1H), 2.94 (dt, 1H), 3.05-3.3 (bs, 1H), 4-4.2 (bd, 1H), 4.4-4.55 (m, 1H), 5.15 (dd, 1H), 7.34-7.48 (m, 1H), 7.9 (d, 1H), 8.6-8.75 (m, 2H).

b) (±) Anti-piperidin-2-yl-pyridin-3-ylmethanol (IIIa)

The title compound (0.17 g) was prepared starting from (±) anti-tert-butyl 2-(hydroxy-pyridin-3-ylmethyl)piperidine-1-carboxylate (0.478 g) according to the method described in Example 149f).

¹H-NMR δ: 1-1.8 (m, 6H), 2.2-2.8 (m, 5H), 3 (d, 1H), 4.6 (d, 1H), 7.1-7.25 (m, 2H), 7.6 (d, 1H) 8.3-0.5 (m, 2H).

c) (±) Anti-[2-(Benzylmethylamino)-4-phenylpyrimidin-5-yl]-[2-(hydroxypyridin-3-yl-methyl)piperidin-1-yl]methanone (I)

The title compound (0.13 g) was prepared starting from 2-(benzylmethylamino)-4-phenylpyrimidine-5-carboxylic acid (0.232 g) and (±) anti-piperidin-2-yl-pyridin-3-ylmethanol (0.139 g) according to the method described in Example 149g)

LC/MS [MH$^+$] 494; ($C_{30}H_{31}N_5O_2$ 493.6)

Example 154

Table 12

(±) Anti-[2-(Benzylmethylamino)-4-(2-chlorophenyl)pyrimidin-5-yl]-[2-(hydroxyphenylmethyl)piperidin-1-yl]methanone (I)

a) Ethyl 2-(2-chlorobenzoyl)-3-(dimethylamino)acrylate (V)

(EP 0 638 557 A1)

The title compound (31 g) was prepared starting from ethyl 2-chlorobenzoylacetate (25 g) according to the method described in Example 149a).

LC/MS [MH$^+$] 282.2 ($C_{14}H_{16}ClNO_3$ 281.737)

b) Ethyl 4-(2-chlorophenyl)-2-methoxypyrimidine-5-carboxylate (XI)

The title compound (12.96 g) was prepared starting from ethyl 2-(2-chlorobenzoyl)-3-(dimethylamino)acrylate (31 g) according to the method described in Example 149b).

LC/MS [MH$^+$] 293.3 ($C_{14}H_{13}ClN_2O_3$ 292.721)
¹H-NMR δ: 1 (t, 3H), 4.05 (s, 3H), 4.1 (q, 2H), 7.2-7.4 (m, 4H), 9.05 (s, 1H).

c) Ethyl 2-(benzylmethylamino)-4-(2-chlorophenyl)pyrimidine-5-carboxylate (IX)

The title compound (2.69 g) was prepared starting from ethyl 4-(2-chlorophenyl)-2-methoxypyrimidine-5-carboxylate (12.96 g) according to the method described in Example. 149c).

¹H-NMR δ: 1.15 (t, 3H), 3.3 (s, 3H), 4.2 (q, 2H), 5.05 (bs, 2H), 7.1-7.6 (m, 9H), 9.08 (s, 1H).

d) 2-(Benzylmethylamino)-4-(2-chlorophenyl)pyrimidine-5-carboxylic acid (II)

The title compound (1.55 g) was prepared starting from ethyl 2-(Benzylmethylamino)-4-(2-chlorophenyl)pyrimidine-5-carboxylate (2.69 g) according to the method described in Example 149d).

¹H-NMR δ: 3.13 (bs, 3H), 4.88 (bs, 2H), 7-7.4 (m, 9H), 8.92 (s, 1H).

e) (±) (Anti-[2-(Benzylmethylamino)-4-(2-chlorophenyl)pyrimidin-5-yl]-[2-(hydroxyphenylmethyl)piperidin-1-yl]methanone (I)

The title compound (0.068 g) was prepared starting from 2-(benzylmethylamino)-4-(2-chlorophenyl)pyrimidine-5-carboxylic acid (0.298 g) and (±) anti-phenyl-piperidin-2-ylmethanol (0.161 g) according to the method described in Example 149e)

LC/MS [MH$^+$] 527 ($C_{31}H_{31}ClN_4O_2$ 526) .

Example 155

Table 12

(±) Anti-[2-(benzylmethylamino)-4-phenylpyrimidin-5-yl]-[2-(hydroxypyridin-2-ylmethyl)piperidin-1-yl]methanone a) (±) Anti-tert-butyl 2-(hydroxypyridin-2-ylmethyl)piperidine-1-carboxylate (XVII)

The title compound (0.11 g) was prepared starting from tert-butyl 2-formylpiperidine-1-carboxylate (1.5 g) and 2-bromopyridine (0.67 ml) according to the method described in Example 153a).
$^1$H-NMR δ: 1.1 (s, 9H), 1-1.9 (m, 4H), 2-2.2 (m, 1H), 3 (t, 1H), 3.9-4.2 (m, 2H), 4.5 (d, 1H), 4.9 (t, 1H), 7-7.25 (m, 2H), 7.55 (t, 1H), 8.5 (d, 1H).
LC/MS [MH$^+$] 293.3; (C$_{16}$H$_{24}$N$_2$O$_3$ 292.3)

b) (±) Anti-piperidin-2-yl-pyridin-2-ylmethanol (IIIa)

The title compound (0.057 g) was prepared starting from (±) anti-tert-butyl 2-(hydroxy-pyridin-2-ylmethyl)piperidine-1-carboxylate (0.11 g) according to the method described in Example 149f).
$^1$H-NMR δ: 1-2 (m, 6H), 2.45-2.75 (m, 1H), 2.8-2.95 (m, 1H), 3-3.2 (m, 1H), 4.63 (d, 1H), 7.1-7.4 (m, 3H), 7.55-7.7 (m, 1H), 8.45-8.55 (m, 1H).

c) (±) Anti-[2-benzylmethylamino)-4-phenylpyrimidin-5-yl]-[2-(hydroxypyridin-2-ylmethyl)piperidin-1-yl]methanone (I)

The title compound (0.03 g) was prepared starting from 2-(benzylmethylamino)-4-phenylpyrimidine-5-carboxylic acid (0.095 g) and (±) anti-piperidin-2-yl-pyridin-2-ylmethanol (0.057 g) according to the method described in Example 149g).
LC/MS [MH$^+$] 494; (C$_{30}$H$_{31}$N$_5$O$_2$ 493)

TABLE 12

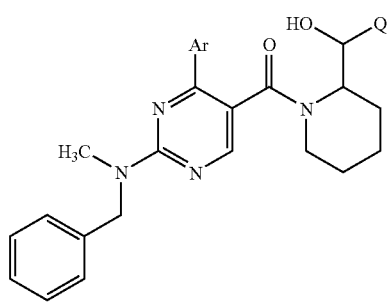

| | Ar | Q | Mp(° C.) |
|---|---|---|---|
| Example 149. | 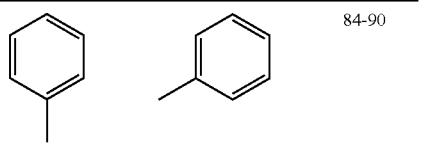 | | 84-90 |
| Example 150. | | | 85-90 |
| Example 151. | | | 105-115 |
| Example 152. | | | 92-105 |
| Example 153. | | | 92-106 |
| Example 154. | | | 85-105 |
| Example 155. | | | 113-130 |

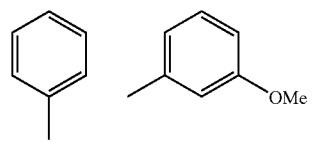
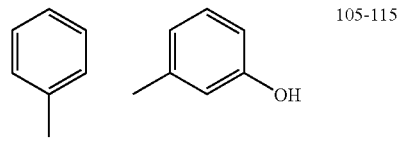
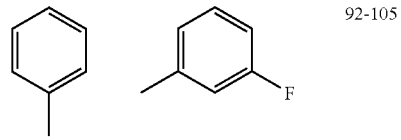
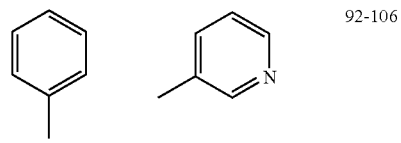
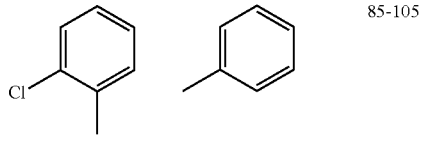
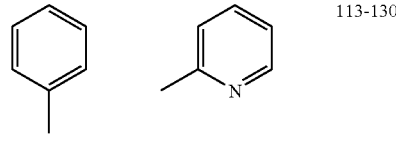

Ar = Phenyl, X = Me(C$_6$H$_5$CH$_2$)N

Compounds of Table 12A were prepared according to method B described in Example 17e)

TABLE 12A
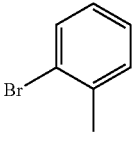
| | Ar | X | R³ | R⁴ | Mp (° C.) |
|---|---|---|---|---|---|
| Example 156. | 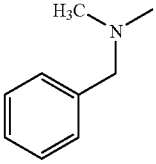 |  | Cl | Cl | 1 mol H₂O 77-79 |
| Example 157. | 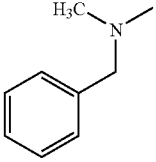 | 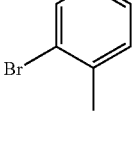 | Cl | Cl | 0.5 mol H₂O 68-72 |
| Example 158. | 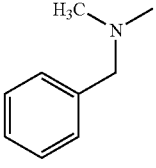 | 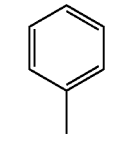 | OH | OH | 1 mol H₂O 99-103 |
| Example 159. | 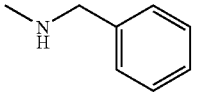 | Me₂N |  | H | 0.5 mol H₂O 60-64 |
| Example 160. | 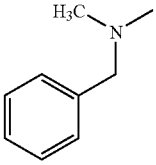 |  | OH | H | 1 mol H₂O 74-78 |
| Example 161. | 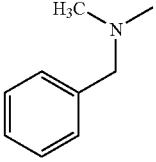 | 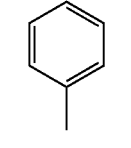 | H | Cl | 68-72 |
| Example 162. | 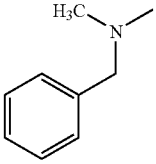 | | Cl | H | 0.5 mol H₂O 74-77 |

TABLE 12A-continued
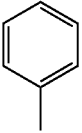
| | Ar | X | R³ | R⁴ | Mp (° C.) |
|---|---|---|---|---|---|
| Example 163. | 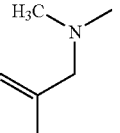 | 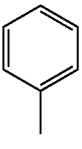 | F | F | 0.5 mol H₂O 64-66 |
| Example 164. | 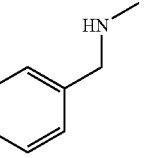 | 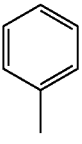 | Cl | H | 1.5 mol H₂O 74-77 |
| Example 165. | 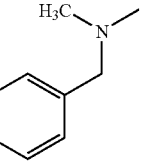 | 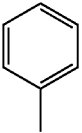 | H | Cl | 77-81 |
| Example 166. | 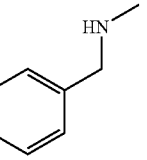 | 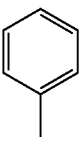 | H | CN | 1 mol H₂O 86-87 |
| Example 167. | 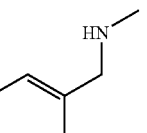 | 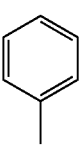 | H | Cl | 1 mol H₂O 75-78 |
| Example 168. | 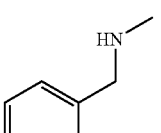 |  | | OCH₂O | 1.5 mol H₂O 85-89 |
| Example 169. | 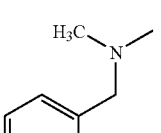 | | | OCH₂O | 1 mol H₂O 73-75 |

TABLE 12A-continued
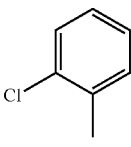
| | Ar | X | R³ | R⁴ | Mp (° C.) |
|---|---|---|---|---|---|
| Example 170. | 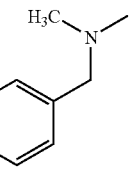 | 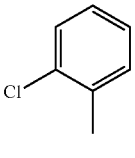 | H | Cl | 1 mol H₂O 72-74 |
| Example 171. | 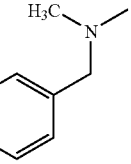 | 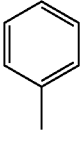 | OH | OH | 1 mol H₂O 95-97 |
| Example 172. | 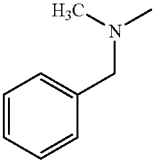 | 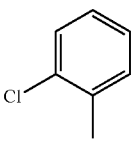 | H | CN | 0.5 mol H₂O 65-67 |
| Example 173. | 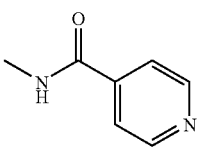 | Me₂N |  | H | 0.5 mol H₂O 135-140 |
| Example 174. | 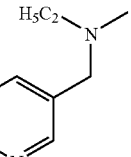 | H₅C₂―N―Me | OH | H | 1 mol H₂O 82-86 |
R = Me, Y = H, Z = OH, W = H TABLE 12B
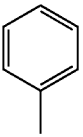
|  | Ar | X | Q | Mp (° C.) |
|---|---|---|---|---|
| Example 175. | 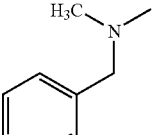 | 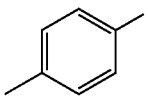 | 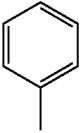 | 85-90 |
| Example 176. | 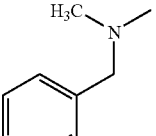 | 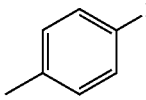 | 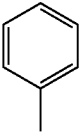 | 80-85 |
| Example 177. | 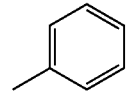 | MeS | 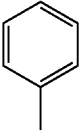 | M + H+ = 420 |
| Example 178. | 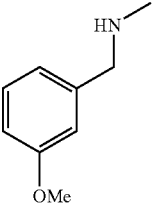 | 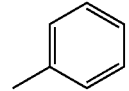 | 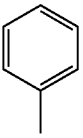 | 85-95 |
| Example 179. | 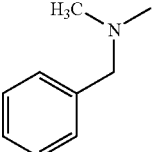 | 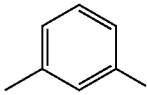 | 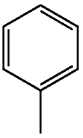 | 85-115 |
| Example 180. | 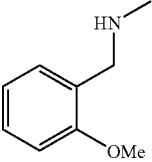 | 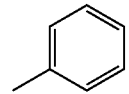 | 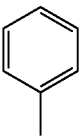 | 208 |
| Example 181. | 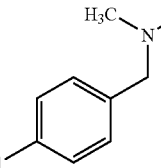 | 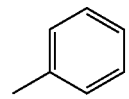 |  | 180-184 |

TABLE 12B-continued
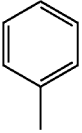
I
| | Ar | X | Q | Mp (° C.) |
|---|---|---|---|---|
| Example 182. | 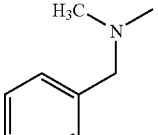 | 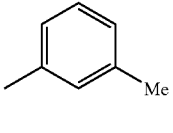 | 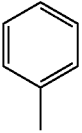 | 95-100 |
| Example 183. | 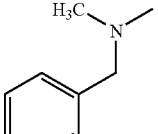 | 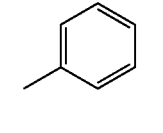 | 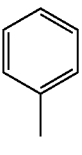 | >200 |
| Example 184. | 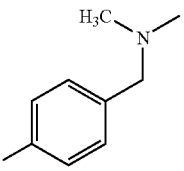 | 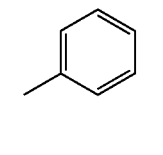 | 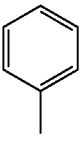 | 172 |
| Example 185. | 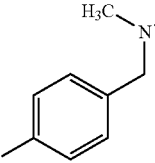 | 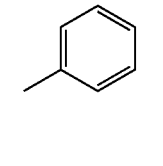 | 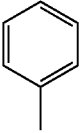 | 180 |
| Example 186. | 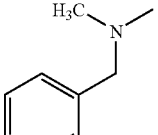 | 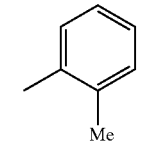 | 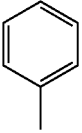 | 95-100 |
| Example 187. | 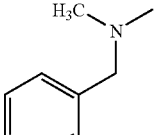 | 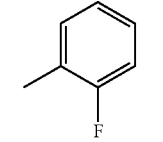 | 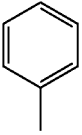 | 100-105 |
| Example 188. | 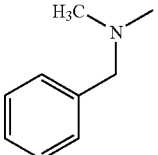 | 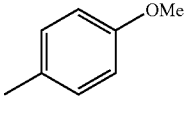 | | 86-98 |

TABLE 12B-continued
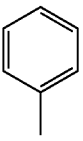
I
| | Ar | X | Q | Mp (° C.) |
|---|---|---|---|---|
| Example 189. | 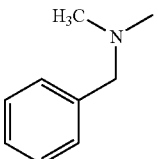 | 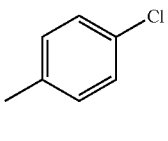 | 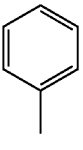 | 85-90 |
| Example 190. | 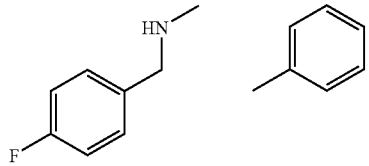 | 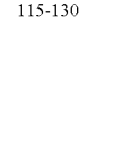 | 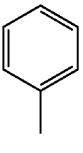 | 115-130 |
| Example 191. | 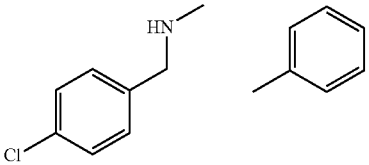 | 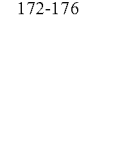 |  | 172-176 |
| Example 192. | 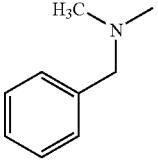 | 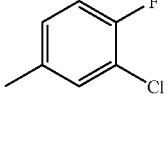 |  | 90-100 |
| Example 193. | 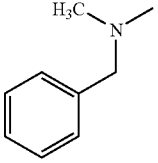 | 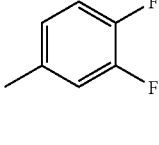 |  | 79-83 |
| Example 194. | 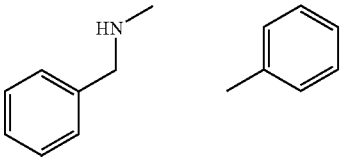 |  | 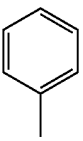 | 155-162 |
| Example 195. | 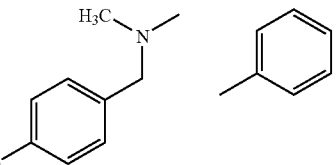 |  | | 208-212 |

TABLE 12B-continued
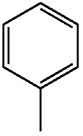
| | Ar | X | Q | Mp (° C.) |
|---|---|---|---|---|
| Example 196. | 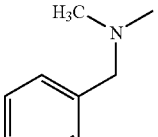 | 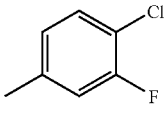 | 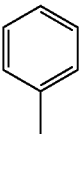 | 85-95 |
| Example 197. | 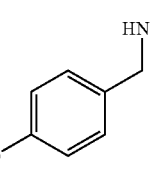 | 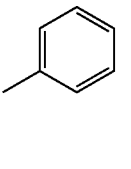 | 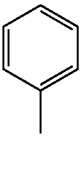 | 105-115 |
| Example 198. | 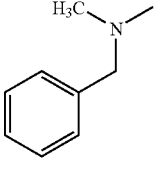 | 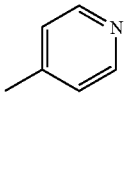 |  | 95-108 |
| Example 199. | 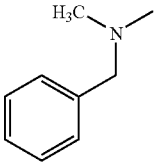 | 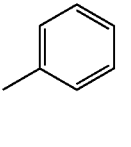 | 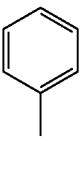 | 107-110 |
| Example 200. | 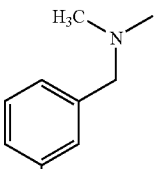 | 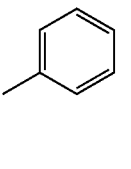 | 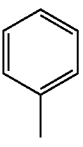 | 125-130 |
| Example 201. | 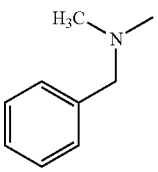 | 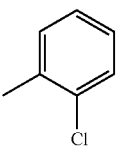 | 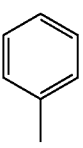 | 95-100 |
| Example 202. | 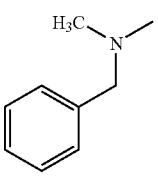 | 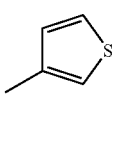 | | 90-100 |

TABLE 12B-continued
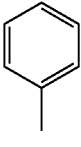
I
| | Ar | X | Q | Mp (° C.) |
|---|---|---|---|---|
| Example 203. | 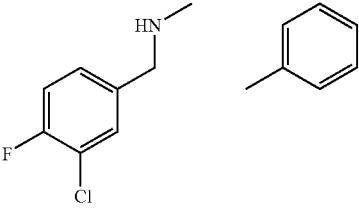 |  | 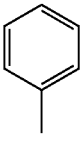 | 88-92 |
| Example 204. | 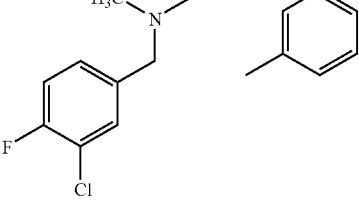 |  | 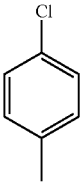 | 194-196 |
| Example 205. | 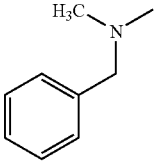 | 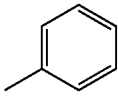 | 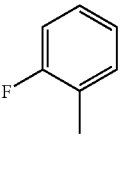 | 187-195 |
| Example 206. | 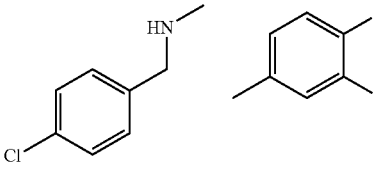 |  | 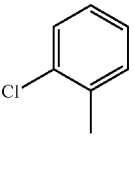 | 168-170 |
| Example 207. | 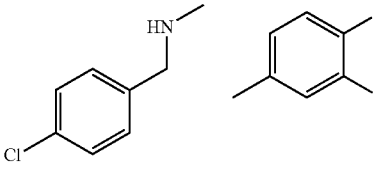 |  | 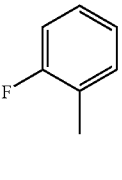 | 151-154 |
| Example 208. | 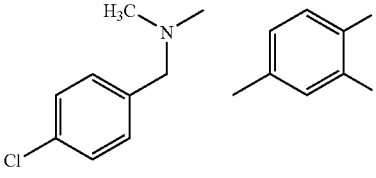 |  | | 171-174 |

TABLE 12B-continued
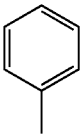
| | Ar | X | Q | Mp (° C.) |
|---|---|---|---|---|
| Example 209. | 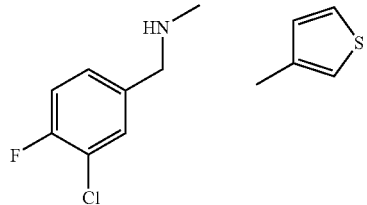 | 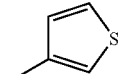 | 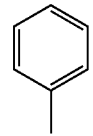 | 83-95 |
TABLE 13
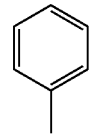
| | Ar | X | Mp ° C. or ¹H-NMR or HPLC |
|---|---|---|---|
| IX-1 | 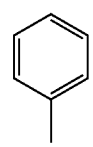 | (CH₃)₂N | J. Heterocyclic Chem. 18, 183, (1981) 35-36° C. White crystals |
| IX-2 | 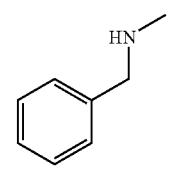 | NH₂ | J. Heterocyclic Chem. 18, 183, (1981) 156° C. White crystals |
| IX-3 | 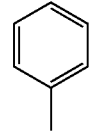 | 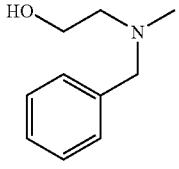 | 91-92° C. Pale-yellow crystals |
| IX-4 | 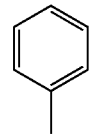 | 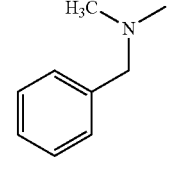 | [M + H]⁺ 378 Pale-yellow oil |
| IX-5 | | | 1.05 (t, 3H), 3.15 (s, 3H), 4.1 (q, 2H), 4.95 (s, 2H), 7.1-7.55 (m, 10H), 8.8 (s, 1H). |

TABLE 13-continued
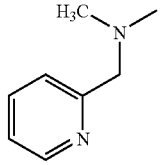
| | Ar | X | Mp ° C. or ¹H-NMR or HPLC |
|---|---|---|---|
| IX-6 | 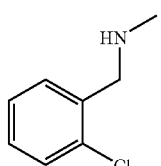 | 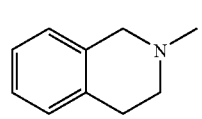 | [M + H]⁺ 349<br>Pale-yellow oil |
| IX-7 | | 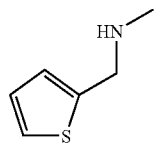 | 101-102<br>White crystals |
| IX-8 | | 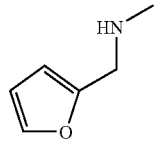 | [M + H]⁺ 360<br>Pale-yellow oil |
| IX-9 | | 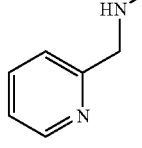 | 123-124 (EtOH)<br>White crystals |
| IX-10 | | 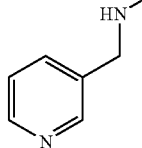 | 99-100 (EtOH)<br>White crystals |
| IX-11 | | 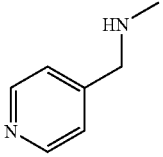 | [M + H]⁺ 335<br>Colourless oil |
| IX-12 | | | [M + H]⁺ 335<br>Pale-yellow oil |
| IX-13 | | | [M + H]⁺ 335<br>Yellow oil |

TABLE 13-continued
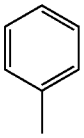
IX
| | Ar | X | Mp °C. or ¹H-NMR or HPLC |
|---|---|---|---|
| IX-14 |  | (CH₃)₃CNH | 1.1 (t, 3H), 1.5 (s, 9H), 4.14 (q, 2H), 4.97 (s, 1H), 7.3-7.55 (m, 5H), 8.81 (broad s, 1H). |
| IX-15 |  | (CH₃)₂CHNH | [M + H]⁺ 286 |
| IX-16 | 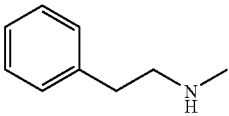 | 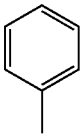 | [M + H]⁺ 348 |
| IX-17 | 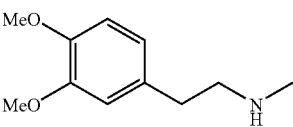 | 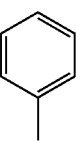 | 100-101<br>White crystals |
| IX-18 | 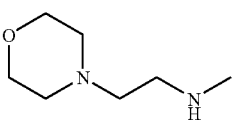 | 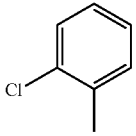 | [M + H]⁺ 357<br>Pale-yellow oil |
| IX-19 | 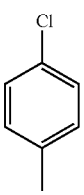 | (CH₃)₂N | Yellow crystals |
| IX-20 | 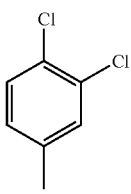 | (CH₃)₂N | 69° C.<br>White crystals |
| IX-21 |  | (CH₃)₂N | 143-144 (EtOH)<br>Pale-yellow crystals |

TABLE 13-continued $$\text{structure IX: 2-X, 4-Ar, 5-COOEt pyrimidine}$$

| | Ar | X | Mp ° C. or ¹H-NMR or HPLC |
|---|---|---|---|
| IX-22 Methyl ester | 2,5-dichloro-4-fluorophenyl | (CH₃)₂N | 163-164° C. White crystals |
| IX-23 | 4-fluorophenyl | (CH₃)₂N | 94-95° C. J. Heterocyclic Chem. 18, 183, (1981) |
| IX-24 | 2-iodophenyl | (CH₃)₂N | Yellow crystals |
| IX-25 | 2-iodophenyl | N-methyl-N-benzyl-N-methylamino (H₃C-N(CH₃)-CH₂-C₆H₅) | [M + H]⁺ 474 |
| IX-26 | 2-iodophenyl | CH₃S | [M + H]⁺ 401 Oil |
| IX-27 | 2-iodophenyl | CH₃SO₂ | [M + H]⁺ 433 |
| IX-28 | 4-pyridyl | (CH₃)₂N | 103-104° C. |
| IX-29 | 4-pyridyl | NH₂ | 245-246° C. |

TABLE 13-continued
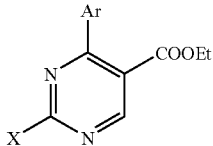
| | Ar | X | Mp ° C. or $^1$H-NMR or HPLC |
|---|---|---|---|
| IX-30 | 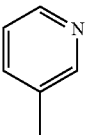 | (CH$_3$)$_2$N | 90-91° C.<br>Pale-yellow crystals |
| IX-31 | 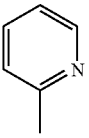 | NH$_2$ | 150-151° C. |
| IX-32 | 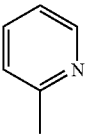 | (CH$_3$)$_2$N | 80-81° C.<br>White crystals |
TABLE 14
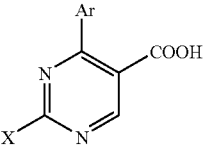
| | Ar | X | Mp ° C. or $^1$H-NMR |
|---|---|---|---|
| II-1 | 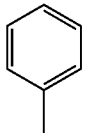 | (CH$_3$)$_2$N | J. Med. Chem. 1996, 39(19), 3671<br>224-225° C.<br>White crystals |
| II-2 | 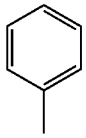 | NH$_2$ | J. Heterocyclic Chem. 1990, 27, 295<br>268-270° C.<br>White crystals |
| II-3 | 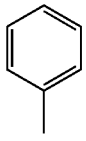 | 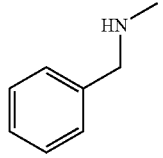 | 231-232<br>(EtOH)<br>White crystals |

TABLE 14-continued
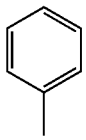
| | Ar | X | Mp ° C. or ¹H-NMR |
|---|---|---|---|
| II-4 | 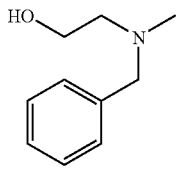 | 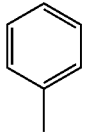 | 184-185<br>White crystals |
| II-5 | 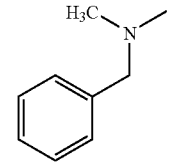 | 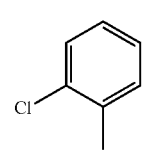 | 3.18 (s, 3H), 4.84 (s, 2H), 6.9-7.5 (m, 10H), 8.8 (s, 1H). |
| II-6 | 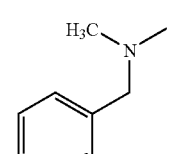 | 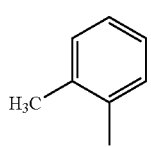 | 92° C. |
| II-7 | 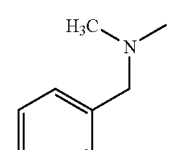 | 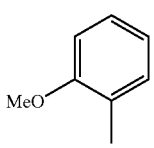 | 142° C. |
| II-8 | 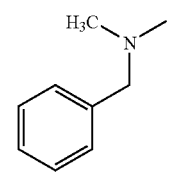 | 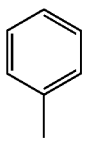 | 71-72° C.<br>Pale-yellow crystals |
| II-9 | 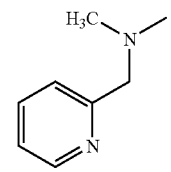 | 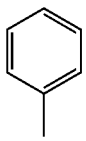 | 225-227<br>White crystals |
| II-10 | 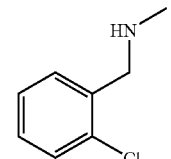 | 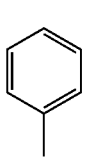 | 196<br>(EtOH)<br>White crystals |
| II-11 | | 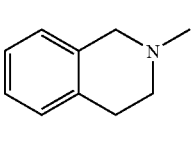 | 159-160<br>White crystals |

TABLE 14-continued

|  | | | II |

Structure: Pyrimidine with Ar at 4-position, COOH at 5-position, X at 2-position.

| | Ar | X | Mp °C. or ¹H-NMR |
|---|---|---|---|
| II-12 | phenyl (4-methyl) | HN-CH₂-(2-thienyl), N-methyl | 212-213<br>White crystals |
| II-13 | phenyl (4-methyl) | HN-CH₂-(2-furyl), N-methyl | 190-194<br>White crystals |
| II-14 | phenyl (4-methyl) | HN-CH₂-(2-pyridyl), N-methyl | 176<br>(CH₂Cl₂)<br>White crystals |
| II-15 | phenyl (4-methyl) | HN-CH₂-(3-pyridyl), N-methyl | 99-101<br>Pale-yellow crystals |
| II-16 | phenyl (4-methyl) | HN-CH₂-(4-pyridyl), N-methyl | [M + H]⁺ 307 |
| II-17 | phenyl (4-methyl) | (CH₃)₃CNH | 228-230<br>Pale-yellow crystals |
| II-18 | phenyl (4-methyl) | N-methylpyrrolidinyl | 250° C.<br>White crystals |
| II-19 | phenyl (4-methyl) | (CH₃)₂CHNH | 198-200<br>(EtOH)<br>White crystals |

TABLE 14-continued
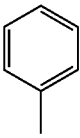
| | Ar | X | Mp °C. or $^1$H-NMR |
|---|---|---|---|
| II-20 | 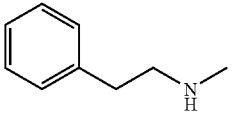 | 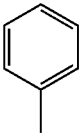 | 198-199° C.<br>(EtOH)<br>White crystals |
| II-21 | 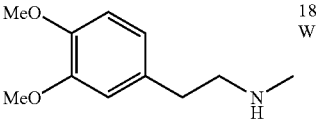 | 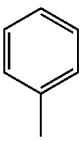 | 182-183<br>White crystals |
| II-22 | 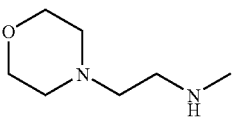 | 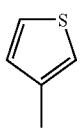 | 242-243° C.<br>Pale-yellow crystals |
| II-23 | 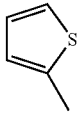 | $(CH_3)_2N$ | 228° C. |
| II-24 |  | $(CH_3)_2N$ | |
| II-25 | 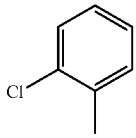 | $(CH_3)_2N$ | 273° C.<br>Pale-yellow crystals |
| II-26 | 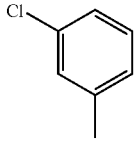 | $(CH_3)_2N$ | 205-207° C.<br>White crystals |
| II-27 |  | $(CH_3)_2N$ | 213° C. |

TABLE 14-continued
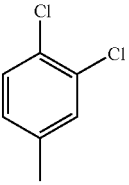
| | Ar | X | Mp ° C. or ¹H-NMR |
|---|---|---|---|
| II-28 | 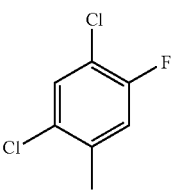 | (CH₃)₂N | 255-256° C.<br>White crystals |
| II-29 | 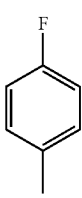 | (CH₃)₂N | 224-225° C.<br>White crystals |
| II-30 | 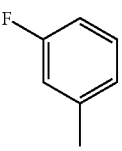 | (CH₃)₂N | 259° C. |
| II-31 |  | (CH₃)₂N | 250° C. |
| II-32 | 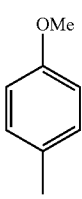 | (CH₃)₂N | 252° C.<br>White crystals |
| II-33 | 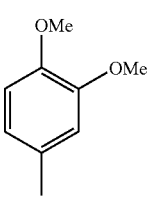 | (CH₃)₂N | 249-250° C. |
| II-34 | OMe / OMe phenyl | (CH₃)₂N | 195-197° C.<br>White crystals |

TABLE 14-continued $$\text{structure: pyrimidine with Ar at 4-position, COOH at 5-position, X at 2-position}$$

II

| | Ar | X | Mp ° C. or ¹H-NMR |
|---|---|---|---|
| II-35 | 5-methyl-benzo[1,3]dioxole | (CH₃)₂N | 214° C. |
| II-36 | 2-(trifluoromethyl)-methylphenyl | (CH₃)₂N | 201° C.<br>White crystals |
| II-37 | 2-iodo-methylphenyl | (CH₃)₂N | 208-209° C.<br>Pale-yellow crystals |
| II-38 | 2-iodo-methylphenyl | N-methyl-N-benzyl (H₃C-N-CH₂Ph) | [M + H]⁺ 446 |
| II-39 | 4-(NHCOCH₃)-methylphenyl | (CH₃)₂N | 270° C.<br>Pale-yellow crystals |
| II-40 | 4-(NMe₂)-methylphenyl | (CH₃)₂N | 227° C.<br>Yellow crystals |
| II-41 | 4-methylpyridine | (CH₃)₂N | 261-262° C.<br>Pale-yellow crystals |
| II-42 | 3-methylpyridine | (CH₃)₂N | >270° C.<br>White crystals |

TABLE 14-continued

Structure II: pyrimidine with Ar at 4-position, X at 2-position, COOH at 5-position

| | Ar | X | Mp ° C. or $^1$H-NMR |
|---|---|---|---|
| II-43 | 2-pyridyl | NH$_2$ | 218-220° C. |
| II-44 | 2-pyridyl | (CH$_3$)$_2$N | 193-195° C. Yellow crystals |

Biological Screening Method

In vitro radioligand binding assays were used for determination of the affinities of the compounds for both the orexin-1 and orexin-2 receptors.

In the frame of hr-$^{125}$I-orexin-A radioligand competition (displacement) experiments a fixed concentration of hr-$^{125}$I-orexin-A is incubated with increasing concentrations of unlabeled test compound in the presence of highly purified plasmamembranes bearing either the human recombinant orexin-1 (hr-OX-1) or the human recombinant orexin-2 (hr-OX-2) receptors. Specific binding of hr-$^{125}$I-orexin-A to plasmamembranes is measured at each concentrations of the unlabeled compound and thus a competition curve is generated. The concentration of unlabeled compound displacing 50% of specific binding (IC$_{50}$) is calculated. In case of competitive interaction the binding affinity constant of the unlabeled compound (K$_1$) is calculated according to the Cheng-Prusoff equation (K$_1$=IC$_{50}$/(1+L*/K$_D$). Affinity of unlabeled compound for the receptor is equal to 1/K$_1$.

In Vitro Cell Culturing and Preparation of Highly Purified Plasmamembrane Fractions Containing Orexin Receptors Culturing the Chinese hamster ovarian cells expressing human recombinant orexin-1 or orexin-2 receptor proteins (CHO-hr-OX-1 or CHO-hr-OX-2 cells) was carried out in cell culture medium (MEM medium, supplemented with 40 mg/l prolin, 20 mg/l gentamycin, 300 mg/l geneticin, 10% dialysed fetal calf serum).

We have worked out a new method for the separation of plasmamembrane fractions enriched in orexin-1 or orexin-2 receptor proteins.

Adherent cells were plated into Greiner flasks (175 cm$^2$). 4-6 days later culture medium was removed and cells were scarped in calcium- and magnesium-free phosphate buffered saline (PBS, 20 ml/flask). The cell suspension was centrifuged at 1,000 g for 5 minutes (4° C.). The resulting pellet was resuspended and homogenized with a teflon pestle (4° C.), then layered onto a discontinuous sucrose gradient and centrifuged at 105,000 g. Plasmamembrane fraction accumulated in the interface between 14 and 34% sucrose layers was separated and pelleted by a further centrifugation step at 105,000 g for 60 min (4° C.). The final pellet was resuspended in binding assay buffer and stored at −80° C. up to the day of radioligand binding experiment.

In Vitro $^{125}$I-Orexin-A Binding

For $^{125}$I-orexin-A competition binding studies, aliquots of cell membrane fractions containing either hr-orexin-1 or hr-orexin-2 receptors were incubated with $^{125}$I-orexin-A in binding assay buffer at 25° C. for 60 minutes. Nonspecific binding was defined by 1 µM hr-orexin-A in both cases.

Test compounds were dissolved at a concentration of 1 mM in dimethylsulfoxide (DMSO). Serial dilution series were prepared from stock solutions (100% DMSO) with binding assay buffer in such a way that each samples contained a final concentration of 1% of DMSO in the receptor binding reaction mixture. After the incubation, samples were filtered through Whatman GF/C glass fibre filters using a SKATRON cell harvester, and the filters were washed with 5 ml of ice-cold buffer The radioactivity remained on the filter was counted in a gamma counter (Wallac Automatic Gamma Counter 1470 Wizard).

Abbreviations:

EGTA ethylene glycol-bis(β-aminoethyl ether)-N,N,N', N'-tetraacetic acid

Tris tris-(hydroxymethyl)aminomethane

HEPES N-2-hydroxyethylpiperazine-N'-2-ethanesulphonic acid

The invention claimed is:

1. A compound of formula (I)

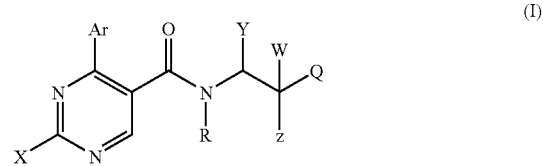

wherein
X is
C$_{1-4}$-alkyl, amino
wherein said amino is optionally substituted with one or two C$_{1-4}$ alkyl groups,
C$_{1-4}$-alkyl-S—, a saturated or partially saturated mono- or bicyclic moiety containing 1 or 2 or 3 heteroatoms independently selected from N, O or S and, when said saturated or partially saturated mono- or bicyclic moiety contains 1 or 2 or 3 nitrogen atoms, said saturated or partially saturated mono- or bicyclic moiety connects to the pyrimidine ring through one of said nitrogen atoms and said mono- or bicyclic moiety cannot be morpholino, benzylamino-, phenylethylamino-, N—C$_{1-4}$ alkylbenzylamino-, N—C$_{1-4}$ alkylphenylethylamino-, N—C$_{1-4}$-hydroxyalkylbenzylamino-, N—C$_{1-4}$-hydroxyalkylphenylethylamino-, cyclohexylmethylamino-, N—(C$_{1-4}$-cyclohexyl-methyl)amino-
wherein the aromatic ring of said mono- or bicyclic moiety, benzylamino-, phenylethylamino-, N—C$_{1-4}$ alkylbenzylamino-, N—C$_{1-4}$ alkylphenylethylamino-, N—C$_{1-4}$-hydroxyalkylbenzylamino- and N—C$_{1-4}$-hydroxyalkylphenylethylamino- is optionally substituted with one or two groups independently selected from C$_{1-4}$ alkyl, C$_{1-4}$ alkoxy, hydroxyl or halogen;
a Het-C$_{1-4}$ alkyl-N(R$^1$)-group
wherein Het is a saturated or unsaturated heterocyclic ring containing one or two heteroatoms independently selected from N, O or S, and wherein said heterocyclic ring is optionally substituted with one or more groups independently selected from C$_{1-4}$ alkyl, C$_{1-4}$ alkoxy or halogen, and
R$^1$ is C$_{1-4}$ alkyl or C$_{1-4}$-hydroxyalkyl;
Ar is phenyl, a 5- or 6-membered heterocyclic ring containing 1, 2 or 3 heteroatoms independently selected from N, O or S, or a methylenedioxyphenyl group
wherein said phenyl, 5- or 6-membered heterocyclic ring or methylenedioxyphenyl group is optionally substituted with one or more groups independently selected from C$_{1-4}$ alkyl, halogen, hydroxyl, C$_{1-4}$ alkoxy, trihalogenomethyl, —NHC$_{1-4}$ alkyl, —N(C$_{1-4}$ alkyl)$_2$ or —NHC(=O)—C$_{1-4}$ alkyl;
R is hydrogen or C$_{1-4}$-alkyl;
Y is hydrogen or C$_{1-4}$-alkyl;
W is hydrogen or C$_{1-4}$-alkyl;
Z is hydroxyl, halogen, C$_{1-4}$-alkoxy, amino, C$_{1-4}$-alkyl-amino- or —NHCOC$_{1-4}$-alkyl;
or R and Y taken together with the nitrogen and carbon atoms to which they are attached form the following group

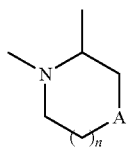

wherein
A is CH$_2$, O, NH, or NC$_{1-4}$-alkyl; and
n is 0, 1, 2;
or R and Z taken together form —(CH$_2$)$_m$-G-, wherein m is 1, 2 or 3, and G is O, CH$_2$, NH or NC$_{1-4}$-alkyl;
or Z and W taken together form an oxo group;
Q is a 5- or 6-membered heterocyclic ring containing 1, 2 or 3 heteroatoms independently selected from N, O or S,
wherein said 5- or 6-membered heterocyclic ring is optionally substituted with one or more groups independently selected from C$_{1-4}$-alkyl, C$_{1-4}$-alkoxy, hydroxyl, or halogen;
or Q is the following group

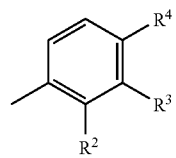

wherein
R$^2$ is hydrogen, halogen, hydroxyl, cyano, C$_{1-4}$-alkoxy or C$_{1-4}$-alkyl;
R$^3$ is hydrogen, halogen, hydroxyl, trihalogenomethyl, amino, cyano, C$_{1-4}$-alkylamino-, di(C$_{1-4}$)alkylamino-, benzylamino-, benzyl-(C$_{1-4}$)alkylamino-, nitro, benzyl, phenylethyl, C$_{1-4}$-alkyl,
—OR$^5$,
wherein R$^5$ is C$_{1-4}$-alkyl or benzyl and wherein said C$_{1-4}$-alkyl and benzyl are optionally substituted with one or more groups independently selected from halogen or trihalogenomethyl group,
—NH—C(=O)—R$^6$,
wherein R$^6$ is phenyl, 4-7-membered cycloalkyl, methylenedioxyphenyl, C$_{1-4}$ alkyl, benzyl, or a heterocyclic ring containing 1 or 2 or 3 heteroatoms independently selected from N, O or S, and wherein said phenyl, 4-7-membered cycloalkyl, methylenedioxyphenyl, C$_{1-4}$ alkyl, benzyl, and heterocyclic ring is optionally substituted with halogen, C$_{1-4}$-alkyl or C$_{1-4}$-alkoxy,
—NH—C(=O)—NH—R$^7$
wherein R$^7$ is C$_{1-4}$-alkyl, benzyl, or phenyl, and wherein said C$_{1-4}$-alkyl, benzyl, and phenyl are optionally mono- or polysubstituted with groups independently selected from halogen, C$_{1-4}$-alkoxy, C$_{1-4}$-alkyl or trihalogenomethyl,
R$^4$ is hydrogen, halogen, hydroxyl, cyano, C$_{1-4}$ alkoxy or C$_{1-4}$ alkyl; or
R$^3$ and R$^4$ taken together form —O—CH2-O—;
with the proviso that, if
Q is a 5- or 6-membered heterocyclic ring containing 1, 2 or 3 heteroatoms as hereinbefore defined and said heterocyclic ring is optionally substituted with one or more groups independently selected from C$_{1-4}$ alkyl, C$_{1-4}$ alkoxy, hydroxyl or halogen, and
W is hydrogen, and
Z is hydroxyl, and
R and Y together with the nitrogen and carbon atoms to which they are attached form the following group

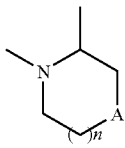

wherein
n is 1 and A is NH—, NC$_{1-4}$-alkyl or —CH$_2$—, and
Ar is as defined above,
then X cannot be C$_{1-4}$ alkyl or amino optionally substituted with one or two C$_{1-4}$ alkyl groups,
and pharmaceutically acceptable salts thereof.

2. The compound of claim 1 wherein
R$^2$ is hydrogen, halogen, hydroxyl, C$_{1-4}$-alkoxy or C$_{1-4}$-alkyl;
R$^3$ is hydrogen, halogen, hydroxyl, trihalogenomethyl, amino, C$_{1-4}$-alkylamino-, di(C$_{1-4}$)alkylamino-, benzylamino-, benzyl-(C$_{1-4}$)alkylamino-, nitro, benzyl, phenylethyl, C$_{1-4}$-alkyl,
—OR$^5$,
wherein R$^5$ is C$_{1-4}$-alkyl or benzyl and wherein said C$_{1-4}$-alkyl and benzyl are optionally substituted with one or more groups independently selected from halogen or trihalogenomethyl group,
—NH—C(=O)—R$^6$,
wherein R$^6$ is phenyl, 4-7-membered cycloalkyl, methylenedioxyphenyl, C$_{1-4}$ alkyl, benzyl, or a heterocyclic ring containing 1 or 2 or 3 heteroatoms independently selected from N, O, or S, and wherein said phenyl, 4-7-membered cycloalkyl, methylenedioxyphenyl, C$_{1-4}$ alkyl, benzyl, and heterocyclic ring is optionally substituted with halogen, C$_{1-4}$-alkyl or C$_{1-4}$-alkoxy,
—NH—C(=O)—NH—R$^7$
wherein R$^7$ is C$_{1-4}$-alkyl, benzyl, or phenyl, and wherein said C$_{1-4}$-alkyl, benzyl, and phenyl are optionally mono- or polysubstituted by groups independently selected from halogen, C$_{1-4}$-alkoxy, C$_{1-4}$-alkyl or trihalogenomethyl, and
R$^4$ is hydrogen, halogen, hydroxyl, C$_{1-4}$ alkoxy or C$_{1-4}$ alkyl.

3. The compound of claim 2 wherein
W is hydrogen or C$_{1-4}$-alkyl;
Z is hydroxyl, halogen, C$_{1-4}$-alkoxy, amino, C$_{1-4}$-alkylamino or —NHCOC$_{1-4}$ alkyl, or
Z and W together form an oxo-group;
R and Y taken together with the nitrogen and carbon atoms to which they are attached form the following group

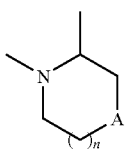

wherein A is O, —CH$_2$—, —NH— or —NC$_{1-4}$-alkyl-, and n is 0, 1 or 2;
Q is a 5- or 6-membered heterocyclic ring containing 1, 2 or 3 heteroatoms independently selected from N, O or S, wherein said 5- or 6-membered heterocyclic ring is optionally substituted one or more groups independently selected from C$_{1-4}$ alkyl, C$_{1-4}$ alkoxy, hydroxyl or halogen.

4. The compound of claim 2 wherein
W is hydrogen or C$_{1-4}$ alkyl;
Z is hydroxyl, halogen, C$_{1-4}$-alkoxy, amino, C$_{1-4}$-alkylamino or —NHCOC$_{1-4}$-alkyl group;
or
Z and W together form an oxo-group;
R and Y taken together with the nitrogen and carbon atoms to which they are attached for the following group

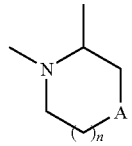

wherein A is O, —CH$_2$—, —NH— or —NC$_{1-4}$-alkyl- and n is 0, 1 or 2;
Q is the following group

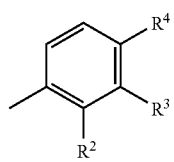

wherein R$^2$ is hydrogen, halogen, hydroxyl, C$_{1-4}$ alkoxy or C$_{1-4}$ alkyl group;
R$^3$ is hydrogen, halogen, hydroxyl, trihalogenomethyl, amino, C$_{1-4}$-alkylamino-, di(C$_{1-4}$)alkylamino-, benzylamino-, benzyl-(C$_{1-4}$)alkylamino-, nitro, benzyl, phenylethyl or
C$_{1-4}$-alkyl, —OR$^5$ group
wherein R$^5$ is C$_{1-4}$-alkyl or benzyl wherein said alkyl and benzyl group is optionally substituted with one or more groups independently selected from halogen or trihalogenomethyl;
—NH—C(=O)—R$^6$,
wherein R$^6$ is phenyl, a 4-7-membered cycloalkyl group, a methylenedioxyphenyl group, C$_{1-4}$ alkyl, benzyl or a heterocyclic ring containing 1 or 2 or 3 heteroatoms independently selected from N, O or S, and wherein said phenyl, 4-7-membered cycloalkyl group, methylenedioxyphenyl group, C$_{1-4}$ alkyl, benzyl and heterocyclic ring are optionally substituted with halogen, C$_{1-4}$ alkyl, C$_{1-4}$ alkoxy;
—NH—C(=O)—NH—R$^7$
wherein R$^7$ is C$_{1-4}$-alkyl, benzyl or phenyl and wherein said C$_{1-4}$-alkyl, benzyl and phenyl is optionally mono- or polysubstituted with a group selected from halogen, C$_{1-4}$-alkoxy, C$_{1-4}$-alkyl or trihalogenomethyl; and
R$^4$ is hydrogen, halogen, hydroxyl, C$_{1-4}$-alkoxy or C$_{1-4}$ alkyl.

5. The compounds of claim 1 wherein
X is benzylamino or —N—C$_{1-4}$-alkyl-benzyl-amino wherein the aromatic ring of said benzylamino and —N—C$_{1-4}$-alkyl-benzyl-amino is optionally substituted with one or more groups independently selected from C$_{1-4}$-alkyl, C$_{1-4}$-alkoxy, halogen or hydroxyl;

Ar is phenyl optionally substituted with one or more groups independently selected from $C_{1-4}$-alkyl, $C_{1-4}$-alkoxy, halogen, trihalogenomethyl or hydroxyl;

R and Y taken together with the nitrogen and carbon atoms to which they are attached form the following group

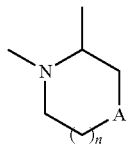

wherein
A is O, —$CH_2$—, —NH— or —N—$C_{1-4}$-alkyl-, and n is 0, 1 or 2;
W is hydrogen;
Z is hydroxyl;
Q is phenyl or a 5- or 6-membered heterocyclic ring containing 1, 2, or 3 heteroatoms independently selected from N, O or S, and wherein said phenyl or 5- or 6-membered heterocyclic ring is optionally substituted with one or more groups independently selected from halogen, $C_{1-4}$ alkyl, $C_{1-4}$ alkoxy or hydroxyl.

6. The compound of claim 1 wherein
Y is hydrogen or $C_{1-4}$ alkyl;
W is hydrogen or $C_{1-4}$ alkyl;
R and Z taken together form a —$(CH_2)_m$-G-, wherein m is 1, 2 or 3 and G is O, —$CH_2$—, —NH— or —$NC_{1-4}$-alkyl-;
Q is a 5- or 6-membered heterocyclic ring containing 1, 2, or 3 heteroatoms independently selected from N, O, or S, and wherein said 5- or 6-membered heterocyclic ring is optionally substituted with one or more groups independently selected from $C_{1-4}$ alkyl, $C_{1-4}$ alkoxy, hydroxyl or halogen,
or Q is the following group a

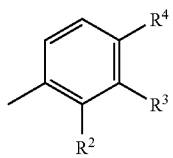

wherein
$R^2$ is hydrogen, halogen, hydroxyl, $C_{1-4}$ alkoxy or $C_{1-4}$ alkyl;
$R^3$ is hydrogen, halogen, hydroxyl, trihalogenomethyl, amino, $C_{1-4}$-alkylamino-, di($C_{1-4}$)alkylamino-, benzylamino-, benzyl-($C_{1-4}$)alkylamino-, nitro, benzyl, phenylethyl, $C_{1-4}$-alkyl, —$OR^5$,
wherein $R^5$ is $C_{1-4}$-alkyl or a benzyl group and wherein said $C_{1-4}$-alkyl and benzyl are optionally substituted with one or more groups independently selected from halogen or trihalogenomethyl;
—NH—C(=O)—$R^6$,
wherein $R^6$ is phenyl,
wherein said phenyl is optionally substituted with halogen;
$C_{1-4}$ alkyl, $C_{1-4}$ alkoxy, a 4-7-membered cycloalkyl group, a methylenedioxyphenyl group, $C_{1-4}$ alkyl, benzyl, or a heterocyclic ring containing 1 or 2 or 3 heteroatoms independently selected from N, O or S;
or —NH—C(=O)—NH—$R^7$
wherein $R^7$ is $C_{1-4}$ alkyl, benzyl or phenyl and wherein said $C_{1-4}$ alkyl, benzyl and phenyl are optionally substituted with halogen, $C_{1-4}$ alkoxy, $C_{1-4}$ alkyl or trihalogenomethyl; and
$R^4$ is hydrogen, halogen, hydroxyl, $C_{1-4}$ alkoxy or $C_{1-4}$ alkyl.

7. The compound of claim 1 wherein
R is hydrogen or $C_{1-4}$ alkyl;
Y is hydrogen or $C_{1-4}$ alkyl;
W is hydrogen or $C_{1-4}$ alkyl;
Z is hydroxyl, halogen, $C_{1-4}$-alkoxy, amino, $C_{1-4}$-alkylamino, —$NHCOC_{1-4}$-alkyl;
or Z and W taken together form an oxo-group;
Q is

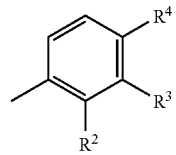

wherein
$R^2$ is hydrogen, halogen, hydroxyl, $C_{1-4}$ alkoxy or $C_{1-4}$ alkyl;
$R^3$ is hydrogen, halogen, hydroxyl, trihalogenomethyl, amino, $C_{1-4}$-alkylamino-, di($C_{1-4}$)alkylamino-, benzylamino-, benzyl-($C_{1-4}$)alkylamino-, nitro, benzyl, phenylethyl
or $C_{1-4}$-alkyl, —$OR^5$,
wherein $R^5$ is $C_{1-4}$-alkyl or benzyl and wherein said $C_{1-4}$-alkyl and benzyl is optionally substituted with one or more groups independently selected from halogen or trihalogenomethyl;
—NH—C(=O)—$R^6$,
wherein $R^6$ is phenyl
wherein said phenyl is optionally substituted with halogen atom;
$C_{1-4}$ alkyl, $C_{1-4}$ alkoxy, a 4-7-membered cycloalkyl group, a methylenedioxyphenyl group, $C_{1-4}$ alkyl, benzyl or a heterocyclic ring containing 1 or 2 or 3 heteroatoms independently selected from N, O or S,
or —NH—C(=O)—NH—$R^7$
wherein $R^7$ is $C_{1-4}$ alkyl, benzyl or phenyl and wherein said $C_{1-4}$ alkyl, benzyl and phenyl is optionally substituted with one or more halogen atom, $C_{1-4}$ alkoxy group, $C_{1-4}$ alkyl group or trihalogenomethyl group, and
$R^4$ is hydrogen, halogen, hydroxyl, $C_{1-4}$ alkoxy or $C_{1-4}$ alkyl.

8. The compound of claim 1 wherein
R is hydrogen or $C_{1-4}$ alkyl;
Y is hydrogen or $C_{1-4}$ alkyl;
W is hydrogen or $C_{1-4}$ alkyl;
Z is hydroxyl, halogen, $C_{1-4}$-alkoxy, amino, $C_{1-4}$-alkylamino, —$NHCOC_{1-4}$-alkyl,
or Z and W taken together form an oxo-group;
Q is a 5- or 6-membered heterocyclic ring containing 1, 2, or 3 heteroatoms independently selected from N, O or S, and wherein said 5- or 6-membered heterocyclic ring is optionally substituted with one or more groups independently selected from $C_{1-4}$ alkyl, $C_{1-4}$ alkoxy, hydroxyl or halogen.

9. The compound of claim 1 which is:

2-Dimethylamino-4-phenylpyrimidine-5-carboxylic acid [2-hydroxy-2-(3-hydroxyphenyl)ethyl]methyl amide;

2-Dimethylamino-4-(2-chlorophenyl)pyrimidine-5-carboxylic acid [2-hydroxy-2-(3-hydroxyphenyl)ethyl] methyl amide;

4-Phenyl-2-[(thiophen-2-yl-methyl)amino]pyrimidine-5-carboxylic acid [2-hydroxy-2-(3-hydroxyphenyl)ethyl] methyl amide;

2-(Benzylmethylamino)-4-phenylpyrimidine-5-carboxylic acid [2-hydroxy-2-(3-hydroxy-phenyl)ethyl]methyl amide;

2-Benzylamino-4-phenylpyrimidine-5-carboxylic acid [2-hydroxy-2-(3-hydroxyphenyl)ethyl]methyl amide;

2-[Benzyl-(2-hydroxyethyl)amino]-4-phenylpyrimidine-5-carboxylic acid [2-hydroxy-2-(3-hydroxyphenyl) ethyl]methyl amide;

2-(Benzylmethylamino)-4-(2-chlorophenyl)pyrimidine-5-carboxylic acid [2-hydroxy-2-(3-hydroxyphenyl) ethyl]methyl amide;

2-(Benzylmethylamino)-4-(2-methylphenyl)pyrimidine-5-carboxylic acid [2-hydroxy-2-(3-hydroxyphenyl) ethyl]methyl amide;

2-(Benzylmethylamino)-4-(2-methoxyphenyl)pyrimidine-5-carboxylic acid [2-hydroxy-2-(3-hydroxyphenyl)ethyl]methyl amide;

2-(2-Chlorobenzylamino)-4-phenylpyrimidine-5-carboxylic acid [2-hydroxy-2-(3-hydroxyphenyl)ethyl] methyl amide;

2-Dimethylamino-4-phenylpyrimidine-5-carboxylic acid [2-(3-benzyloxyphenyl)-2-fluoroethyl]methylamide;

4-Phenyl-2-[methyl-(pyridin-2-ylmethyl)amino]pyrimidine-5-carboxylic acid [2-hydroxy-2-(3-hydroxyphenyl)ethyl]methyl amide;

2-(Benzylmethylamino)-4-(2-iodophenyl)pyrimidine-5-carboxylic acid [2-hydroxy-2-(3-hydroxyphenyl)ethyl] methyl amide;

2,2-Dimethylpropionic acid 3-{2-[(2-dimethylamino-4-phenylpyrimidine-5-carbonyl)methylamino]-1-hydroxyethyl}phenyl ester;

2,2-Dimethylpropionic acid 3-{2-[(2-dimethylamino-4-thiophen-3-yl-pyrimidine-5-carbonyl)methylamino]-1-hydroxyethyl}phenyl ester;

2,2-Dimethylpropionic acid 3-{2-[(2-dimethylamino-4-thiophen-2-yl-pyrimidine-5-carbonyl)methylamino]-1-hydroxyethyl}phenyl ester;

2,2-Dimethylpropionic acid 3-{2-[(2-dimethylamino-4-(2-chlorophenyl)pyrimidine-5-carbonyl)methylamino]-1-hydroxyethyl}phenyl ester;

2,2-Dimethylpropionic acid 3-{2-[(2-dimethylamino-4-(3-chlorophenyl)pyrimidine-5-carbonyl)methylamino]-1-hydroxyethyl}phenyl ester;

2,2-Dimethylpropionic acid 3-{2-[(2-dimethylamino-4-(3-fluorophenyl)pyrimidine-5-carbonyl)methylamino]-1-hydroxyethyl}phenyl ester;

2,2-Dimethylpropionic acid 3-{2-[(2-dimethylamino-4-(4-methoxyphenyl)pyrimidine-5-carbonyl)methylamino]-1-hydroxyethyl}phenyl ester;

2,2-Dimethylpropionic acid 3-{2-[(2-dimethylamino-4-(3,4-methylenedioxyphenyl)pyrimidine-5-carbonyl) methylamino]-1-hydroxyethyl}phenyl ester;

2-Dimethylamino-4-phenylpirimidine-5-carboxylic acid [2-(3-benzyloxyphenyl)-2-hydroxyethyl]methyl amide 2-Dimethylamino-4-(2-fluorophenyl)pyrimidine-5-carboxylic acid [2-(3-benzyloxy phenyl)-2-hydroxyethyl] methyl amide;

2-Dimethylamino-4-(2-chlorophenyl)pyrimidine-5-carboxylic acid [2-(3-benzyloxy phenyl)-2-hydroxyethyl] methyl amide;

4-Phenyl-2-[(pyridin-2-yl-methyl)amino]pyrimidine-5-carboxylic acid (2-hydroxy-1-methyl-2-phenylethyl) methyl amide;

2-(Benzylmethylamino)-4-phenylpyrimidine-5-carboxylic acid (2-hydroxy-1-methyl-2-phenylethyl)methyl amide;

2-(Benzylmethylamino)-4-(2-chlorophenyl)pyrimidine-5-carboxylic acid (2-hydroxy-1-methyl-2-phenylethyl) methyl amide;

2-Benzylamino-4-phenylpyrimidine-5-carboxylic acid (2-hydroxy-1-methyl-2-phenylethyl)methyl amide;

4-Phenyl-2-[(thiophen-2-ylmethyl)amino]pyrimidine-5-carboxylic acid (2-hydroxy-1-methyl-2-phenylethyl) methyl amide;

4-Phenyl-2-[(pyridin-2-ylmethyl)amino]pyrimidine-5-carboxylic acid (2-hydroxy-1-methyl-2-phenylethyl) methyl amide;

2-Dimethylamino-4-phenylpyrimidine-5-carboxylic acid (2-hydroxy-2-{3-[(pyridin-2-carbonyl)amino] phenyl}ethyl)methyl amide;

2-Dimethylamino-4-phenylpyrimidine-5-carboxylic acid [2-(3-benzoylaminophenyl)-2-hydroxyethyl]methyl amide;

2-Dimethylamino-4-phenylpyrimidine-5-carboxylic acid {2-hydroxy-2-[3-(2-methoxy benzoylamino)phenyl] ethyl}methyl amide;

2-Dimethylamino-4-phenylpyrimidine-5-carboxylic acid {2-hydroxy-2-[3-(3-methoxy benzoylamino)phenyl] ethyl}methyl amide;

2-Dimethylamino-4-phenylpyrimidine-5-carboxylic acid (2-hydroxy-2-{3-[(thiophen-2-carbonyl)amino] phenyl}ethyl)methyl amide;

2-Dimethylamino-4-phenylpyrimidine-5-carboxylic acid (2-hydroxy-2-{3-[(thiophen-3-carbonyl)amino] phenyl}ethyl)methyl amide;

2-Dimethylamino-4-phenylpyrimidine-5-carboxylic acid (2-{3-[(furan-3-carbonyl)amino]phenyl}-2-hydroxyethyl)methyl amide;

2-Dimethylamino-4-phenylpyrimidine-5-carboxylic acid (2-hydroxy-2-{3-[(pyridin-3-carbonyl)amino] phenyl}ethyl)methyl amide;

2-Dimethylamino-4-phenylpyrimidine-5-carboxylic acid (2-hydroxy-2-{3-[(pyridin-4-carbonyl)amino] phenyl}ethyl)methyl amide;

2-Dimethylamino-4-phenylpyrimidine-5-carboxylic acid {2-[3-(2,2-dimethylpropionyl amino)phenyl]-2-hydroxyethyl}methyl amide;

2-Dimethylamino-4-phenylpyrimidine-5-carboxylic acid {2-[3-(cyclopentanecarbonyl amino)phenyl]-2-hydroxyethyl}methyl amide;

2-Dimethylamino-4-phenylpyrimidine-5-carboxylic acid {2-hydroxy-2-[3-(3-chloro benzoylamino)phenyl] ethyl}methyl amide;

2-Dimethylamino-4-phenylpyrimidine-5-carboxylic acid {2-[3-(3-tert-butylureido) phenyl]-2-hydroxyethyl}methyl amide;

2-(Benzylmethylamino)-4-phenylpyrimidine-5-carboxylic acid [2-hydroxy-2-(4-hydroxy-phenyl)ethyl]methyl amide;

2-(Benzylmethylamino)-4-phenylpyrimidine-5-carboxylic acid [2-hydroxy-2-(3-fluoro phenyl)ethyl]methyl amide;

2-(Benzylmethylamino)-4-phenylpyrimidine-5-carboxylic acid [2-hydroxy-2-(4-fluoro phenyl)ethyl]methyl amide;

2-(Benzylmethylamino)-4-phenylpyrimidine-5-carboxylic acid [2-hydroxy-2-(3-methoxy-phenyl)ethyl]methyl amide;

2-(Benzylmethylamino)-4-phenylpyrimidine-5-carboxylic acid [2-hydroxy-2-(4-methoxy-phenyl)ethyl]methyl amide;

2-(Benzylmethylamino)-4-phenylpyrimidine-5-carboxylic acid (2-phenyl-2-hydroxyethyl)-methyl amide;

2-(Benzylmethylamino)-4-phenylpyrimidine-5-carboxylic acid [2-(3-aminophenyl)-2-hydroxyethyl]methyl amide;

2-Benzylamino-4-phenylpyrimidine-5-carboxylic acid [2-(3,4-dihydroxyphenyl)-2-hydroxyethyl]methyl amide;

2-Dimethylamino-4-phenylpyrimidine-5-carboxylic acid [2-(3-benzyloxyphenyl)-2-fluoroethyl]methyl amide;

(±) Anti-[2-(benzylmethylamino)-4-phenylpyrimidin-5-yl]-[2-(hydroxyphenylmethyl)-piperidin-1-yl]methanone;

(±) Anti-[2-(benzylmethylamino)-4-phenylpyrimidin-5-yl]-{2-[hydroxy-(3-methoxyphenyl)methyl]piperidin-1-yl}methanone;

(±) Anti-[2-(benzylmethylamino)-4-phenylpyrimidin-5-yl]-{2-[hydroxy-(3-hydroxyphenyl)methyl]piperidin-1-yl}methanone;

(±) Anti-[2-(benzylmethylamino)-4-phenylpyrimidin-5-yl]-{2-[(3-fluorophenyl) hydroxymethyl]piperidin-1-yl}methanone;

(±) Anti-[2-(benzylmethylamino)-4-phenylpyrimidin-5-yl]-[2-(hydroxypyiridin-3-yl-methyl)piperidin-1-yl] methanone;

(±) Anti-[2-(Benzylmethylamino)-4-(2-chlorophenyl)pyrimidin-5-yl]-[2-(hydroxyphenyl-methyl)piperidin-1-yl]methanone (±) Anti-[2-(benzylmethylamino)-4-phenylpyrimidin-5-yl]-[2-(hydroxypyridin-2-ylmethyl)piperidin-1-yl] methanone 2-(Benzylmethylamino)-4-(2-bromophenyl)pyrimidine-5-carboxylic acid [2-(3,4-dihydroxyphenyl)-2-hydroxyethyl]methyl amide 2-(Benzylmethylamino)-4-(2-bromophenyl)pyrimidine-5-carboxylic acid [2-hydroxy-2-(3-hydroxyphenyl) ethyl]methyl amide 2-(Benzylmethylamino)-4-(2-fluorophenyl)pyrimidine-5-carboxylic acid [2-(4-chloro-phenyl)-2-hydroxyethyl]methyl amide 2-(Benzylmethylamino)-4-phenylpyrimidine-5-carboxylic acid [2-(4-chlorophenyl)-2-hydroxyethyl]methyl amide 2-(Benzylmethylamino)-4-phenylpyrimidine-5-carboxylic acid (2-benzo[1,3]dioxol-5-yl-2-hydroxyethyl)methyl amide 2-(Benzylmethylamino)-4-(2-chlorophenyl)pyrimidine-5-carboxylic acid [2-(3,4-dihydroxyphenyl)-2-hydroxyethyl]methyl amide 2-(Benzylmethylamino)-4-phenylpyrimidine-5-carboxylic acid [2-(4-cyanophenyl)-2-hydroxyethyl]methyl amide 4-(2-Chlorophenyl)-2-dimethylaminopyrimidine-5-carboxylic acid (2-hydroxy-2-{3-[(pyridine-4-carbonyl) amino]phenyl}ethyl)methyl amide 2-(Ethyl-pyridin-3-ylmethyl-amino)-4-(2-fluorophenyl) pyrimidine-5-carboxylic acid [2-hydroxy-2-(3-hydroxyphenyl)ethyl]methyl amide (±) Anti-[2-(benzylmethylamino)-4-phenylpyrimidin-5-yl]-{2-[(4-fluorophenyl)-hydroxymethyl]piperidin-1-yl}methanone (±) Anti-[2-(benzylmethylamino)-4-phenylpyrimidin-5-yl]-[2-(hydroxy-p-tolyl-methyl)piperidin-1-yl]methanone (±) Anti-[2-(hydroxyphenylmethyl)piperidin-1-yl]-[2-(3-methoxybenzylamino)-4-phenylpyrimidin-5-yl]methanone (±) Anti-[2-(benzylmethylamino)-4-phenylpyrimidin-5-yl]-{2-[(3-chlorophenyl)-hydroxymethyl]piperidin-1-yl}methanone (±) Anti-{2-[(4-chlorobenzyl)methylamino]-4-phenylpyrimidin-5-yl}-[2-(hydroxy-phenylmethyl)piperidin-1-yl]methanone (±) Anti-[2-(benzylmethylamino)-4-phenylpyrimidin-5-yl]-[2-(hydroxy-m-tolyl-methyl)piperidin-1-yl]methanone (±) Anti-{2-[(4-fluorobenzyl)methylamino]-4-phenylpyrimidin-5-yl}-[2-(hydroxy-phenylmethyl)piperidin-1-yl]methanone (±) Anti-[2-(benzylmethylamino)-4-phenylpyrimidin-5-yl]-[2-(hydroxy-o-tolyl-methyl)piperidin-1-yl]methanone (±) Anti-[2-(benzylmethylamino)-4-phenylpyrimidin-5-yl]-{2-[(2-fluorophenyl)-hydroxymethyl]piperidin-1-yl}methanone (±) Anti-[2-(benzylmethylamino)-4-phenylpyrimidin-5-yl]-{2-[hydroxy-(4-methoxy-phenyl)methyl]piperidin-1-yl}methanone (±) Anti-[2-(4-fluorobenzylamino)-4-phenylpyrimidin-5-yl]-[2-(hydroxy-phenylmethyl)piperidin-1-yl]methanone (±) Anti-[2-(benzylmethylamino)-4-phenylpyrimidin-5-yl]-{2-[(3-chloro-4-fluorophenyl)hydroxymethyl]piperidin-1-yl}methanone (±) Anti-[2-(benzylmethylamino)-4-phenylpyrimidin-5-yl]-{2-[(3,4-difluorophenyl)-hydroxymethyl]piperidin-1-yl}methanone (±) Anti-[2-(3-chlorobenzylamino)-4-phenylpyrimidin-5-yl]-[2-(hydroxy-phenylmethyl)piperidin-1-yl]methanone (±) Anti-[2-(benzylmethylamino)-4-(2-chlorophenyl)-pyrimidin-5-yl]-[2-(hydroxy-phenylmethyl)piperidin-1-yl]methanone (±) Anti-[2-(benzylmethylamino)-4-phenylpyrimidin-5-yl]-[2-(hydroxypyridin-4-yl-methyl)piperidin-1-yl] methanone (±) Anti-[2-(benzylmethylamino)-4-(2-fluorophenyl)pyrimidin-5-yl]-[2-(hydroxy-phenylmethyl)piperidin-1-yl] methanone (±) Anti-{2-[(3-chlorobenzyl)methylamino]-4-phenylpyrimidin-5-yl}-[2-(hydroxy-phenylmethyl)piperidin-1-yl]methanone (±) Anti-[2-(benzylmethylamino)-4-phenylpyrimidin-5-yl]-{2-[(2-chlorophenyl)-hydroxymethyl]piperidin-1-yl}methanone (±) Anti-[2-(benzylmethylamino)-4-phenylpyrimidin-5-yl]-[2-(hydroxy-thiophen-3-yl-methyl)piperidin-1-yl] methanone (±) Anti-[2-(3-chloro-4-fluorobenzylamino)-4-phenylpyrimidin-5-yl]-[2-(hydroxy-phenylmethyl)piperidin-1-yl]methanone (±) Anti-{2-[(3-chloro-4-fluorobenzyl)methylamino]-4-phenylpyrimidin-5-yl}-[2-(hydroxyphenylmethyl)-piperidin-1-yl]methanone (±) Anti-[2-(benzylmethylamino)-4-(4-chlorophenyl)pyrimidin-5-yl]-[2-(hydroxy-phenylmethyl)piperidin-1-yl]methanone (±) Anti-[2-(3-chloro-4-fluorobenzylamino)-4-phenylpyrimidin-5-yl]-[2-(hydroxy-thiophen-3-yl-methyl)piperidin-1-yl]methanone.

10. A pharmaceutical composition comprising a compound of claim 1 and a pharmaceutically acceptable carrier.

11. A process for preparing the compound of claim 1 comprising the step of reacting a compound of formula II

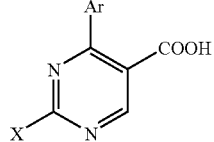

(II)

wherein of X and Ar are as defined in claim 1, with a compound of formula (III)

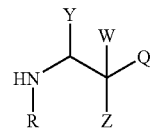

(III)

wherein R, Y, W, Z and Q are as defined in claim 1.

* * * * *

UNITED STATES PATENT AND TRADEMARK OFFICE
CERTIFICATE OF CORRECTION

| | | |
|---|---|---|
| PATENT NO. | : 7,812,031 B2 | Page 1 of 5 |
| APPLICATION NO. | : 11/463825 | |
| DATED | : October 12, 2010 | |
| INVENTOR(S) | : Peter Aranyi et al. | |

It is certified that error appears in the above-identified patent and that said Letters Patent is hereby corrected as shown below:

Title Pg, in field (56), in column 2, under "Other Publications", line 4, delete "ofTetrahydrofolic" and insert -- of Tetrahydrofolic --, therefor.

Title Pg, in field (56), in column 2, under "Other Publications", line 5, delete "5-pyrimid yi)" and insert -- 5-pyrimidyl) --, therefor.

Title Pg, in field (56), in column 2, under "Other Publications", line 6, delete "glumtamic" and insert -- glutamic --, therefor.

Title Pg, in field (56), in column 2, under "Other Publications", line 23, delete "ofEthyl" and insert -- of Ethyl --, therefor.

Title Pg, in field (56), in column 2, under "Other Publications", line 23, delete "amino?-4-" and insert -- aminol-4- --, therefor.

Title Pg, in field (56), in column 2, under "Other Publications", line 24, delete "carboxyl ate:" and insert -- carboxylate: --, therefor.

Title Pg, in field (56), in column 2, under "Other Publications", line 34, delete "amino?-4" and insert -- aminol-4 --, therefor.

Title Pg, in field (56), in column 2, under "Other Publications", line 34, delete "2-im idazolines," and insert -- 2-imidazolines, --, therefor.

In column 1, line 19, delete "crutial" and insert -- crucial --, therefor.

In column 1, line 33, delete "heterogenous" and insert -- heterogeneous --, therefor.

In column 1, line 66, delete "sub-classess" and insert -- sub-classes --, therefor.

Signed and Sealed this
Tenth Day of January, 2012

David J. Kappos
*Director of the United States Patent and Trademark Office*

CERTIFICATE OF CORRECTION (continued)
U.S. Pat. No. 7,812,031 B2

In column 2, line 14, delete "steam," and insert -- stem, --, therefor.

In column 2, line 35, delete "viva" and insert -- vivo --, therefor.

In column 2, line 55, delete "$C_{1-4}$-allyl" and insert -- $C_{1-4}$-alkyl --, therefor.

In column 2, line 56, delete "$C_{1-4}$-allyl" and insert -- $C_{1-4}$-alkyl --, therefor.

In column 3, line 16, delete "-NSC" and insert -- -NHC --, therefor.

In column 4, line 1, delete "$C_{1-4}$ alky'" and insert -- $C_{1-4}$-alkyl --, therefor.

In column 4, line 35, delete "$C_{1-4}$alkyl" and insert -- $C_{1-4}$ alkyl --, therefor.

In column 4, line 36, delete "$C_{1-4}$ allyl" and insert -- $C_{1-4}$ alkyl --, therefor.

In column 4, line 47, delete "$C_{1-4}$-allyl" and insert -- $C_{1-4}$-alkyl --, therefor.

In column 5, line 1, before "W" delete "if".

In column 5, line 52, delete "$C_{1-4}$ allyl" and insert -- $C_{1-4}$ alkyl --, therefor.

In column 6, line 5, delete "C" and insert -- G --, therefor.

In column 6, line 6, delete "$NC_{1-4}$-allyl" and insert -- $NC_{1-4}$-alkyl --, therefor..

In column 6, line 35, delete "ringy" and insert -- ring --, therefor.

In column 6, line 37, delete "C(-O)" and insert -- C(=O) --, therefor.

In column 7, line 9, delete "allyl" and insert -- alkyl --, therefor.

In column 7, line 16, delete "croup," and insert -- group, --, therefor.

In column 7, line 32, delete "$C_{1-4}$ allyl-," and insert -- $C_{1-4}$ alkyl-, --, therefor.

In column 7, line 66, delete "Cab alkyl-," and insert -- $C_{1-4}$ alkyl-, --, therefor.

In column 8, line 17, delete "tert.-butyl" and insert -- tert-butyl --, therefor.

In column 8, line 59, delete "pyridine-5-" and insert -- pyrimidine-5- --, therefor.

In column 9, line 23, delete "phenylpirimidine" and insert -- phenylpyrimidine --, therefor.

In column 10, line 8, delete "dimethylpropynyl" and insert -- dimethylpropionyl --, therefor.

CERTIFICATE OF CORRECTION (continued)
U.S. Pat. No. 7,812,031 B2

In column 10, line 27, delete "(Benzylmethylamino)$_4$-" and insert -- (Benzylmethylamino)-4- --, therefor.

In column 12, line 7, delete "5-yl][2-" and insert -- 5-yl]-[2- --, therefor.

In column 12, line 33, delete "IC$_{5-22}$" and insert -- IC$_{50}$ 22 --, therefor.

In column 13, line 15, delete "die" and insert -- the --, therefor.

In column 13, line 37, delete "1-etyl" and insert -- 1-ethyl --, therefor.

In column 13, line 40, delete "sovent" and insert -- solvent --, therefor.

In column 14, line 9, delete "dinucleofils," and insert -- dinucleophiles, --, therefor.

In column 14, line 36, delete "croup," and insert -- group, --, therefor.

In column 14, line 50, delete "C$_{1-4}$-allyl" and insert -- C$_{1-4}$-alkyl --, therefor.

In column 16, line 54, delete "(DC)" and insert -- (IX) --, therefor.

In column 18, line 42, delete "phantome" and insert -- phantom --, therefor.

In column 19, line 10, delete "lecitine." and insert -- lecitin. --, therefor.

In column 22, line 48, delete "sulplanyl" and insert -- sulphanyl --, therefor.

In column 23, line 17, after "307" insert -- . --.

In column 23, line 33, after "340" insert -- . --.

In column 23, line 64-65, delete "tris pyrrolidino)" and insert -- tris(pyrrolidino) --, therefor.

In column 29-30, Example 33, line 3, delete "pale-yellow" and insert -- Pale-yellow --, therefor.

In column 31, line 52, delete "pyvaloyl" and insert -- pivaloyl --, therefor.

In column 39, line 63, after "Z=OH," delete "Z=OH,". (Second Occurrence)

In column 39, line 63, after "W=H," insert -- R$^2$=H, --.

In column 40, line 4, delete "stored" and insert -- stirred --, therefor.

In column 40, line 12, delete "stored" and insert -- stirred --, therefor.

CERTIFICATE OF CORRECTION (continued)

U.S. Pat. No. 7,812,031 B2

In column 49, line 53, delete "R" and insert -- $R^3$ --, therefor.

In column 49, line 65, delete "water," and insert -- water. --, therefor.

In column 50, line 56, delete "R=OH," and insert -- $R^3$=OH, --, therefor.

In column 51, line 42, delete "1 mmol/g," and insert -- ~1 mmol/g, --, therefor.

In column 51, line 47, delete "NAN-" and insert -- N,N- --, therefor.

In column 51, line 63, delete "(pH 7)" and insert -- (pH=7) --, therefor.

In column 51, line 64, delete "oft" and insert -- off, --, therefor.

In column 52, line 36, delete "(121 pd." and insert -- (121 µl, --, therefor.

In column 54, line 18, after "2-" insert -- ( --.

In column 54, line 62, delete "die" and insert -- the --, therefor.

In column 54, line 67, delete "[$MH^{30}$]" and insert -- [$MH^+$] --, therefor.

In column 55, line 3, delete "(m, 1H," and insert -- (m, 1H), --, therefor.

In column 55, line 51, delete "X Me" and insert -- X=Me --, therefor.

In column 55, line 63, delete "($C_1H_{27}NO_4$ 321.414)" and insert -- ($C_{18}H_{27}NO_4$ 321.414) --, therefor.

In column 56, line 25, delete "LC/MS)" and insert -- LC/MS --, therefor.

In column 57, line 2, delete "(s, 1H)," and insert -- (bs 1H), --, therefor.

In column 57, line 15, delete "210)" and insert -- 210, --, therefor.

In column 58, line 9, after "149g)" insert -- . --.

In column 58, line 66, after "149e)" insert -- . --.

In column 58, line 67, delete "526) ." and insert -- 526) --, therefor.

In column 97, line 52, delete "gentamycin," and insert -- gentamicin, --, therefor.

In column 98, line 43, after "buffer" insert -- . --.

In column 98, line 52, after "acid" insert -- . --.

CERTIFICATE OF CORRECTION (continued)
U.S. Pat. No. 7,812,031 B2

In column 102, line 62, in claim 5, delete "compounds" and insert -- compound --, therefor.

In column 103, line 16, in claim 5, delete "A" and insert -- -A --, therefor.

In column 104, line 38, in claim 6, delete "phenyl" and insert -- phenyl, --, therefor.

In column 105, line 63, in claim 9, delete "phenylpirimidine" and insert -- phenylpyrimidine --, therefor.

In column 107, line 32, in claim 9, delete "(hydroxypyiridin" and insert -- (hydroxypyridin --, therefor.